US006376230B1

(12) United States Patent
Aikins et al.

(10) Patent No.: US 6,376,230 B1
(45) Date of Patent: Apr. 23, 2002

(54) STEREOSELECTIVE PROCESS FOR PRODUCING INTERMEDIATES OF CRYPTOPHYCINS

(75) Inventors: James Abraham Aikins, Pendleton; Barbara Shreve Briggs; Tony Yantao Zhang, both of Indianapolis; Milton Joseph Zmijewski, Jr., Carmel, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/415,778

(22) Filed: Oct. 8, 1999

Related U.S. Application Data

(60) Provisional application No. 60/104,659, filed on Oct. 16, 1998.

(51) Int. Cl.[7] .............................. C12P 41/00; C12P 7/26
(52) U.S. Cl. ....................................... 435/280; 435/148
(58) Field of Search ................................ 438/280, 148

(56) References Cited

U.S. PATENT DOCUMENTS

| 4,845,085 A | 7/1989 | Sesin ........................... 31/395 |
| 4,845,086 A | 7/1989 | Sesin ........................... 31/395 |
| 4,868,208 A | 9/1989 | Sesin et al. .................. 514/475 |
| 4,946,835 A | 8/1990 | Hirsch et al. ................ 514/183 |
| 6,103,913 A * | 8/2000 | Hay et al. ..................... 549/292 |

FOREIGN PATENT DOCUMENTS

| WO | WO 95/17093 | 12/1994 | .......... A01N/37/18 |
| WO | WO 96/40184 | 3/1996 | .......... A61K/38/00 |
| WO | WO 96/39829 | 6/1996 | .......... A01N/37/18 |
| WO | WO 97/07798 | 8/1996 | .......... A61K/31/395 |
| WO | WO 97/08334 | 8/1996 | ............ C12P/21/04 |
| WO | WO 97/23211 | 12/1996 | .......... A61K/31/395 |
| WO | WO 98/08505 | 8/1997 | .......... A61K/31/395 |
| WO | WO 98/08506 | 8/1997 | .......... A61K/31/395 |
| WO | WO 98/08829 | 8/1997 | .......... C07D/273/08 |

OTHER PUBLICATIONS

Russell A. Barrow, et al., Total Synthesis of Cryptophycins. Revision of the Structures of Cryptophycins A and C. *J. Am. Chem. Soc.* (1995), 117, 2479–2490.

Robert E. Schwartz, et al. Pharmaceuticals From Cultured Algae. *Journal of Industrial Microbiology*, 5 (1990) 113–123.

Motomasa Kobayashi, et al. A total synthesis of Arenastatin A, an extremely potent cyctotoxic eepsipeptide, from the Okinawan marine sponge *Dysidea Arenaria*, *Chem. Pharm. Bull.* (1994) 42 (11);2394–2396.

Charles D. Smith, et al., Cryptophycin: A New Antimicrotubule Agent Active Against Drug–Resistant Cells. *Cancer Research* 54, 3779–3784, Jul. 15, 1994.

Golakoti Trimurtulu, et al., Total Structures of Cryptophycins, Potent Antitumor Depsipeptides From the Blue–Green Alga Nostoc SP. Strain GSV 224. *J. Am. Chem. Soc.* 1994, 116, 4729–4737.

Kristen Kerksiek, et al., Interaction of Cryptophycin 1 With Tubulin and Microtubules. *FEBS Letters* 377 (1995) 59–61.

Motomasa Kobayashi, et al. Improved Total Synthesis and Structure–Activity Relationship of Arenastatin A, A Potent Cytotoxic Spongean Depsipeptide. *Chem. Pharm. Bull* 43 (9) 1598–1600 (1995).

Trimurtulu Golakoti, et al. Strucutre Determination, Conformational Analysis, Chemical Stability Studies, and Antitumor Evaluation of the Cryptophycins. Isolation of 18 New Analogs from Nostoc SP. Strain GSV 224. *J. Am. Chem. Soc.*, 1995, 117, 12030–12049.

Ruoli Bai, et al., Characterization of the Interaction of Cryptophycin 1 With Tubulin: Binding in the Vinca Domain, Competitive Inhibition of Dolastatin 10 Binding, and an Unusual Aggregation Reaction. *Cancer Research* 56, 4398–4406, Oct. 1, 1996.

Charles D. Smith, et al. Mechanism of Action of Cryptophycin. *Journal of Biological Chemistry*, vol. 271, No. 11, Mar. 15, 1996, pp. 6192–6198.

Gregorz M. Salamonczyk, et al. Total Synthesis of Cryptophycins Via a Chemoenzymatic Approach. *J. Org. Chem.*, 1996, 61, 6893–6900.

Rabindra Rej, et al. total synthesis of cryptophycins and their 16–(3–phenylacryloyl) derivatives. *J. Org. Chem.* 1996, 61, 6289–6295.

Richard E. Moore, et al. The Search For New Antitumor Drugs From Blue–Green Algae. *Current Pharmaceutical Design*, 1996, 2, 317–330.

T.H. Corbett, et al. Preclinical Anticancer Activity of Cryptophycin–8. *Journal of Experimental Therapeutics and Oncology*, vol. 1, No. 2, Mar. 1996, pp. 95–108.

Dulal Panda, et al. Mechanism of Action of the Unusually Potent Microtubule Inhibitor Cryptophycin 1. *Biochemistry* 1997, 36, 12948–12953.

Kevin M. Gardinier, et al. Enantiospecific Total Synthesis of the Potent Antitumor Macrolides Cryptophycins 1 and 8. *J. Org. Chem.* 1997, 62, 7098–7099.

Syed M. Ali, et al. Formal Syntheses of Cryptophycin A and Arenastatin A. *Tetrahedron Letters*, vol. 38, No. 10, pp. 1703–1706, 1997.

Gottumukkala V. Subbaraju, et al., Three New Cryptophycins From Nostoc SP. GSV 224, *J. Nat. Prod.*, 1997, 60, 302–305.

* cited by examiner

*Primary Examiner*—Sandra E. Saucier
(74) *Attorney, Agent, or Firm*—Robert D. Titus

(57) ABSTRACT

This invention provides processes for preparing intermediates useful for the preparation of cryptophycin compounds.

15 Claims, No Drawings

STEREOSELECTIVE PROCESS FOR PRODUCING INTERMEDIATES OF CRYPTOPHYCINS

CROSS-REFERENCE

This application claims the benefit of U.S. Provisional Application No. 60/104,659, filed Oct. 16, 1998.

BACKGROUND OF THE INVENTION

Neoplastic diseases, characterized by the proliferation of cells not subject to the normal control of cell growth, are a major cause of death in humans and other mammals. Clinical experience in cancer chemotherapy has demonstrated that new and more effective drugs are desirable to treat these diseases. Such clinical experience has also demonstrated that drugs which disrupt the microtubule system of the cytoskeleton can be effective in inhibiting the proliferation of neoplastic cells.

Cryptophycin compounds can now be prepared using a total synthetic process; see for example, Barrow, R. A. et al., *J. Am. Chem. Soc.* 117, 2479 (1995).

The processes claimed herein provide important elements needed for an efficient total synthetic route for preparing useful cryptophycin compounds and intermediates.

4-Hydroxy-5,6-dihydropyran-2-one and derivatives thereof are important intermediates for a number of natural products; D.Seebach et al., *Angew. Chem. Int. Ed.* 13, 77 (1974); R. M. Carlson et al., *J. Org. Chem.* 40, 1610 (1975). Additionally, this series of compounds has been used for the synthesis of pharmaceuticals, for example, the drug tetrahydrolipstatin ("THL"); J. J. Landi, Jr. et al., *Tetrahedron Lett.*, 34, 277 (1993). Current art teaches that in order to form a carbon-carbon bond at the terminal (4-) position of an acylacetate, two equivalents of strong base, for example sodium hydride and n-butyl lithium, in an aprotic solvent must be used to deprotonate both the 2- and 4-positions, proceeding through selective alkylation of a dianion with one equivalent of electrophiles; S. M. Huckin et al., *Can. J. Chem.* 52, 2157 (1974); S. M. Huckin et al., *J. Am. Chem. Soc.* 96, 1082 (1974); N. Petragnani et al., *Synthesis*, 521, 78 (1982); J. R. Peterson et al., *Syn. Commun.* 18, 949 (1988); D. Seebach et al., *Angew. Chem.* 86, 40 (1974); H. Kashihara et al., *Chem. Pharm. Bull.* 34, 4527 (1986).

However, even under such harsh conditions, paraformaldehyde or formaldehyde have been poor electrophiles and product yield has been low. In fact, a toxic reagent, $PhCH_2OCH_2Cl$ has been used instead of paraformaldehyde for this purpose in a multistep synthesis; E. C. Taylor et al., *J. Org. Chem.* 50, 5223 (1985).

The present invention provides a process for making intermediates of cryptophycin compounds, including Fragment A analogs of cryptophycin, as well as a process for making cryptophycin compounds using selected intermediates.

The present invention further provides novel intermediates useful in the preparation of cryptophycin compounds.

SUMMARY OF THE INVENTION

The present invention provides a process for the preparation of a compound of the formula:

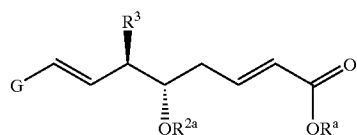

(I)

wherein

G is $C_1$–$C_{12}$ alkyl, $C_2$–$C_{12}$ alkenyl, $C_2$–$C_{12}$ alkynyl, or Ar;

Ar is an aromatic or heteroaromatic group or a substituted aromatic or heteroaromatic group;

$R^3$ is $C_1$–$C_6$ alkyl;

$R^{2a}$ is trityl or a suitable silyl protecting group; and $R^a$ is hydrogen, allyl or $C_1$–$C_6$ alkyl; or a pharmaceutically acceptable salt thereof;

said process comprising the steps of:

(a) contacting a compound of the formula:

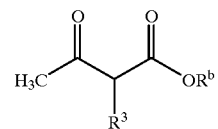

(2)

wherein $R^b$ is a suitable carboxy protecting group; and $R^3$ is as defined above; with a cyclizing agent to form a compound of the formula:

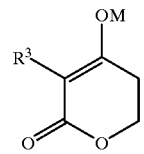

(3)

wherein $R^3$ is as defined above and M is hydrogen or a cation;

(b) stereoselectively reducing the compound of formula (3) with a stereoselective reducing agent to yield a compound of the formula:

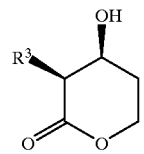

(4)

wherein $R^3$ is defined as above;

(c) reacting a compound of formula (4) with a hydroxy protecting agent to yield a compound of the formula:

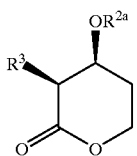

(5)

wherein $R^{2a}$ is trityl or a suitable silyl protecting group, and $R^3$ is as defined above;

(d) reacting the compound of formula (5) with a reducing agent followed by an olefinating reagent to form a compound of the formula:

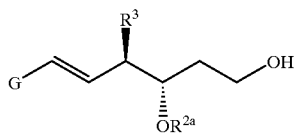

(6)

wherein G, $R^3$ and $R^{2a}$ are as defined above;

(e) reacting the compound of formula (6) with an oxidizing agent to provide a compound of the formula:

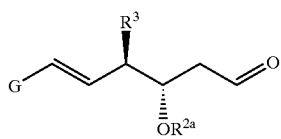

(7)

wherein G, $R^3$ and $R^{2a}$ are as defined above; and (f) reacting the compound of formula (7) with an alkyl ester forming agent, optionally with a hydrolyzing agent to provide a compound of formula (I) and optionally forming a pharmaceutically acceptable salt thereof.

This invention further comprises a process for preparing a cryptophycin compound using a compound of formula (I).

This invention further comprises the novel compounds of formulae (3), (4) and (5).

DETAILED DESCRIPTION OF THE INVENTION

As used in the application:

(a) the designation "▶—" refers to a bond that protrudes forward out of the plane of the page;

(b) the designation "∣∣∣∣∣∣·" refers to a bond that protrudes backward out of the plane of the page; and (c) the designation "⌇⌇⌇" refers to a bond for which the stereochemistry is not designated.

As used herein, the term "pharmaceutically acceptable salt" refers to either acid addition salts or base addition salts.

The expression "pharmaceutically acceptable acid addition salt" is intended to apply to any non-toxic organic or inorganic acid addition salt of the compounds of formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di- and tricaboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxy-benzoic, and sulfonic acids such as p-toluenesulfonic acid, methane sulfonic acid and 2-hydroxyethane sulfonic acid. Such salts can exist in either hydrated or substantially anhydrous form.

The expression "pharmaceutically acceptable basic addition salts" is intended to apply to any non-toxic organic or inorganic basic addition salts of the compounds of formula I or any of its intermediates. Illustrative bases which form suitable salts include alkali metal or alkaline-earth metal hydroxides such as sodium, potassium, calcium, magnesium or barium hydroxides; ammonia and aliphatic, cyclic or aromatic organic amines such as methylamine, dimethylamine, trimethylamine, diethylamine, triethylamine, isopropyldiethylamine, pyridine and picoline.

As used herein, the term "$C_1-C_{12}$ alkyl" refers to a saturated straight or branched chain hydrocarbon group of from one to twelve carbon atoms. Included within the scope of this term are methyl, ethyl, n-propyl, isopropyl, n-butyl, isobutyl, sec-butyl, tert-butyl, pentyl, neopentyl, 2-methylbutyl, 3-methylbutyl, hexyl, heptyl, octyl, nonyl, decyl and the like. Included within the term is the term "$C_1-C_6$ alkyl" which refers to a saturated, unsaturated, straight or branched chain hydrocarbon radical of from one to six carbon atoms. Included within the scope of this term are methyl, ethyl, n-propyl, isopropyl, n-butyl, isobutyl, sec-butyl, tert-butyl, pentyl, neopentyl, 2-methylbutyl, 3-methylbutyl, hexyl and the like. Included within the terms "$C_1-C_{12}$ alkyl" and "$C_1-C_6$ alkyl" is the terms "$C_1-C_3$ alkyl" which refers to a saturated, unsaturated, straight or branched chain hydrocarbon radical of from one to three carbon atoms. Included within the scope of this term are methyl, ethyl, isopropyl, and the like.

"Substituted ($C_1-C_6$)alkyl" refers to a $C_1-C_6$ alkyl group that may include up to three (3) substituents containing one or more heteroatoms. Examples of such substituents are OH, $NH_2$, $CONH_2$, $CO_2H$, $PO_3H_2$ and $SO_2R^{21}$ wherein $R^{21}$ is hydrogen, $C_1-C_3$ alkyl or aryl.

The term "($C_3-C_8$)cycloalkyl" refers to a saturated $C_3-C_8$ cycloalkyl group. Included within this group are cyclopropyl, cyclobutyl, cyclohexyl, cyclooctyl, and the like. A "substituted ($C_3-C_8$)cycloalkyl group" refers to a ($C_3-C_8$)cycloalkyl group having up to three $C_1-C_3$ alkyl, halo, or $OR^{21}$ substituents. The substituents may be attached at any available carbon atom. Cyclohexyl is an especially preferred cycloalkyl group. The term "—$(CH_2)_m$—$(C_3-C_5)$ cycloalkyl" where m is an integer one, two or three refers to a cyclopropyl, cyclobutyl or cyclopentyl ring attached to a methylidene, ethylidene or propylidene substituent.

The term "$C_2-C_{12}$ alkenyl" refers to an unsaturated straight or branched chain hydrocarbon radical of from two to twelve carbon atoms and having from one to three triple bonds. Included within the scope of this term are ethenyl, propenyl, isopropenyl, n-butenyl, isobutenyl, pentenyl, 2-methylbutenyl, 3-methylbutenyl, hexenyl, octenyl, nonenyl, decenyl and the like. It is especially preferred that alkenyl have only one double bond.

The term "$C_2-C_{12}$ alkynyl" refers to an unsaturated straight or branched chain hydrocarbon radical of from two to twelve carbon atoms and having from one to three triple bonds. Included within the scope of this term are ethynyl, propynyl, isopropynyl, 2-methypropynyl, hexynyl, decynyl, and the like. It is particularly preferred that alkynyl has only one triple bond.

The term "$C_1$–$C_6$ alkoxy" refers to a straight or branched alkoxy group containing from one to six carbon atoms, such as methoxy, ethoxy, n-propoxy, isopropoxy, n-butoxy, isobutoxy, pentoxy, 2-methylpentoxy, and the like. The term "($C_1$–$C_6$ alkoxy)phenyl" refers to a phenyl group substituted with a $C_1$–$C_6$ alkoxy group at any available carbon on the phenyl ring.

The term "halo" refers to chloro, bromo, fluoro, or iodo.

The terms "aromatic group" and "heteroaromatic group" refer to common aromatic rings having 4n+2 pi electrons in a monocyclic or bicyclic conjugated system. The term "aryl" refers to an aromatic group, and the term "aralkyl" refers to an aryl($C_1$–$C_6$-alkyl) group. Examples of aromatic groups are phenyl, benzyl and naphthyl. Heteroaromatic groups will contain one or more oxygen, nitrogen and/or sulfur atoms in the ring. Examples of heteroaromatic groups include furyl, pyrrolyl, thienyl, pyridyl and the like. When the aromatic or heteroaromatic groups are substituted, they may have from one to three independently selected $C_1$–$C_6$ alkyl, $C_1$–$C_6$-alkoxy or halo, substituents. The aromatic groups may be further substituted with trifluoromethyl, COOR$^{57}$ (wherein R$^{57}$ is hydrogen or $C_1$–$C_6$ alkyl), PO$_3$H, SO$_3$H, SO$_2$R$^{57}$, N(R$^{59}$)(R$^{60}$) (wherein R$^{59}$ is hydrogen or $C_1$–$C_6$ alkyl and R$^{60}$ is hydrogen, $C_1$–$C_6$ alkyl, BOC or FMOC), —CN, —NO$_2$, —OR$^{57}$, —CH$_2$OC(O) (CH$_2$)$_{m'}$NH$_2$ (wherein m' is an integer 1 to 6) or —CH$_2$—O—Si(R$^{57}$)(R$^{58}$) (R$^{59}$) (wherein R$^{58}$ is hydrogen or $C_1$–$C_6$ alkyl). Especially preferred substituents for the aromatic groups include methyl, halo, N(R$^{59}$) (R$^{60}$), and —OR$^{57}$. The substituents may be attached at any available carbon atom.

Especially preferred heterocyclic or substituted heterocyclic groups include:

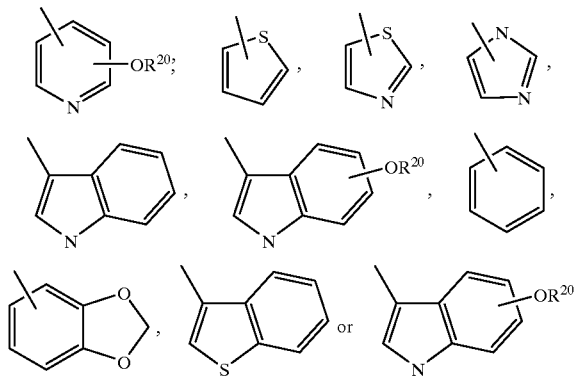

wherein R$^{20}$ is hydrogen or $C_1$–$C_6$ alkyl.

The term "O-aryl" refers to an aryloxy or an aryl group bonded to an oxy moiety.

As used herein, the term "TBS" refers to tert-butyldimethylsilyl represented by the formula:

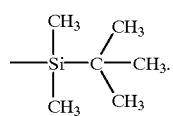

As used herein, the term "NHS" refers to N-hydroxysuccinimide represented by the formula:

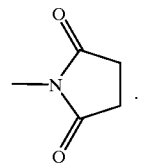

As used herein the term "Ph" refers to a phenyl moiety.

As used herein the term "base labile amino protecting group" refers to common amino protecting groups which are known to be base labile. The artisan can consult common works such as Greene, T. W. "Protecting Groups in Organic Synthesis", Wiley (New York, 1981). See particularly Chapter 7 of Greene. An especially preferred base labile amino protecting group is fluorenylmethoxycarbonyl (Fmoc).

The term "suitable activatable carboxy protecting group" refers to carboxy protecting groups containing activatable ester substituents and are known by one of ordinary skill in the art and disclosed by Greene, T. W., supra. Suitable carboxy protecting groups are those which are activatable ester substituents including N-hydroxy-succinimide, N-hydroxysulfosuccinimide and salts thereof, 2-nitrophenyl, 4-nitrophenyl, 2,4-dichlorophenyl, and the like. An especially preferred activatable carboxy protecting group is N-hydroxy-succinimide (NHS).

As used herein, the term "cryptophycin compound" refers to a compound of the formula:

(II)

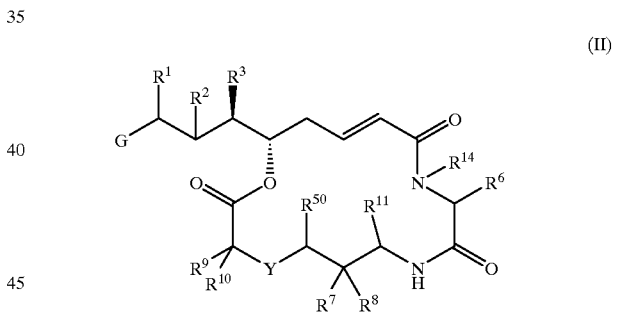

wherein

G and R$^3$ are as defined in formula (I);

R$^1$ is halogen and R$^2$ is OH or glycinate ester; or R$^1$ and R$^2$ may be taken together to form an epoxide ring; or R$^1$ and R$^2$ may be taken together to form a bond;

R$^7$ and R$^8$ are each independently hydrogen or $C_1$–$C_6$ alkyl; or

R$^7$ and R$^8$ taken together form a cyclopropyl or cyclobutyl ring;

R$^9$ is hydrogen, $C_1$–$C_6$ alkyl, $C_2$–$C_6$ alkenyl, $C_2$–$C_6$ alkynyl, —(CH$_2$)$_m$—($C_3$–$C_5$)cycloalkyl or benzyl, wherein m is the integer one to three;

R$^{10}$ is hydrogen or $C_1$–$C_6$ alkyl;

R$^{11}$ is hydrogen, $C_1$–$C_6$ alkyl, phenyl or benzyl;

R$^{14}$ is hydrogen or $C_1$–$C_6$ alkyl;

R$^{50}$ is hydrogen or (=O);

Y is CH, O NR$^{12}$, S, SO, SO$_2$, wherein R$^{12}$ is H or C$_1$–C$_3$ alkyl;

R$^6$ is C$_1$–C$_6$ alkyl, substituted (C$_1$–C$_6$)alkyl, (C$_3$–C$_8$) cycloalkyl, substituted (C$_3$–C$_8$)cycloalkyl, a heteroaromatic or substituted heteroaromatic group or a group of formula (IA), (IB) or (IC):

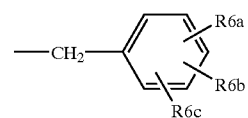

(IA)

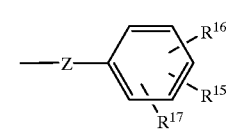

(IB)

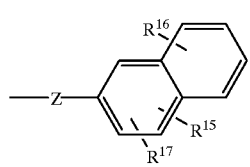

(IC)

R$^{6a}$, R$^{6b}$, and R$^{6c}$ independently are H, (C$_1$–C$_6$)alkyl, halo NR$^{18}$R$^{19}$ or OR$^{18}$;

R$^{15}$, R$^{16}$, and R$^{17}$ independently are hydrogen, halo, (C$_1$–C$_6$)alkyl, OR$^{18}$, O-aryl, NH$_2$, NR$^{18}$R$^{19}$, NO$_2$, OPO$_4$H$_2$, (C$_1$–C$_6$ alkoxy)phenyl, S-benzyl, CONH$_2$, CO$_2$H, PO$_3$H$_2$, SO$_2$R$^{23}$, or Z';

R$^{18}$ and R$^{19}$ independently are hydrogen or C$_1$–C$_6$ alkyl;

R$^{23}$ is hydrogen or (C$_1$–C$_3$)alkyl;

Z is —(CH$_2$)$_n$— or (C$_3$–C$_5$)cycloalkyl;

n is 0, 1, or 2; and

Z' is an aromatic or substituted aromatic group; or a pharmaceutically acceptable salt thereof.

As used herein, the term "Cryptophycin 52" represents the compound of the formula:

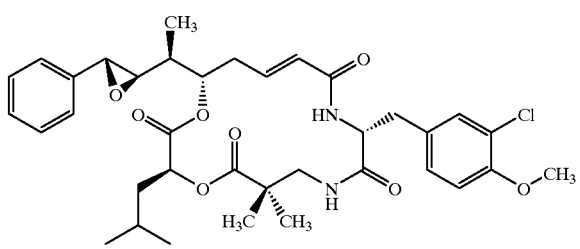

A general synthetic procedure for preparing a compound of formula (I) is set forth in Scheme A. In Scheme A, all substituents unless otherwise indicated, are as previously defined. Reagents, techniques, and procedures used in Scheme A are well known and appreciated by one of ordinary skill in the art.

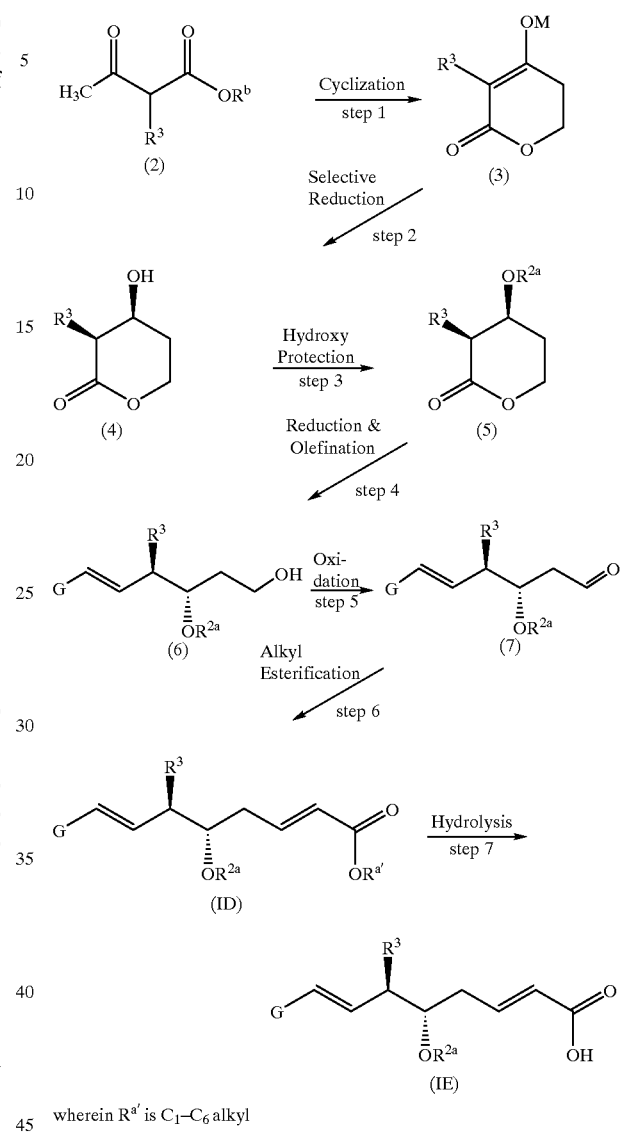

SCHEME A wherein R$^{a'}$ is C$_1$–C$_6$ alkyl

In Scheme A, step 1, the acylacetate of formula (2) is cyclized with a suitable cyclizing agent to form a lactone of formula (3).

A suitable cyclizing agent is any agent capable of converting the acylacetate of formula (2) to the lactone of formula (3).

For example, an acylacetate of formula (2) is added to a solution of a suitable base, such as potassium t-butoxide, lithium dialkylamides, for example, lithium diisopropylamide, sodium hydride and the like. Most preferred is potassium t-butoxide. The suitable base is dissolved in suitable organic solvent, for example, alcoholic solvents, such as methanol, ethanol, 2-propanol, or mixtures thereof; tetrahydrofuran, and the like. Most preferred are alcoholic solvents, such as 2-propanol. The amount of suitable base to be dissolved ranges from about 1.0 molar equivalents to about 2.0 molar equivalents as compared to the acylacetate of formula (2). Preferably, the amount of suitable base ranges from about 1.3 to about 1.7 molar equivalents. Most preferably, the amount of suitable base ranges from about 1.4 to about 1.6 molar equivalents. The basic solution is set to a temperature ranging from about −30° C. to about 30° C., preferably under an inert atmosphere, such as nitrogen, in preparation for the reaction with the desired acylacetate of formula (2). Most preferably, the solution is cooled to about 0° C.

The acylacetate of formula (2) is added to the basic solution at a rate so as to maintain the temperature at or below +10° C. Preferably, the acylacetate of formula (II) is added so as to maintain the temperature between −5° C. and +7° C. Most preferably, the acylacetate of formula (II) is added so as to maintain the temperature between 0° C. and +5° C.

The acylacetate basic solution is then reacted with a suitable aldehyde or ketone of formula (2b'), which corresponds to the compound of formula (2b) wherein $R^{2b}$ is hydrogen. The amount of aldehyde or ketone of formula (2b') to be added ranges from about 1.0 molar equivalents to about 3.0 molar equivalents as compared to the acylacetate of formula (2). Preferably, the amount of suitable base ranges from about 1.1 to about 2.2 molar equivalents. Most preferably, the amount of suitable base ranges from about 1.2 to about 1.5 molar equivalents. Generally, the aldehyde or ketone of formula (2b') is reacted with the acylacetate solution at a temperature ranging from about 0° C. to about 50° C. Most preferably, the reaction is carried out at room temperature.

The resulting mixture is then acidified with a suitable acid, such as hydrochloric acid. The acidified mixture is then isolated and purified according to methods appreciated by one of ordinary skill in the art, such as extraction, evaporation, filtration and recrystallization to provide the lactone of formula (3).

The acylacetates of formula (2) are known or readily prepared by one of ordinary skill in the art. Examples include ethyl 2-methylacetoacetate, ethyl 2-n-hexylacetoacetate, ethyl 2-ethylacetoacetate, ethyl 2-n-propylacetoacetate, ethyl 2-isopropylacetoacetate, and the like.

The preferred aldehydes or ketones of formula (2b') include paraformaldehyde, acetaldehyde, acetone, and the like.

In Scheme A, step 2, the lactone of formula (3) is contacted with a stereoselective reducing agent to provide the stereoselectively reduced compound of formula (4).

The stereoselective reducing agent used in Scheme A, step 2 may be either chemical, or preferably biological. In the case of biological agents, the preferred agents are microorganisms which contain reducing enzymes, more preferred microorganisms of genus Mortierella. Particular preference is given to the species: *Mortierella isabellina, Mortierella alpina, Mortierella pusilla, Mortierella nana, Mortierella vinacea,* and *Mortierella ovata*. Most preferably, the microorganism is *Mortierella isabellina* ATCC 42613. Other suitable biological agents for this process include the genera: Pichia, Saccharomyces, Candida, Kluyveromyces, Zygosaccharomyces, Pichia, Aureobasidium, Torulopsis, Trigonopsis, Kloeckeva, Hanseniaspora, Schizosaccharomyces, Cryptococcus, Rhodotorula, Geotrichum, Rhizopus and Cumminghamella. Selected species of these genera were tested for the preparation of formula (4) and did not provide significant yield under the conditions tried: *Zygosaccharomyces rouxii* ATCC 14462, *Candida guillermondi* ATCC 2479, *Pichia fermentens* ATCC 10651, *Nematospora coryli* NRRL Y-1343, *Candida famata* ATCC 26418, *Saccharomyces pastorianus* ATCC 2366 , *Saccharomyces uvarum* ATCC e9080, *Candida utilis* ATCC 9950, *Saccharomyces globosus* ATCC 10600, *Kluyveromyces dobzhanskii* NRRL-Y-1974, *Kluyveromyces lactis* QM 8230, *Aureobasidium pullulans* QM 2725, *Kloeckeva javanica* ATCC 10636, *Hanseniaspora valbyensis* ATCC 10631, *Octosporomyces octosporus* ATCC 10631, *Candida parapsilosis* ATCC 22019, *Candida tropicalis* ATCC 12659, *Torulopsis taboadae* ATCC 42213, *Torulopsis ethanolitolerans* ATCC 46859, *Torulopsis ethanolitolerans* ATCC 46859, *Torulopsis ptarmiganii* ATCC 26902, *Torulopsis sonorensis* ATCC 56511, *Trigonopsis variabilis* ATCC 10679, *Torulopsis enokii* ATCC 20432, *Candida boidinii* ATCC 18810, *Candida blankii* ATCC 18735, *Cryptococcus laurentii* ATCC 42922, *Hansenula polymorpha* ATCC 34438, *Rhodotorula mucilaginosa* A35210, *Kluyveromyces marxianus* ATCC 8554, *Saccharomyces bayanus* ATCC 76516, *Sporobolomyces salmonicolor* ATCC 26697, *Cryptococcus laurentii* ATCC 36833, *Arthroascus javanensis* NRRL Y1493, *Hyphopicia burtonii* NRRL Y1988, *Saccharomycopsis capularis* NRRL Y50, *Yarrowia lipolytica* NRRL YB423-3, *Guillermondella selenospora* NRRL Y1357, *Saccharomycopsis fibuligera* NRRL Y3, *Lipomyces tetrasporus* NRRL 7074, *Pachysolen tannophilus* NRRL 2460, *Geotrichum candidum* ATCC 7471 or ATCC 14253, *Ambrosiozyma monospora* ATCC 14628, *Chinosphaera apobasidialis* ATCC 52639, *Phaffia rhodozyma* ATCC 24202, *Debaryomyces polymorphus* ATCC 20499, *Endomycopsella vini* ATCC 34382, *Schizosaccharomyces pombe* ATCC 26189, *Schwanniomyces occindentalis* ATCC 26077, *Bensingtonia yuccicola* ATCC 66429, *Rhizopus oryzae* ATCC 9363, *Rhizopus stolonifer* A33417, *Mortierella ramanniana* ATCC 38191, *Mortierella verticillata* NRRL 6337, *Mortierella chlamydospora* NRRL 2769, *Mortierella multidivaricata* ATCC 58767, *Mortierella sepedonioides* NRRL 6425, *Mortierella elongata* NRRL 5513, Mortierella sp. NRRL 1458, *Mortierella hyalina* NRRL 6427, *Mortierella pulchella* ATCC 18078, *Mortierella bisporalis* NRRL 2493, *Mortierella sclerotiella* ATCC 18732, *Mortierella minutissima* ATCC 16268, *Mortierella spinosa* ATCC 16272 *Penicillium glabrum* ATCC 11080, *Emericella quadrilineata* ATCC 12067, *Syncephalastrum racemosum* ATCC 20471, Geotrichum sp. ATCC 32345, *Aspergillus niveus* ATCC 20922, *Aspergillus niger* ATCC 64958, *Cunninghamella echinulata* var.*echinulata* ATCC 36190, *Mucor circinelloides f.circinelloides* ATCC 15242, *Penicillum purpurogenum* ATCC 9777, *Beauveria bassiana* ATCC 9835, *Nocardia salmonicolor* ATCC 19149, *Rhizopus nigricaus* ATCC 6227b, *Mortierella epigama* ATCC 2402, and *Mortierella schmuckeri* ATCC 42658.

*Zygosaccharomyces rouxii* ATCC 14462 and *Candida guillermondi* ATCC 2479, gave indication on GC that they produced the hydroxylactone from the ketone. However, significant ketone remained indicating that conversion was poor compared to Mortierella under the conditions tested.

For example, a suitable microorganism, such as *Mortierella isabellina* ATCC 42613 may be used in free state as wet cells, freeze-dried cells or heat-dried cells. Immobilized cells on support by physical adsorption or entrapment can also be used. Appropriate media for growing microorganisms for this process typically include necessary carbon sources, nitrogen sources, and trace elements. Inducers may also be added. As used herein, the term "inducer" refers to any compounds having keto or aldehyde groups, such as paraformaldehyde and the like.

Carbon sources include sugars such as maltose, lactose, dextrose, glucose, fructose, glycerol, sorbitol, sucrose, starch, mannitol, propylene glycol, and the like; organic acids such as sodium acetate, sodium citrate, and the like;

amino acids such as sodium glutamate and the like; alcohols such as ethanol, propanol, and the like.

Nitrogen sources include N-Z amine A, corn steep liquor, soy bean meal, beef extracts, yeast extracts, molasses, baker's yeast, tryptone, nutrisoy, peptone, yeastamine, sodium nitrate, ammoonium sulfate, and the like.

Trace elements include phosphates, magnesium, manganese, calcium, cobalt, nickel, iron, sodium, and potassium salts.

For the purposes of this invention, appropriate media may include more than one carbon or nitrogen source and may include a mixture of several.

After sterilization the pH of the medium should be adjusted to 4.5 to 6.5, preferably 5.5. The pH may be maintained between about 4.0 and 6.0, preferably at 5.5 during the fermentation and 4.5 during the bioreduction.

The temperature of the reaction mixture should be maintained to ensure that there is sufficient energy available for the process. The temperature is a measure of the heat energy available for the transformation process. A suitable temperature of reaction ranges from about 20° C. to 35° C. A preferred temperature range is from about 25° C. to about 30° C.

The agitation and aeration of the reaction mixture affects the amount of oxygen available during the fermentation and bioreduction stages of the process. During both stages the agitation range from 150 to 450 rpm is preferable, with 150 to 275 rpm being most preferred. Aeration of about 0.5 to 3.5 standard cubic feet per minute (scfm) is preferable, with 0.5 to 1.0 scfm being most preferred.

The reaction time for the reduction of Scheme A, step 2 ranges from about 24 to 96 hours, preferably 24 to 48 hours, measured from the time of initially treating the substrate (3) with the microorganism to provide the lactone of formula (4).

In Scheme A, step 3, the lactone of formula (4) is reacted with a hydroxy protecting agent to yield the protected lactone of formula (5).

A suitable hydroxy protecting agent includes compounds of the formula $R^{2a}$-LG where $R^{2a}$ is trityl or a silyl protecting group, preferably tri($C_1$–$C_6$ alkyl)silyl, and LG is a suitable leaving group, such as a halogen or a sulfonate, such as trifluoromethanesulfonate. Specific examples of hydroxy protecting agents include t-butyldimethylsilyl chloride, t-butyldimethylsilyl trifluoromethane sulfonate, chlorotrimethylsilane and the like.

For example, the lactone of formula (4) is contacted with a suitable base, most preferably imidazole, in a suitable organic solvent such as $CH_3CN$. A suitable hydroxy protecting agent, such as t-butyldimethylsilyl chloride, is then added to the solution, optionally with a suitable coupling catalyst such as dimethylaminopyridine. The mixture is then stirred at a temperature of from about 0° C. to about 60° C., preferably room temperature, for a period of time ranging from about 2 to 24 hours. The protected alcohol of formula (5) can be isolated by techniques well known in the art, such as extraction, evaporation, and precipitation. The product can be purified by chromatography and recrystallization.

In Scheme A, step 4, the protected alcohol of formula (5) is reacted with a reducing agent followed by an olefinating agent to provide the olefin of formula (6).

A suitable reducing agent includes alkylated aluminum hydrides and other reagents that would convert the protected lactone of formula (5) into a lactol and/or open chained hydroxyaldehyde intermediate. Examples include diisobutylaluminum hydride, bis(dialkylamino)aluminum hydride, either preformed or generated in situ from alkali-aluminum compounds such as $LiAlH_4$, $NaAlH_4$, $NaH_2Al(C_1$–$C_6$ alkyl)$_2$, $NaH_2Al(OCH_2CH_2OMe)_2$ $LiHAl(OtBu)_2$ and the like, in combination with dialkyl or cyclic amines such as dimethylamine, diethylamine, dipropylamine, morpholine, piperidine and the like.

A suitable olefinating agent includes aryl Wittig reagents, aryl Horner-Emmons Wadsworth reagents and other reagents that are known by one of ordinary skill in the art to convert aldehydes to olefins in either a one-step or stepwise fashion. Examples include benzyldiphenylphosphine oxide (BDPPO), triphenyl benzyl phosphonium chloride and the like. The synthesis of suitable olefinating agents are known in the art. For example, the synthesis of BDPPO is described by Brown, *Tetrahedron Lett.* 35 (36), 6733 (1994).

For example, the protected lactone of formula (5) is reacted with a suitable reducing agent such as DIBAL or DIBAH under an inert atmosphere, for a period ranging from about 0.5 to 12 hours. The reaction is carried out in the presence of a suitable organic solvent, such as methylene chloride or hexane while the temperature is maintained below –10° C. to form portion A. In a separate reaction vessel a suitable olefinating agent, such as BDPPO or triphenyl benzyl phosphonium chloride is contacted with a suitable base, such as sodium bis(trimethylsilyl)amide or potassium tert-butoxide in the presence of a suitable organic solvent such as tetrahydrofuran (THF) or methylene chloride. The solution may be stirred at room temperature for a period of time ranging from about 10 minutes to 2 hours. The resulting reddish solution is then contacted with portion A and stirred for 1 to 36 hours at a temperature ranging from about 0° C. to about 70° C. The olefin of formula (6) may be isolated by techniques well known in the art, such as extraction, evaporation, and precipitation. The product can be purified by chromatography and recrystallization.

In Scheme A, step 5, the olefin of formula (6) is oxidized with an oxidizing agent to provide the aldehyde of formula (7).

An oxidizing agent is a reagent capable of converting the hydroxy moiety on the olefin of formula (6) to aldehyde moiety of formula (7). Suitable oxidizing agents include oxalyl chloride/DMSO, TEMPO/NaOCl, $P_2O_5$/DMSO, $(COCl)_2$/DMSO, NBS/TEMPO, and the like.

For example, anhydrous dimethylsulfoxide (DMSO) is added to oxalyl chloride in a suitable organic solvent, such as methylene chloride over a period of time ranging from about 1 to about 30 minutes at a temperature ranging from about –30° C. to about –78° C., preferably about –60° C. The mixture is then stirred for a period of time ranging from about 10 minutes to 2 hours after which a solution of olefin for formula (6) in a suitable organic solvent, such as methylene chloride is added. After additional stirring for a period ranging from 5 to 30 minutes, a suitable base, such as triethylamine is added and the reaction is allowed to warm to room temperature. The aldehyde of formula (7) may be isolated by techniques well known in the art, such as extraction, evaporation, and precipitation. The product can be purified by chromatography and recrystallization.

In Scheme A, step 6, the aldehyde of formula (7) is reacted with an alkyl ester forming agent to form the ester of formula (ID).

An alkyl ester forming agent is any agent capable of converting the aldehyde moiety of the compound formula (7) to the alkyl ester moiety of the compound of formula (ID), while inert to the other substituents on the molecules. For example, the aldehyde of formula (7) may be converted to the ester of formula (ID) by means of a Horner-Emmons reaction. Suitable examples of alkyl ester forming agents include trimethyl phosphonoacetate, $(CH_3O)_2POCH_2CH_3$ and the like.

For example, the aldehyde of formula (7) is contacted with an alkyl ester forming agent, such as trimethylphosphonoacetate, and tetramethylguanidine in a suitable organic solvent, such as tetrahydrofuran at ambient temperature and stirred for a period ranging from about 1 to about 24 hours. The ester of formula (ID) may be isolated by techniques well known in the art, such as extraction, evaporation, and precipitation. The product can be purified by techniques well known in the art, such as chromatography.

In Scheme A, step 7, the ester of formula (ID) is reacted with a hydrolyzing agent to provide the acid of formula (IE).

A hydrolyzing agent is any agent that is capable of converting the ester moiety of the compound of formula (IA) to the acid moiety of the compound of formula (IB), while inert to the other substituents on the molecules. Examples of suitable hydrolyzing agents include inorganic bases such as sodium hydroxide and potassium hydroxide, with potassium hydroxide being preferred.

For example, the ester of formula (IA) is contacted with a suitable hydrolyzing agent, such as 2N KOH in a suitable organic solvent, such as 1,4-dioxane at ambient temperature. The solution is then heated to reflux for a period of time ranging from about 1 to about 6 hours. The reaction is then quenched with a suitable acid, such as 2N HCl. The acid of formula (IB) is isolated by techniques well known in the art, such as extraction, evaporation, and precipitation. The product can be purified by techniques well known in the art, such as chromatography.

General synthetic procedures for preparing cryptophycin compounds of formula (II) are set forth in Barrow, R. A. et al., *J. Am. Chem. Soc.* 117, 2479 (1995); PCT Intnl. Publ. No. WO 96/40184, published Dec. 19, 1996; PCT Intnl. Publ. No. WO 98/08505, published Mar. 5, 1998; PCT Intnl. Publ. No. WO 97/07798, published Mar. 6, 1998; PCT Intnl. Publ. No. WO 97/23211, published Jul. 3, 1997; PCT Intnl. Publ. No. WO 98/08506, published Mar. 5, 1998; PCT Intnl. Publ. No. WO 98/08812, published Mar. 5, 1998; and PCT Intnl. Publ. No. WO 97/31632, published Sep. 4, 1997. References disclosing intermediates and/or processes for preparing cryptophycin compounds of formula (II) or intermediates thereof include PCT Intnl. Publ. No. WO 98/09955, published Mar. 12, 1998; PCT Intnl. Publ. No. WO 98/09974, published Mar. 12, 1998; PCT Intnl. Publ. No. WO 98/09601, published Mar. 12, 1998; and PCT Intnl. Publ. No. WO 98/09988, published Mar. 12, 1998.

Scheme B illustrates a general synthetic procedure for preparing a cryptophycin compound of formula (II). In Scheme B, all substituents unless otherwise indicated, are as previously defined. As used herein, $R^p$ is hydrogen or a suitable activatable carboxy protecting group; $R^{p1}$ is hydrogen or $C_1$–$C_6$ alkyl; $R^{81}$ is $C_1$–$C_6$ alkyl, $C_3$–$C_8$ cycloalkyl, phenyl or benzyl; $R^{82}$ is a base labile protecting group; Hal is halogen, preferably chloro, bromo or iodo; and q is an integer 1 or 2.

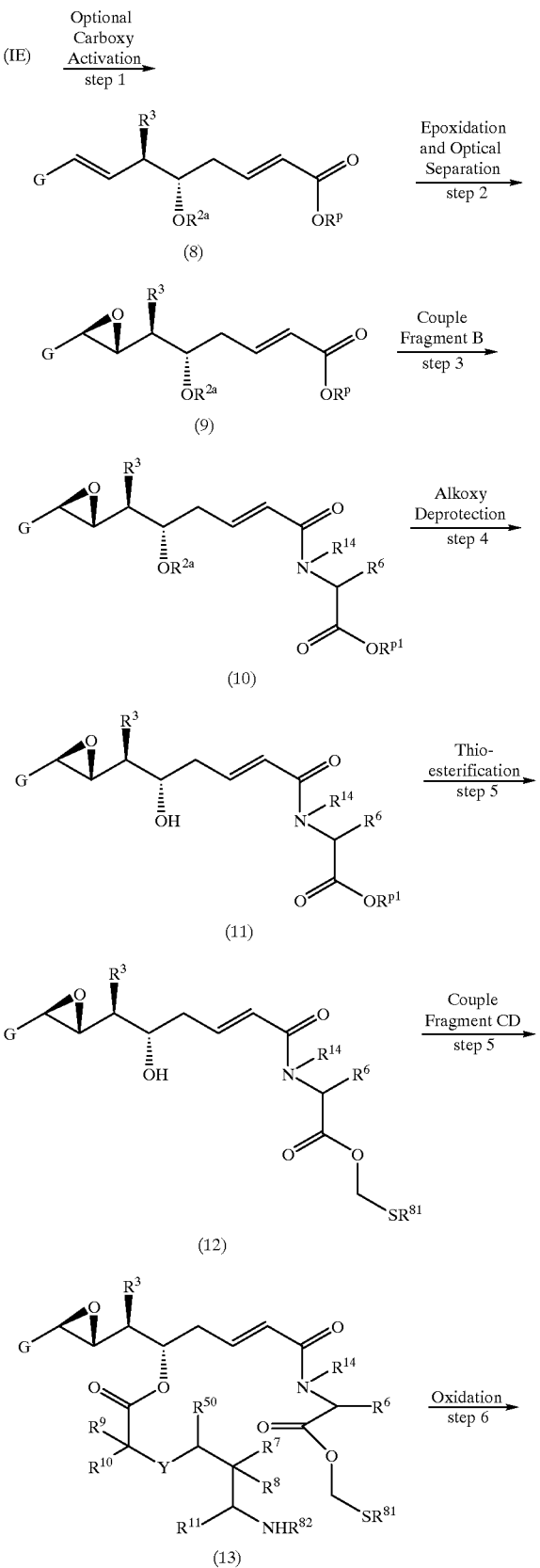

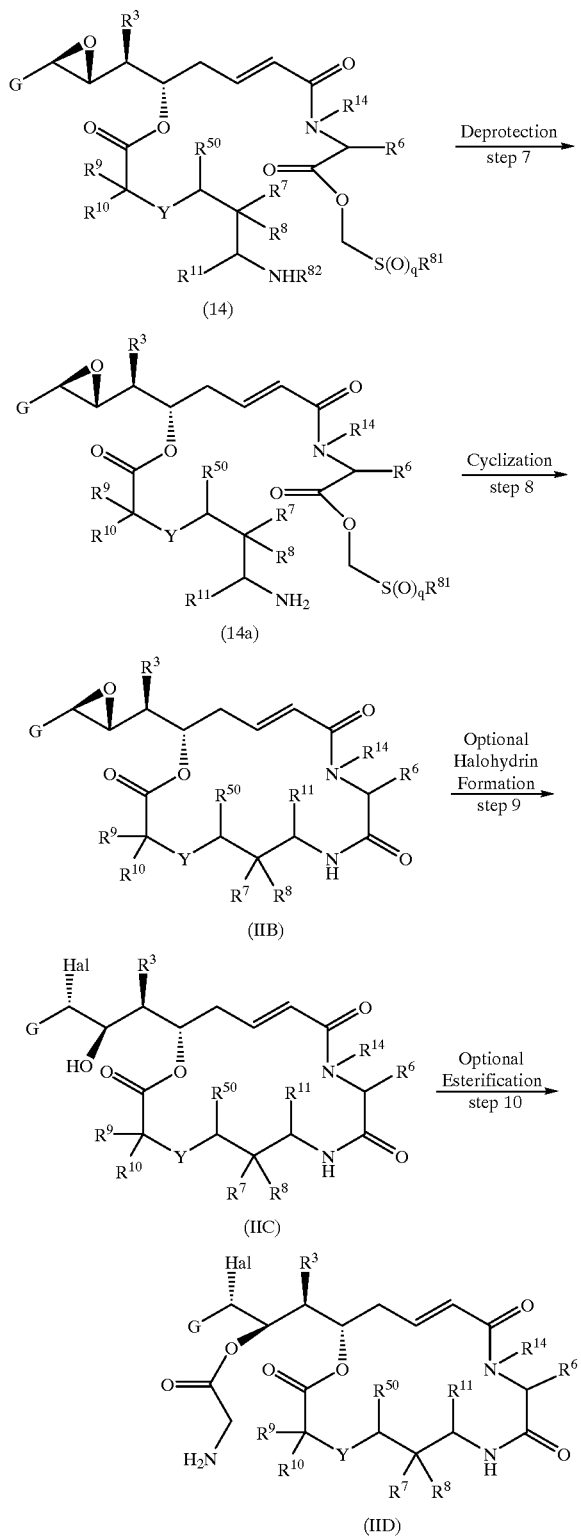

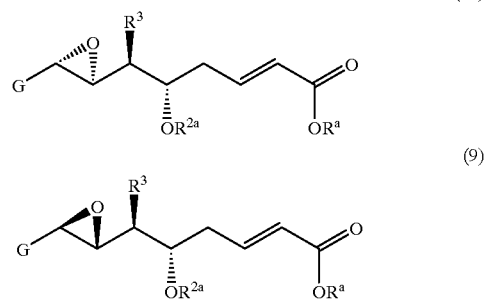

In Scheme B, step 1, a compound of formula (IE) is optionally treated with a carboxy activating agent to provide the activatable ester of formula (8).

For example, a compound of formula (IE) is reacted with a suitable coupling agent, such as a carbodiimide, for example, 1-ethyl-3-(3-dimethylaminopropyl)carbodiimide, and a suitable carboxy activating agent, such as N-hydroxysuccinimide, in a suitable organic solvent, such as dry dimethylformamide. The mixture is stirred for a period of time ranging from about 6 to 36 hours at a temperature ranging from about 10° C. to about 50° C. The activatable ester of formula (8) is isolated by techniques well known in the art, such as extraction, evaporation, and precipitation. The product can be purified by techniques well known in the art, such as chromatography.

In Scheme B, step 2, an activatable ester of formula (8) is epoxidized with an epoxidizing agent to form an epoxide of formula (9).

The compound of activatable ester of formula (8) may be epoxidized non-selectively using a suitable epoxidizing agent. An "epoxidizing agent" is an agent capable of converting the activatable ester of formula (8) into the epoxide of compound (9). Suitable epoxidizing agents include potassium peroxomonosulfate (oxone) in combination with acetone, m-CPBA, methyltrioxorhenium(VII), trifluoroperacetic acid, and magnesium monoperoxyphthalate, with Oxone in combination with acetone, or m-CPBA being preferred. Possible solvents for the epoxidation activatable ester of formula (8) include acetone, DMF, glyme, dioxane, $CH_3CN$, alcohols, THF, EtOAc, halohydrocarbons, chlorobenzene, dichloromethane and toluene. The reaction optionally takes place in the presence of a suitable base such as $NaHCO_3$. Reaction temperatures may range from about −30° C. to about 50° C. with about −10° C. to about 25° C. being preferred. The β-epoxide of formula (9) may be isolated and purified according to techniques and procedures well known in the art such as column chromatography. Either the α- and β-epoxides of formula (9) may be further separated by HPLC. It is preferred that the β-epoxide of formula (9), is separated from the α-epoxide of formula (9a), and further used in the remaining steps of the process of this invention to form a the β-epoxy form of a compound of formula (I). However, the epoxidizing reaction of Scheme B, step 1 can also be used with the α-epoxide of formula (9a) or with a mixture of the two epoxides.

The compound of formula (I) wherein $R^a$ is H may be epoxidized directly using m-CPBA. The m-CPBA epoxidation may be carried out on a compound of formula (I) to give a 1.2:1 b/a diastereomeric mixture of epoxides. The individual α- and β-diastereomers may be separated by HPLC, as described above. This direct epoxidation is illustrated in Scheme B1.

SCHEME B1

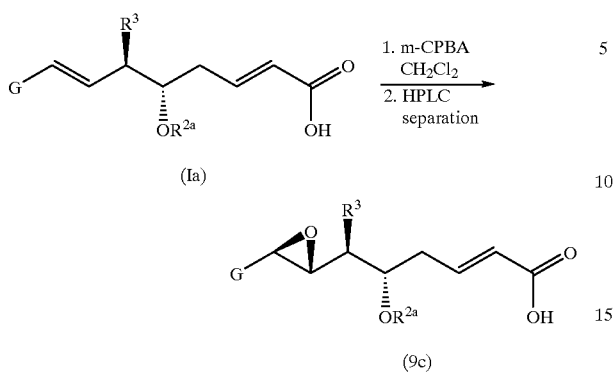

By eliminating the use of the N-hydroxysuccinimide ester, one step is eliminated from the synthesis.

Furthermore, a compound of formula (9e) may be prepared by deesterifying a compound (9d) according to Scheme B2. In Scheme B2, $R^a$ is $C_1$–$C_6$ alkyl whereas all of the remaining substituents are as previously defined.

SCHEME B2

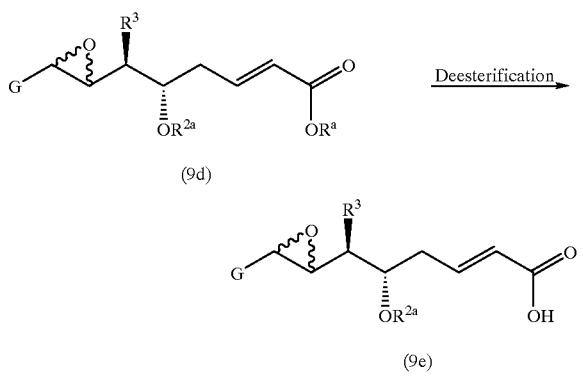

In Scheme B2, the alkyl ester of formula (9d) is deesterified with a suitable deesterifying agent to form the acid of formula (9e). The term "suitable deesterifying agent" encompasses any suitable means or conditions for removing the ester moiety of $R^a$ while inert to the epoxide. For example, a suitable base, such as potassium hydroxide, is added to a solution of the alkyl ester of formula (9d) in a suitable solvent, such as tetrahydrofuran. The biphasic mixture is then allowed to stir at a temperature ranging from about 20° C. to about 80° C., preferably 40° C. and 65° C., for a period of from about 6 to 24 hours. After cooling to room temperature, the aqueous layer is washed with an appropriate acid, such as 1N hydrochloric acid, followed by brine. The mixture is dried, filtered and concentrated to provide the acid of (9e).

A compound of formula (I) or formula (8) may also be stereoselectively epoxidized to form either the compound of formula (9) or (9a) using a chiral ketone with Oxone in the presence of a suitable base such as $NaHCO_3$ based on procedures analogous to those disclosed by Tu, Y. et al, *J. Am. Chem. Soc.* 118, 9806 (1996); Wang, Z-X et al. *J. Org. Chem.* 62, 2328 (1997); Wang, Z-X et al., *J. Am. Chem. Soc.* 119, 11224 (1997). Preferred compounds of formula (8) for this reaction include those compounds where G is phenyl, $R^3$ is methyl, and R is NHS (N-hydroxysuccinimide). As used herein, the term "chiral ketone" refers to a ketone containing the following general features:

1) the stereogenic centers are close to the reacting center; and
2) the ketone has a fused ring and a quaternary center adjacent to a carbonyl group; and
3) one face of the ketone is sterically blocked.

One especially preferred chiral ketone is of the structure:

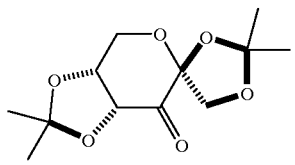

This preferred chiral ketone can be prepared from D-fructose by ketalization and oxidation under routine conditions. For example, the ketalization can be completed using acetone, $HClO_4$, and the process is conducted at about 0° C. For example, the oxidation can be completed using pyridinium chlorochromate at room temperature. These reactions are known in the art; see, for example: Tu, Y. et al, supra. and Wang, Z-X et al. supra. The asymmetric epoxidation can be carried out at a pH within the range of from about 7.0 to about 11.5 during the reaction.

Although it requires about 3–4 equivalents of chiral ketone to obtain conversions of greater than 95% with many cryptophycin intermediates at a pH of about 8.0, it is possible to use less chiral ketone (about 1–2 equivalents) at a pH of about 9.0 or above. Suitable solvents useful for the epoxidation step include $H_2O$, DMF, glyme, dioxane, $CH_3CN$, alcohols, THF, EtOAc, halohydrocarbons, chlorobenzene, and toluene, with a $CH_3CN/H_2O$ solvent combination being preferred. Reaction temperatures may range from about –20° C. to about 25° C. with about –10° C. to about 10° C. being preferred. The individual isomers, (9) or (9a), can be isolated from the crude mixture of isomers and purified by techniques well known in the art such as extraction, evaporation, chromatography and recrystallization. A preferred stereoselective epoxidation utilizes the chiral ketone of structure (9f) to provide a mixture of epoxides in the crude product in the ratio of about α:β 1:5.

The β-epoxide of formula (9) is generally preferred and is used throughout the process of this invention.

In Scheme B, step 3, the epoxide of formula (9) is coupled to the amino acid of formula:

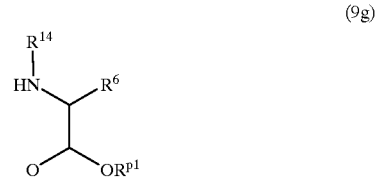

wherein $R^6$ and $R^{14}$ are as defined above and $R^{p1}$ is hydrogen or $C_1$–$C_6$ alkyl to yield a Fragment A-B compound of formula (10).

The amino acids of formula (9g) are commercially available or are readily prepared by methods known in the art. Particularly preferred amino acids of formula (9g) include those where $R^6$ is a group of formula (IA) and $R^{6a}$ is methoxy, $R^{6b}$ is chloro and $R^{6c}$ is H; $R^{14}$ is hydrogen; and $R^{p1}$ is hydrogen; said amino acids being disclosed by PCT Intnl. Publ. No. WO 97/07798, published Mar. 6, 1997, PCT Intnl. Publ. No. WO 96/40184, published Dec. 19, 1996; Barrow, R.A. et al. *J. Am. Chem. Soc.* 117, 2479 (1995).

The epoxide of formula (9), where $R^p$ is NHS, is coupled to the amino acid of formula (9g) according to coupling procedures which are inert to the epoxide functionality. For example, the epoxide of formula (9) is contacted with from about 1.5 to 3.5 equivalents of amino acid (9g), where $R^{p1}$ and $R^{14}$ are both hydrogen, and a suitable silylating agent in the presence of a suitable organic solvent. Suitable organic solvents include DMF, glyme, dioxane, $CH_3CN$, THF, EtOAc, and halohydrocarbons, such as methylene chloride. The reaction is carried out at a temperature ranging from about −30° C. to about 75° C., with a temperature ranging from about 20° C. to about 60° C. being preferred. The fragment A-B compound of formula (10) may be isolated and purified according to techniques and procedures well known in the art such as extraction, evaporation, chromatography and recrystallization.

As used herein, the term "silylating agent" is selected from any reagent capable of attaching a silyl group to a target substituent. Generally known silylating agents are employed. See for example, Calvin, E. W., "Silicon Reagents in Organic Synthesis", Academic Press, (London, 1988). Generally typical silyl agents include any reagent with a trialkylsilyl group such as trimethylsilyl, triethylsilyl, triisopropylsilyl, dimethylisopropylsilyl, diethylisopropylsilyl, dimethylthexylsilyl, and t-butyldimethylsilyl, any reagent with an alkylarylsilyl group such as tribenzylsilyl, diphenylmethylsilyl, t-butylmethoxyphenylsilyl and tri-p-xylylsilyl, and any reagent with a triarylsilyl group such as triphenylsilyl. The preferred silylating agent is a trimethyl silylating agent. Typical trimethyl silylating agents include N,O-Bis (trimethyl silyl) acetamide, allyltrimethylsilane, N,O-Bis (trimethylsilyl)-carbamate N,N-Bis(trimethylsilyl) methylamine, Bis(trimethylsilyl)sulfate, N,O-Bis (trimethylsilyl)trifluoroacetamide, N,N-Bis(trimethylsilyl) urea, (ethylthio)trimethylsilane, ethyl trimethyl silylacetate, hexamethyldisilane, hexamethyldisilazane, hexamethyldisiloxane, hexamethyldisilthiane, (isopropenyloxy)trimethyl silane, 1-methoxy-2-methyl-1-trimethyl-siloxy-propene, (methylthio)trimethylsilane, methyl 3-trimethylsiloxy-2-butenoate, N-methyl-N-trimethylsilylacetamide, methyl trimethylsilylacetate, N-methyl-N-trimethylsilyl-hepta-fluorobutyramide, N-methyl-N-trimethylsilyl-trifluoroacetamide, (phenylthio) trimethylsilane, trimethylbromosilane, trimethylchlorosilane, trimethyliodosilane, 4-trimethylsiloxy-3-penten-2-one, N-(trimethylsilyl) acetamide, trimethylsilyl acetate, trimethylsilyl azide, trimethylsilyl benzenesulfonate, trimethylsilyl cyanide, N-trimethylsilyldiethylamine, N-trimethylsilyldimethylamine, trimethylsilyl N,N-dimethylcarbamate, 1-(trimethylsilyl)imidazole, trimethylsilyl methanesulfonate, 4-(trimethylsilyl)morpholine, 3-trimethylsilyl-2-oxazolidinone, trimethylsilyl trichloroacetate, trimethylsilyl trifluoroacetate and trimethylsilyl trifluoromethane sulfonate. Particularly useful silylating agents include "tri-lower alkyl silyl" agents, the term of which contemplates triisopropylsilyl, trimethylsilyl and triethylsilyl, trimethylsilyl halides, silylated ureas such as bis(trimethylsilyl)urea (BSU) and silylated amides such as N,O-bis(trimethylsilyl)acetamide (BSA). Bis N,O-trimethyl silyl acetamide (BSA) is an especially preferred silylating agent.

Alternatively, the desired β-epoxide (9c) may be coupled with (9g), when $R^{p1}$ is hydrogen, using a suitable coupling agent, preferably diphenylphosphinic chloride, and a silyl agent to give fragment A-B (10). Suitable coupling agents are well known in the art, as described by Greene, T. W. "Protecting Groups in Organic Synthesis", Wiley (New York, 1981) and include N,O- diphenylphosphinic chloride, diphenyl chlorophosphate, DCC, EDCI, chloroformates, and 2-chloro-4,6-dimethoxy-1,3,5-triazine. Diphenylphosphinic chloride is a preferred coupling agent. The suitable organic solvents described above, preferably methylene chloride, may be used. This procedure allows for the elimination of the carboxy protection step and allows for the use of lower amounts of amino acid (9g).

In Scheme B, step 4, the fragment A-B compound of formula (10) is deprotected with a suitable alkoxy deprotecting agent to form a compound of formula (11).

A suitable alkoxy deprotecting agent is one that removes the hydroxy protecting group signified by the $R^{2a}$ substituent while inert to the epoxide moiety of the fragment A-B compound of formula (10). Preferred deprotecting agents include basic fluoride sources such as tetrabutylammonium fluoride, pyridinium fluoride, triethylammonium fluoride, cesium fluoride, and the like, with tetrabutylammonium fluoride being preferred. The deprotection reaction takes place in the presence of a suitable organic solvent such as tetrahydrofuran, optionally in the presence of a suitable base, such as sodium bicarbonate ($NaHCO_3$). The reaction takes place in the range of from about 0° C. to about 80° C. with from about 20° C. to about 70° C. being preferred. The reaction is run for a period of time ranging from about 3 to 24 hours. Crude product (11) may be used without further purification. Alternatively, the compound of formula (11) may be isolated and purified according to procedures well known well known in the art such as extraction, evaporation, chromatography and recrystallization.

When $R^{p1}$ for the compound of formula (11) is hydrogen, the $R^{p1}$ moiety is actually the cationic salt of deprotecting agent, for example, cesium, tetrabutylammonium, and the like.

In Scheme B, step 5, the compound of formula (11) is contacted with a thioester forming agent to provide the ester of formula (12).

The term "thioester forming agent" encompasses any suitable means or conditions for forming the thioester moiety of formula (12). Included within this definition are the conditions set forth and/or analogously described in Ono, N. et al., *Bull. Chem. Soc. Jpn.* 51 (8), 2401 (1978); Ho, Tse-Lok, *Synth. Comm.* 9(4), 267–270 (1979); Narasaka, K. et al., *J. Am. Chem. Soc.* 106 (10), 2954–2960 (1984); L. G. Wade, Jr. et al., *Tetrahedron Lett.* 731–732 (1978); Mora, N. et al., *Tetrahedron Lett.* 34 (15), 2461–2464 (1993); and Dossena, A. et al. *J. Chem. Soc. Perkin Trans. I,* 2737 (1981).

For example, the compound of formula (11) may be treated with a sterically hindered alkyl halide, such as tert-butylbromide, and a solvent of the formula ($R^{81}$) (Me) SO, wherein $R^{81}$ is $C_1$–$C_6$ alkyl, $C_3$–$C_8$ cycloalkyl, phenyl or benzyl, in the presence of a suitable base, such as sodium bicarbonate ($NaHCO_3$). A preferred solvent for reaction is dimethylsulfoxide (DMSO). Both the sterically hindered alkyl halide and the suitable base are added in a molar excess of about 7.0 to 12.0 in comparison to the compound of formula (11). The reaction takes place in the range of from about 0° C. to about 60° C. with from about 10° C. to about 30° C. being preferred. The reaction is run for a period of time ranging from about 1 to 24 hours. Crude product (12) may be used without further purification. Alternatively, the ester of formula (12) may be isolated and purified according to procedures well known in the art such as extraction, evaporation, chromatography and recrystallization.

In those instances when the substituent $R^{p1}$ is a moiety other than hydrogen, the compound of formula (11) must first be carboxy-deprotected. Carboxy-deprotections under basic conditions are known by those of ordinary skill in the art. For example, the compound of formula (11) may be treated with a suitable base, such as lithium hydroxide (LiOH) for a period of time sufficient to remove the carboxy protecting group, for example from about 1 to 24 hours.

In Scheme B, step 6, the ester of formula (12) is coupled with a Fragment CD carboxylic acid of formula:

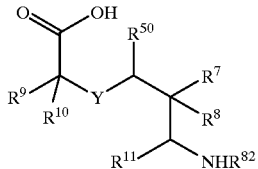

(12a)

wherein Y, $R^7$, $R^8$, $R^9$, $R^{10}$, $R^{11}$ and $R^{50}$ are as defined above and $R^{82}$ is a base labile protecting group; to provide the compound of formula (13).

For example, the carboxylic acid of formula (12a) is dissolved in a suitable organic solvent, such as DMF, glyme, dioxane, THF, $CH_3CN$, EtOAc, and halohydrocarbons, with dichloromethane being preferred. This solution is then treated with a coupling reagent. Possible coupling reagents include DCC, EDCI, and similar reagents, such as DMAP which activate carboxylic acids towards esterification with alcohols. This solution may then be optionally treated with a suitable base such as solid sodium bicarbonate and then contacted with an ester of formula (12). The concentration of (12a) after these additions should range from about 0.1 M to about 2.0 M. The reaction takes place in the range of from about −30° C. to about 60° C. with from about 10° C. to about 30° C. being preferred. The reaction is run for a period of time ranging from about 0.5 to 12 hours. The final concentration of crude product (13) may be used without further purification. Alternatively, the compound of formula (13) may be isolated and purified according to procedures well known in the art such as extraction, evaporation, chromatography and recrystallization.

In Scheme B, step 7, the compound of formula (13) is oxidized with a suitable oxidizing agent to provide the sulfone or sulfoxide of formula (14).

A suitable oxidizing agent is an agent capable of converting the sulfide of formula (13) into the sulfone of formula (14), while inert to the epoxide moiety of the molecule. Suitable oxidizing agents include potassium peroxomonosulfate (Oxone), m-CPBA, methyltrioxorhenium(VII), and magnesium monoperoxyphthalate, with Oxone being preferred.

For example, the sulfide of formula (13) is treated with a suitable base, such as sodium bicarbonate followed by a suitable oxidizing agent, such as Oxone. The reaction is carried out in a suitable solvent, such as acetone, DMF, glyme, dioxane, $CH_3CN$, alcohols, THF, EtOAc, halohydrocarbons, chlorobenzene, and toluene, with acetone being preferred. Generally, the reaction is carried out at temperatures of from about −30° C. to about 50° C. with from about −10° C. to about 10° C. being preferred. Generally, the reaction requires from about 15 minutes to about 5 hours. Crude sulfone or sulfoxide (14) may be used without further purification. Alternatively, the sulfone or sulfoxide of formula (14) may be isolated and purified according to procedures well known in the art such as extraction, evaporation, chromatography and recrystallization.

In Scheme B, step 8, the sulfone or sulfoxide of formula (14) is deprotected with a suitable deprotecting agent to provide the amine of formula (14a).

A suitable deprotecting agent is an agent capable of removing the base labile substituent $R^{82}$ on the compound of formula (14) while inert to the epoxide moiety of the molecule. Suitable deprotecting agents include bases such as secondary and tertiary amines and inorganic bases, for example, piperidine, morpholine, dicyclohexylamine, p-dimethylaminopyridine, diisopropylethylamine, and the like, with piperidine being preferred. The reaction is carried out in a suitable solvent such as DMF, glyme, dioxane, $CH_3CN$, alcohols, THF, EtOAc, halohydrocarbons, chlorobenzene, or toluene. Generally, the reaction is carried out at a temperature ranging from about 0° C. to about 120° C. Generally, the reaction requires from about 1 to 72 hours. The compound of formula (IIB) may be isolated and purified by techniques well known in the art, such as extraction, evaporation, chromatography and recrystallization. Alternatively, the compound of formula (14a) is isolated and may be further cyclized with a cyclizing agent to provide a compound of formula (IIB).

Typically, once the compound of formula (14) is deprotected, it undergoes spontaneous cyclization. However, some particular compounds of formula (14) may require an additional cyclization step. Also, for example, the sulfide of formula (13), although much less active than its oxidized counterpart, upon removal of the base-labile protecting group may be cyclized with a second suitable cyclizing agent, such as 2-hydroxypyridine to form a compound of formula (IIB). For example, the sulfide of formula (13), or alternatively a selected compound of formula (14a), is heated in a suitable solvent, such as DMF at about 60° C. for several days in the presence of piperidine and 2-hydroxypyridine. The compound of formula (IIB) is isolated and purified by techniques well known in the art, such as extraction, evaporation, chromatography and recrystallization.

In Scheme B, step 9, the epoxide of formula (IIB) is optionally treated with a halohydrin forming reagent to produce the halohydrin of formula (IIC), where Hal is halogen, preferably chlorine.

A "halohydrin forming reagent" is any agent capable of coverting the epoxide moiety of compound (IIB) to the halohydrin moiety of compound (IIC). Suitable halohydrin forming reactions are disclosed in PCT Intnl. Publ. No. WO 96/40184, published Dec. 19, 1996 and PCT Intnl. Publ. No. WO 98/09988, published Mar. 12, 1998. For example, the epoxide of formula (IIB) is treated with a suitable halo-acid, such as hydrochloric acid in a suitable organic solvent or solvent mixture, such as dimethoxy-ethane/water. The mixture is then stirred at a temperature ranging from about 10° C. to about 50° C. for a period of time ranging from about 6 to 36 hours. The mixture is then neutralized with a suitable base or buffer, such as potassium carbonate. The halohydrin of formula (IIC) is isolated and purified by techniques well known in the art, such as extraction, evaporation, chromatography and recrystallization.

In Scheme B, step 10, the halohydrin of formula (IIC) is reacted with a glycinating agent to provide the glycinate ester of formula (IID).

A "glycinating agent" is any agent capable of converting the halohydrin of formula (IIC) into the glycinate ester of formula (IID). Suitable glycinating reactions are disclosed in PCT Intnl. Publ. No. WO 98/08505, published Mar. 5, 1998. For example, the halohydrin of formula (IIC) is coupled with N-(tert-butoxycarbonyl)glycine (Boc-Gly) under coupling conditions well known in the art. For example, the halohydrin of formula (IIC) is contacted with Boc-Gly, dimethylaminopyridine (DMAP) and 1,3-dicyclohexylcarbodiimide (DCC). The resulting mixture is stirred at a temperature ranging from 10° C. to 50° C. for a period of time ranging from 0.5 to 24 hours. The glycinate ester of formula (IID) is isolated and purified by techniques well known in the art, such as extraction, evaporation, chromatography and recrystallization.

A synthetic scheme for making the Fragment CD carboxylic acids of formula (12a) is set forth in Scheme C. The reagents and starting material are readily available to one of ordinary skill in the art. In Scheme C, all substituents, unless otherwise indicated, are as previously defined.

SCHEME C

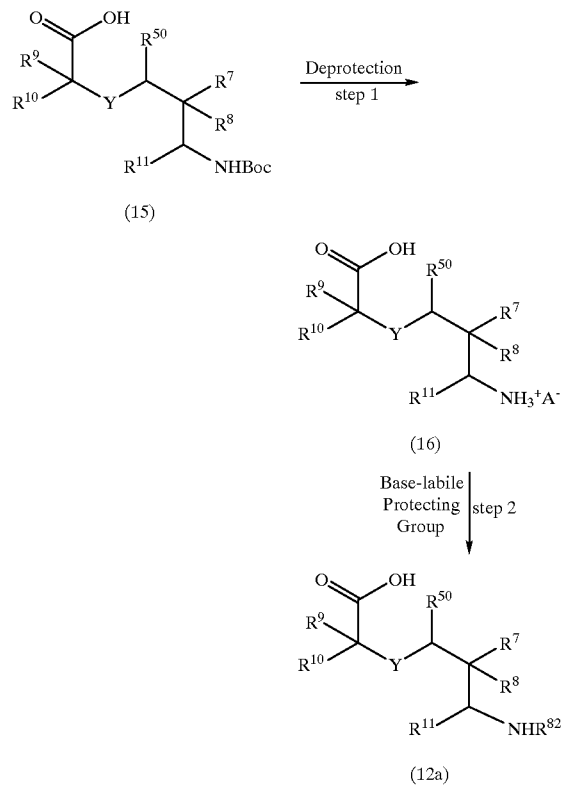

In Scheme C, step 1, the Boc-protected amine of formula (15) is deprotected to provide the deprotected amine of formula (16).

For example, the deprotection reaction involves the removal of an amino protecting group by techniques and procedures well known and appreciated by one of ordinary skill in the art. The selection, use, and removal of 10 protecting groups are set forth by Greene, T. W. "Protecting Groups in Organic Synthesis", Wiley (New York, 1981). For example, the Boc-protected amine of formula (15) is dissolved in a suitable acid, such as trifluoroacetic acid or hydrochloric acid. Generally, the reaction is carried out at a temperature ranging from about 0° C. to about 60° C. Generally, the reaction requires from about 1 to 24 hours. The deprotected amine of formula (16) may be isolated and purified by techniques well known in the art, such as extraction, evaporation, chromatography and recrystallization.

The Boc-protected amine of formula (15) is described in Barrow, R. A. et al. J. Am. Chem. Soc. 117, 2479 (1995); PCT Intnl. Publ. No. WO 96/40184, published Dec. 19, 1996; and PCT Intnl. Publ. No. WO 97/07798, published Mar. 6, 1997.

In Scheme C, step 2, the deprotected amine of formula (16) is amino-protected with a base-labile amino protecting group to provide the carboxylic acid of formula (12a).

For example, the protection of an amino group with a base-labile amino protecting group involves the addition of a base-labile amino protecting group by techniques and procedures well known and appreciated by one of ordinary skill in the art. The selection, use, and removal of base-labile amino protecting groups are set forth by Greene, T. W. "Protecting Groups in Organic Synthesis", Wiley (New York, 1981). A preferred base-labile amino protecting group is Fmoc. For example, to a solution of the deprotected amine of formula (16) in a suitable solvent, such as dioxane, is added a suitable base, such as sodium bicarbonate, followed by a compound of the formula $R^{82}$-Cl or $R^{82}$-ONHS, such as Fmoc-Cl or Fmoc-ONHS succinimide. The mixture may be optionally diluted with a small amount of water and stirred for a period of time ranging from 12 to 48 hours at a temperature ranging from about 0° C. to about 60° C. The mixture may be quenched with a suitable acid, such as hydrochloric acid. The carboxylic acid of formula (12a) may be isolated and purified by techniques well known in the art, such as extraction, evaporation, chromatography and recrystallization.

For further example, Scheme D illustrates a general synthetic procedure for preparing a cryptophycin compound of formula (II). In Scheme D, all substituents, unless otherwise indicated, are as previously defined. As used herein, the substituent "Hal" stands for halogen.

SCHEME D

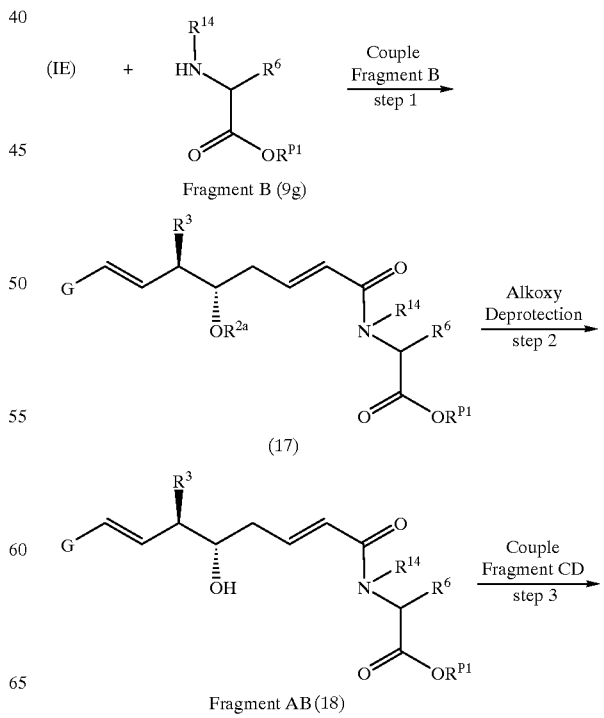

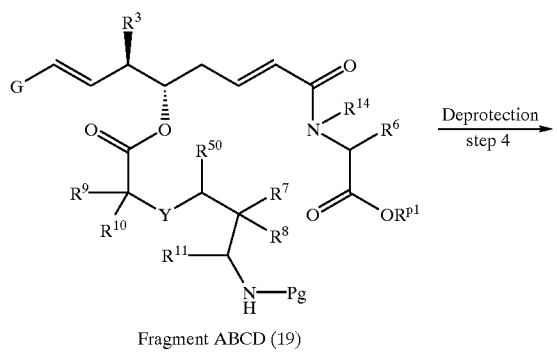

Fragment ABCD (19)

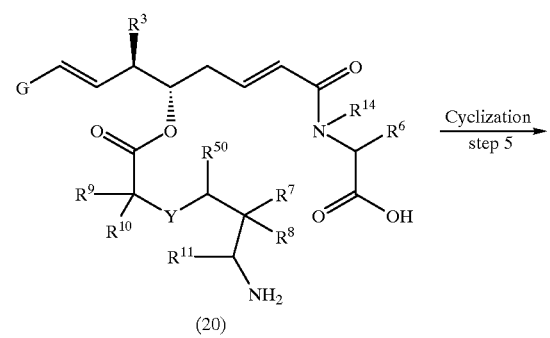

(20)

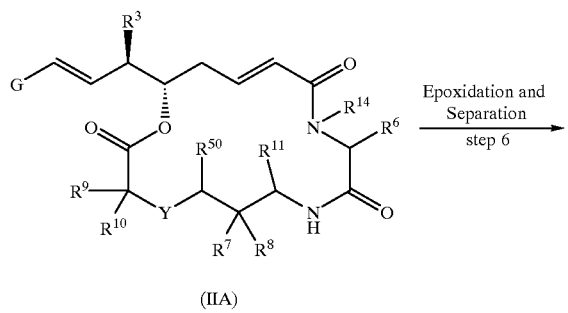

(IIA)

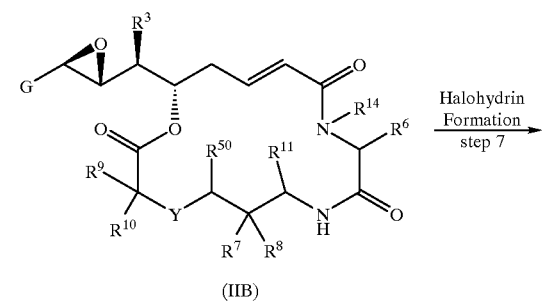

(IIB)

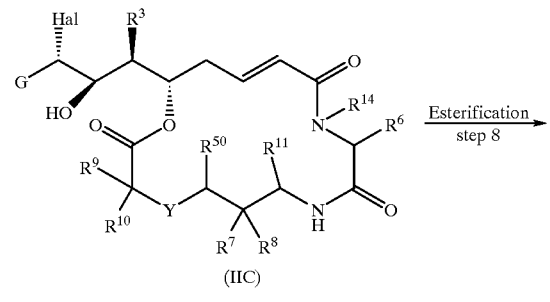

(IIC)

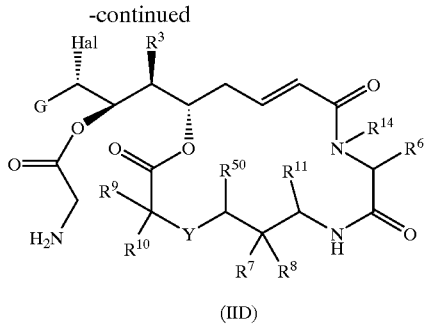

(IID)

In Scheme D, step 1, a compound of formula (IB) is coupled with a Fragment B amino acid of formula (9g) to provide an alkoxy-protected Fragment AB compound of formula (17) according to the procedure set forth in Scheme B, step 3.

In Scheme D, step 2, an alkoxy-protected Fragment AB compound of formula (17) is alkoxy-deprotected according to the procedure set forth in Scheme B, step 4 to provide a Fragment AB compound of formula (18). Alternatively, the alkoxy-protected Fragment AB compound of formula (17) is deprotected according to techniques and procedures well known to one of ordinary skill in the art. Since the alkoxy-protected Fragment AB compound of formula (17) does not possess an epoxide group as does the corresponding analog in Scheme B, the deprotecting reaction conditions are not required to be as sensitive. For example, an alkoxy-protected Fragment AB compound of formula (17) may be deprotected according to the procedure set forth in Barrow, R. A. et al, *J. Am. Chem. Soc.* 117, 2479 (1995), which includes 50% aqueous HF in a $CH_3CN$ solution.

In Scheme D, step 3, a Fragment AB compound of formula (18) is coupled with a Fragment CD carboxylic acid of the formula:

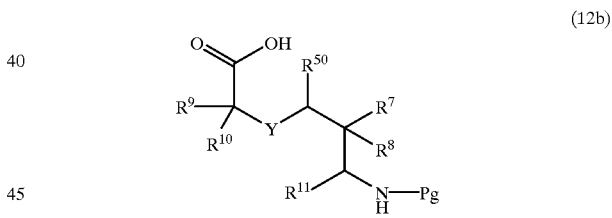

(12b)

wherein $R^7$, $R^8$, $R^9$, $R^{10}$, $R^{11}$, $R^{50}$ and Y are as defined above and Pg is a suitable amino protecting group, according to the procedure set forth in Scheme B, step 6 to provide a Fragment ABCD compound of formula (19). Suitable amino protecting groups are well known by one of ordinary skill in the art and are disclosed in Greene, "Protective Groups in Organic Chemistry", John Wiley & sons, New York (1981), the disclosure of which is hereby incorporated by reference. A particularly preferred amino protecting group is t-Boc.

In Scheme D, step 4, a Fragment ABCD compound of formula (19) is deprotected with a suitable second deprotecting agent to provide the deprotected Fragment ABCD compound of formula (20).

A suitable "second deprotecting agent" is any agent or combination of agents which are effective in removing both the "Pg" amino protecting group and the "$R^{p1}$" carboxy protecting group, either sequentially or concomitantly. Since the Fragment ABCD compound of formula (19) does not possess an epoxide group as does the sulfoxide or sulfone of formula (14) in Scheme B, step 8, the deprotecting reaction conditions are not required to be as sensitive. For example, a Fragment ABCD compound of formula (19) may be deprotected according to the procedure set forth in Barrow, R. A. et al, *J. Am. Chem. Soc.* 117, 2479 (1995). The deprotected Fragment ABCD compound of formula (20) may be isolated and purified by techniques well known in the art, such as extraction, evaporation, chromatography and recrystallization.

In Scheme D, step 5, the deprotected ABCD compound of formula (20) is cyclized with a second suitable cyclizing agent according to Barrow, R. A. et al, *J. Am. Chem. Soc.* 117, 2479 (1995) to form the cyclic alkene of formula (IIA). Alternatively, the deprotected ABCD compound of formula (20) may be cyclized with a suitable cyclizing agent according to Scheme B, step 8. The cyclic alkene of formula (IIA) may be isolated and purified by techniques well known in the art, such as extraction, evaporation, chromatography and recrystallization.

In Scheme D, step 6, the cyclic alkene of formula (IIA) is epoxidized according to the procedures set forth in Scheme B, step 2 or Scheme B1 to provide the epoxide of formula (IIB).

In Scheme D, step 7, the epoxide of formula (IIB) is treated with a halohydrin forming reagent according to Scheme B, step 9 to produce the halohydrin of formula (IIC).

Alternatively, the cyclic alkene of formula (IIA) is contacted sequentially with an epoxidizing agent and a trialkylsilyl chloride according to PCT Intnl. Publ. No. WO 98/09988, published Mar. 12, 1998 to provide the halohydrin of formula (IIC) where "Hal" is chloro.

In Scheme D, step 8, the halohydrin of formula (IIC) is reacted with a glycinating agent according to Scheme B, step 10, to provide the glycinate ester of formula (IID).

Optionally, on those compounds of formulae (I) or (II) containing basic or acidic functional groups, pharmaceutically acceptable salts of the compounds of formulae (I) or (II) may be formed using standard techniques. For example, the free base may be dissolved in aqueous or aqueous-alcohol solution or other suitable solvent containing the appropriate acid and the salt isolated by evaporating the solution. Alternatively, the free base may be reacted in an organic solvent containing the appropriate acid and the salt isolated by evaporating the solution. Further, the free base may be reacted in an organic solvent in which case the salt separates directly or can be obtained by concentration of the solution or in a solvent such as water which is then removed in vacuo or by freeze-drying, or by exchanging the cations of an existing salt for another cation on a suitable ion exchange resin.

It should be noted that since one aspect of the invention represents a convergent synthesis to produce a cryptophycin compound of formula (II), alternate sequences of couplings may be utilized. For example, Fragment A may be first coupled to Fragment B to form Fragment AB and Fragment C' to Fragment D to form Fragment C'D. Fragment AB may then be coupled to Fragment C'D to form Fragment ABC'D.

Preferred embodiments of the processes for preparing compounds of formulae (I) and (II) are given individually below:

(a) G is phenyl, p-fluorophenyl, or p-chlorophenyl;
(b) $R^1$ is chloro and $R^2$ is OH;
(c) $R^1$ is chloro and $R^2$ is glycinate ester;
(d) $R^1$ and $R^2$ are taken together to form an epoxide ring;
(e) $R^1$ and $R^2$ are taken together to form a bond;
(f) $R^3$ is methyl;
(g) $R^6$ is a group of formula (IA) wherein $R^{6a}$ is chloro, $R^{6b}$ is methoxy and $R^{6c}$ is hydrogen;

(h) one of $R^7$ or $R^8$ is hydrogen while the other is methyl;
(i) $R^7$ and $R^8$ are both methyl;
(j) $R^9$ is hydrogen and $R^{10}$ is $C_1$–$C_6$ methyl;
(k) $R^{11}$ is hydrogen;
(l) $R^{14}$ is hydrogen;
(m) $R^{50}$ is (=O);
(n) Y is O;
(o) the combination of embodiments (a), (b), (f), (g), (h), (j), (k), (l), (m) and (n);
(p) the combination of embodiments (a), (c), (f), (g), (h), (j), (k), (l), (m) and (n);
(q) the combination of embodiments (a), (d), (f), (g), (h), (j), (k), (l), (m) and (n);
(r) the combination of embodiments (a), (e), (f), (g), (h), (j), (k), (l), (m) and (n);
(s) the combination of embodiments (a), (b), (f), (g), (i), (j), (k), (l), (m) and (n);
(t) the combination of embodiments (a), (c), (f), (g), (i), (j), (k), (l), (m) and (n);
(u) the combination of embodiments (a), (d), (f), (g), (i), (j), (k), (l), (m) and (n); and
(v) the combination of embodiments (a), (e), (f), (g), (i), (j), (k), (l), (m) and (n).

To further illustrate the invention the following examples are provided. The scope of the invention is in no way to be construed as limited to or by the following examples. The terms and abbreviations used in the instant examples have their normal meanings unless otherwise designated. For example "° C." refers to degrees Celsius; "N" refers to normal or normality; "mmol" refers to millimole or millimoles; "g" refers to gram or grams; "ml" or "mL" means milliliter or milliliters; "M" refers to molar or molarity; "MS" refers to mass spectrometry; "IR" refers to infrared spectroscopy; and "NMR" refers to nuclear magnetic resonance spectroscopy.

Preparation 1

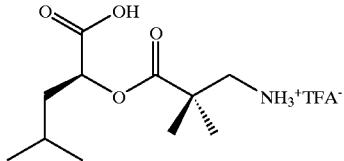

Boc amine (1.69 g, 5.09 mmols) of the formula

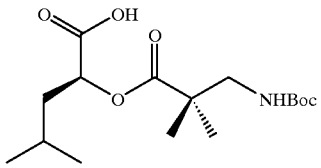

PCT Intnl. Publ. No. WO 97/07798, published Mar. 6, 1997; was dissolved in trifluoroacetic acid (17 ml) and the solution stirred at room temperature under a dry nitrogen atmosphere for 4.75 h and then concentrated in vacuo and dried under high vacuum for 24 h to give the amine salt as a yellow viscous oil (1.76 g, 100%).

$[\alpha]_D^{589}$ –11.54° (c 1.04, MeOH); $^1$H NMR (CDCl$_3$) δ Unit C': 7.43 (br s, 3H, NH$_3^+$),3.34–3.28 (m, 3-H), 3.18–3.12 (m, 3-H'), 1.42 (s, 2-Me), 1.36 (s, 2-Me); Unit D:

10.94 (br s, CO₂H), 5.23–5.20 (m, 2-H),1.92–1.77 (m, 3H, 3-HH', 4-H), 1.10 (d, J=5.8 Hz, 5-H₃), 0.98 (d, J=5.8 Hz, 4-Me) ppm; IR (CHCl₃) ν 2963, 1746, 1710, 1678, 1192, 1172 cm⁻¹; MS (FAB) 232.2 ([M+1]⁺, 100).

Preparation 2

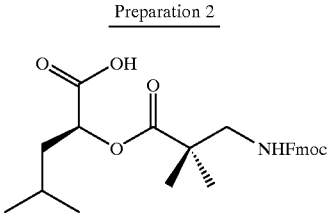

To a stirred solution of amine salt of Preparation 1 (5.09 mmols) in dioxane (20 mL) was added sodium bicarbonate (2.14 g,25.5 mmols) followed by FmocCl (1.58 g,6.11 mmols) at room temperature. The mixture was diluted with H₂O (4 mL) and stirred for 19 h. The reaction mixture was quenched in 1N aqueous HCl (150 mL) and extracted with EtOAc (2×100 mL). Combined organics were washed with H₂O (100 mL), dried (MgSO₄) and concentrated in vacuo to give a yellow gummy solid. The crude product was purified by column chromatography (Biotage-SiO2: gradient elution; 10%–75% EtOAC: Hexanes) to provide Fmoc amine as a pale yellow solid (850 mg, 37%). Product was contaminated with amino acid, which was removed by dissolving the product in EtOAc and stirring with 1N HCl aq for several hours. Organics were dried and concentrated to give product (85:15 product: amino acid).

$[\alpha]_D^{589}$ –15.95° (c 0.50, CH₂Cl₂); ¹H NMR (CDCl₃) δ Unit C': 7.59 (d, J=7.4 Hz, ArH₂) , 7.67–7.61 (m, ArH₂), 7.43 (t, J=7.3 Hz, ArH₂), 7.36–7.30 (m, ArH₂), 5.88 (t, J=5.8 Hz, NH), 4.41–4.38 (m, 3'-HH'), 4.35–4.28 (m,4'-H), 3.42 (d, J=6.5 Hz, 3-HH'), 1.27 (s, 2Me), 1.26 (s, 2-Me); Unit D: 8.40 (br s, CO2H), 5.18–5.13 (m, 2-H), 1.87–1.69 (m, 3H, 3-HH', 4-H), 0.97 (d, J=5,8 Hz, 5-H3), 0.93 (d, J=6.1 Hz, 4-Me) ppm; IR (KBr) ν 2959, 2937, 1730, 1540, 1471, 1451, 1307, 1268, 1145, 1128, 759, 741 cm⁻¹; UV (EtOH) λmax 299 (e=5851), 288 (e=4773), 265 (e=18369), 227 (e=4813) nm; MS (FAB) 454 ([M+1]⁺, 26); Anal. calcd. for C₂₆H₃₁NO₆ requires: C, 68.86; H, 6.89; N, 3.09%. Found: C, 68.92; H, 7.01; N, 3.34%.

Preparation 3

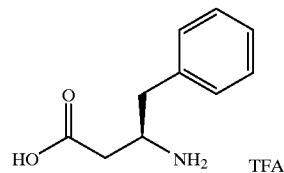

(3R)-benzyl-3-aminopropanoic acid (TFA salt)

A sample of t-Butyl-3-(R)-benzyl-3-amino-propanoic acid (purchased from oxford Asymmetry, England, >99% e.e) was dissolved in trifluoroacetic acid (TFA) and then let stirred at room temperature for 4 h. The trifluoroacetic acid was removed in vacuo to give an oily residue which was then triturated with methanol to give a white solid.

TLC: Rf=(CHC13/CH3OH/NH4OH: 6:3.2:0.8)

IR (cm⁻¹):

¹HNMR(300 MHz, DMSO-d6) d: 7.93 (bs, 2H), 7.32 (m, 5H), 3.63 (t, J=7.2 Hz, 1H), 2.91 (dd, J=5.9 Hz, J=13.6 Hz, 2H), 2.77 (dd, J=8.1 Hz, J=13.6 Hz, 2H)

Anal: Calcd for C12H14NO4: C, 49.15; H, 4.81; N, 4.78. Found: C, 48.87; H, 4.73, N, 4.70.

Preparation 4

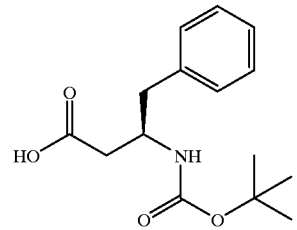

(3R)-benzyl-3-(tert-butoxycarbonyl)amino-propanoic acid

A sample of the compound of Preparation 3 was dissolved in 1,4-dioxane/H2O/2.0 NNaOH (2:2:1) at 0° C. (ice bath). To this was then added di-t-butyl-dicarboxylate and the ice bath was removed and the resulting reaction mixture was let stirred at room temperature for 18 h. The reaction mixture was then concentrated to about 10 ml and 25 ml of EtOAc was added. To this was then added 0.5 N NaHSO4 to lower the pH of aqueous phase to ca. 2–3. The organic layer was then separated and the aqueous layer was extracted with EtOAc (20 ml ×3). The combined EtOAc layer was then washed with water and brine and dried over NaSO₄. The solvent was then removed in vacuo to give a pale yellow solid.

TLC: Rf=(CHC13/CH3OH/NH4OH: 6:3.2:0.8)

IR (cm⁻¹): 3361, 2985, 1670, 1686, 1526, 1266, 1168, 700.

UV (CH3OH): 258 nm (e=158).

OR: [α]_D=–136.71

¹HNMR(300 MHz,DMSO-d6) d: 7.20 (m, 5H), 6.75 (d, J=8.6 Hz, 1H), 3.88 (m, 1H), 2.64 (d, J=7.0 Hz, 2H), 2.28 (t, J=5.1 Hz, 2H)1.27 (s, 9H).

Mass(FAB): 280 (M⁺+H).

Anal: Calcd for C15H21NO4: C, 64.50; H,7.58; N,5.01. Found: C, 63.25; H, 7.35, N, 4.99.

Preparation 5

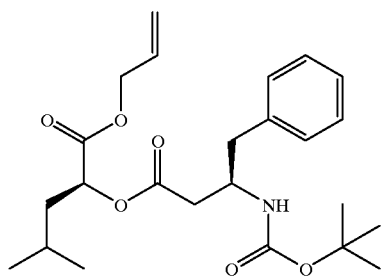

Allyl (2S)-2-[3'(tert-Butoxycarbonyl)amino-2'-(R)-benzylpropanoyloxy]-4-methylpentanoate.

To a solution of allyl (2S)-2-hydroxy-4-methylpentanoate and (3R)-benzyl-3-(tert-butoxycarbonyl)amino-propanoic acid (Preparation 4) in 10 ml of dry methylene chloride at 0° C. (ice bath), was added dicyclohexylcarbodiimide and then followed by DMAP. The reaction mixture was then let stirred at room temperature for 3 h (TLC indicated the completion of the reaction). The reaction mixture was then filtered through a small pad of celite and the filtrate was washed with 5% NaHCO$_3$, brine and dried over Na$_2$SO$_4$. The solvent was removed in vacuo and the residue was flash chromatographed on SiO$_2$ (15% EtOAc/hexane) to give the title compound as a clear oil.

TLC: Rf=(20% EtOAc/hexane)

IR (cm$^{-1}$): 2961, 2933, 1742, 1715, 1497, 1366, 1249, 1170, 1127.

UV (CH3OH): 258 nm (e=218).

OR: [a]$_D$=+7.55

$^1$HNMR(300 MHz, CDCl3) d: 7.25 (m, 5H), 5.89 (m, 1H), 5.20–5.36 (m, 3H), 5.10 (dd, J=3.9 Hz, J=9.6 Hz, 1H), 4.65 (d, J=5.4 Hz, 2H), 4.15 (bs, 1H), 2.87 (m, 2H), 2.62 (dd, J=5.6 Hz, J=15.4 Hz, 1H), 2.50 (dd, J=5.0 Hz, J=15.4 Hz, 1H), 1.60–1.85 (m, 3H), 1.40 (s, 9H), 0.95 (d, J=4.3 Hz, 3H), 0.93 (d, J=4.3 Hz, 3H).

Mass(FAB): 434.4 (M$^+$+H).

Anal: Calcd for C24H35NO6: C, 66.49; H, 8.14; N, 3.23. Found: C, 66.32; H, 8.29, N, 3.42.

EXAMPLE 1

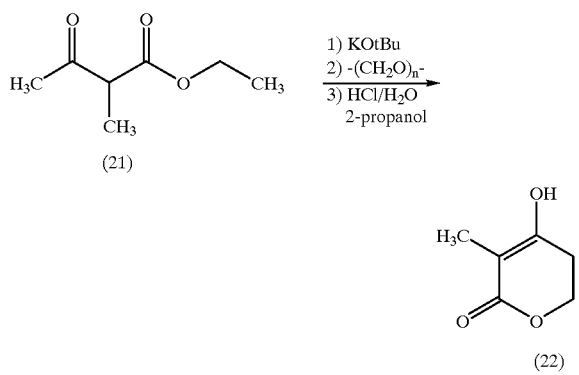

5,6-Dihydro-4-hydroxy-3-methyl-2H-pyran-2-one (22)

A solution of potassium t-butoxide (11.2 g, 100 mmol) was prepared in 2-propanol (160 mL), stirred, and cooled to 0° C. under nitrogen. This mixture was treated with ethyl 2-methylacetoacetate (21, 12.0 g, 83.2 mmol), dropwise, and at such a rate as to keep the temperature at or below +5° C. (approximately 10 min.). After stirring for 20 min at 0° C., the resulting slurry was treated with paraformaldehyde (6.00 g, 200 mmol), in one portion, the ice bath was removed, and the suspension was stirred at room temperature for 90 min. The resulting cloudy yellow mixture was evaporated and the residue partitioned between ice water and TBME. The layers were separated and the aqueous layer was diluted with tetrahydrofuran (150 mL), cooled to 0° C., and acidified with HCl (conc., 10 mL, 120 mol). After stirring for 30 min, the mixture was treated with NaCl (20 g), the layers were separated, and the aqueous layer was extracted with tetrahydrofuran (150 mL). The organic layers were dried (MgSO$_4$), filtered, and the filtrate evaporated. The residue was stirred with EtOAc (100 mL) at 0° C. for 30 min and filtered to provide 5,6-dihydro-4-hydroxy-3-methyl-2H-pyran-2-one (22) as a snow white powder (5.90 g, 55% yield): mp 138–144° C. (d) ; IR (KBr) v$_{max}$ 3421, 1631 cm$^{-1}$; $^1$H NMR (DMSO-d$_6$) δ10.6 (1H, bs), 4.18 (2H, t, J=6.4 Hz), 2.53 (2H, t, J=6.4 Hz), 1.63 (3H, s); MS (FIA), m/z 129.1 (M+1)$^+$.

EXAMPLE 2

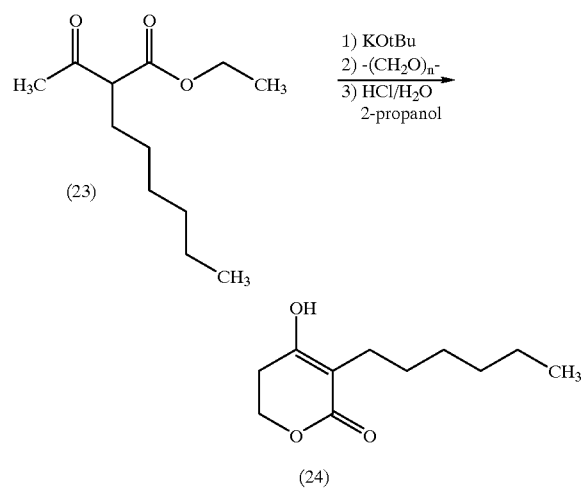

5,6-Dihydro-3-n-hexyl-4-hydroxy-2H-pyran-2-one (24)

A solution of potassium t-butoxide (0.69 g, 5.65 mmol) was prepared in 2-propanol (9 mL), stirred, and cooled to 0° C. under nitrogen. This mixture was treated with ethyl 2-n-hexylacetoacetate (23, 1.00 g, 4.67 mmol), dropwise, and at such a rate as to keep the temperature at or below +6° C. (approximately 5 min.). After stirring for 20 min at 0° C., the resulting slurry was treated with paraformaldehyde (0.34 g, 2.42 mmol), in one portion, the ice bath was removed, and the suspension was stirred at room temperature for 90 min. The mixture was cooled to 0° C. and acidified with HCl (1N, 6 mL, 6 mmol). After stirring overnight at room temperature, the mixture was concentrated and the residue partitioned between water and CH$_2$Cl$_2$, and the organic layers were dried (MgSO$_4$), filtered, and the filtrate evaporated. The resulting oil was dissolved in hexanes (10 mL), allowed to stand at 0° C. for 60 min, then filtered to provide 5,6-dihydro-3-n-hexyl-4-hydroxy-2H-pyran-2-one (24) as a snow white powder (370 mg, 40% yield): mp 98–99° C. (d). Anal. Calcd for C$_{11}$H$_{18}$O$_3$ (198.26): C, 66.64; H, 9.15. Found: C, 66.49; H, 9.14. IR (KBr): v$_{max}$ 2924, 1594, 1381 cm$^{-1}$; $^1$H NMR (DMSO-d$_6$) δ10.6 (1H, bs), 4.16 (2H, t, J=6.3 Hz), 2.54 (2H, t, J=6.3 Hz), 2.15 (2H, t, J=7.4 Hz), 1.3 (8H, m); 0.86 (3H, t, J=6.8 Hz); MS (FIA), m/z 199.2 (M+1)$^+$.

EXAMPLE 3

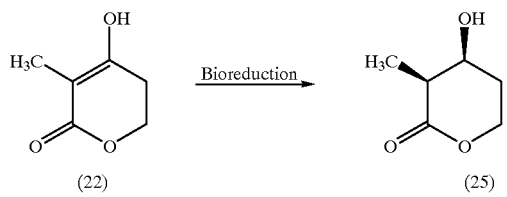

Mortierella isabellina ATCC 42613 Bioconversion of 2-methyl-3-keto-δ-valerolactone, hydride form The culture Mortierella isabellina ATCC 42613, as a frozen vegetative mycelia, was thawed and used to inoculate 10 mL of Difco YM Broth (42 g/L) with 0.3% Difco YM Agar in a 50 ml Erlenmeyer flask. The flask was incubated at 26° C. for 48 hours on a shaker orbiting in a two inch circle at 250 rpm. Cells were harvested by centrifugation at 1,700×g for 10 minutes. These cells were suspended in 100 mM potassium phosphate buffer pH 6.0 with 4% glucose to obtain a 5 mL volume. To this cell suspension was added 10 mg of 2-methyl-3-keto-δ-valerolactone, hydride form, in 5 mL of same buffer for a final concentration of 7.8 μmoles/ mL. Bioconversion flask was incubated at 26° C. for 48 hours on a shaker orbiting in a two inch circle at 250 rpm. At 48 hours, the reaction mixture was extracted with 12 mL of ethyl acetate. Progress of the bioconversion was detected by examining the ethyl acetate layer on thin layer chromatography (TLC) for the disappearance of the substrate and the appearance of the product 2-methyl-3-hydroxy-valerolactone. TLC system consisted of Whatman silica gel 60 F-254 run in ethyl acetate/hexane (8/2, v/v) and detection with UV and 5% aqueous potassium permanganate. The ethyl acetate extract was concentrated to dryness by vacuum. Dried extracts for chiral analysis were reconstituted with methylene chloride. Derivatization of 2-methyl-3-hydroxy-valerolactone was conducted with trifluoroacetic anhydride. The diastereomeric and enantiomeric purity of the (S,S) isomer of 2-methyl-3-hydroxy-valerolactone in this example were determined to be 97% and 96% respectively by utilizing gas chromatography analysis. This analysis was conducted under the following conditions:

Chromatograph : HP 6890 gas chromatograph

Column : Astec Chiraldex B-PH analytical capillary column

Temperature : 150° C., isothermal

Carrier gas : He at 1.5 mL/min

Injector: 200° C., split ratio=1: 200

Detector: Flame Ionization Detector (FID), 200° C. $H_2$ flow: 40 mL/ min Air flow: 450 mL/ min

EXAMPLE 3A

Mortierella isabellina ATCC 42613 Two Liter Scale Bioconversion of 2-Methyl-3-Keto-δ-Valerolactone, Hydride Form A –70° C. frozen vegetative mycelia preparation of *Mortierella isabellina* ATCC 42613 was thawed and used to inoculate the vegetative medium consisting of Difco YM Broth (42 g/L) with 0.2% YM agar. One ml of culture stock was used to inoculate 50 mL of medium in a 250 mL Erlenmeyer flask. This inoculated medium was incubated at 26° C. for 48 hours on a shaker orbiting in a two inch circle at 250 rpm. This growth (8 mL) was used to inoculate fermentation medium (200mL/flask) of the same composition in 1 liter Erlenmeyer flasks The fermentation stage was incubated at 26° C. for 48 hours on a shaker orbiting in a two inch circle at 250 rpm. Cells were harvested by centrifugation at 17,700×g for 15 minutes. The cells were placed in a 2 liter bioreactor and suspended in 150 mM citrate phosphate buffer pH 4.5 for a final volume of 2L. Dextrose was added for final concentration of 1% (w/v). The hydride form of 2-methyl-3-keto-δ-valerolactone was added for a final concentration at 23.4 mmoles/L. The pH was adjusted to pH 4.5 with 6N HCl and maintained during the bioconversion at pH 4.5 by addition of 8N $NH_4OH$ and 3N HCl. The dissolved oxygen level was controlled at 30% by the addition of sterile air at a flow rate from 0.5 liters per minute (1 pm) and an agitation rate from 500 to 950 rpm. The temperature was maintained at 26° C. during the bioconversion. Progress of the bioconversion was detected on high pressure liquid chromatography (HPLC) by monitoring the disappearance of the substrate. The HPLC system utilized was an isocratic system at 1.0 mL $min^{-1}$ on a Waters RCM 8×10 RadialPak containing a NovaPak C18 column cartridge with a NovaPak C18 guard column with a detection at 254 nm. The solvent system is comprised of 25 mM ammonium phosphate buffer, adjusted to pH 3.5 with acetic acid/acetonitrile (9/1, v/v). Retention time of substrate is 5.5 minutes. The hydroxylactone could not be detected under these conditions. After 23 hours, the cells were removed by centrifugation at 30,100×g. The supernatant then was saturated with sodium chloride (~20 g/L) and then extracted 3 times with equal volume of acetonitrile. The aqueous layer was discarded. Acetonitrile layers were combined and concentrated to dryness by vacuum. Determination of the enantiomeric purity of the 2-methyl-3-hydroxy-valerolactone was conducted as follows. When the 2-methyl-3-keto-δ-valerolactone was not detected on HPLC, a sample of the bioconversion broth was concentrated to dryness by vacuum. The dried sample was reconstituted with methylene chloride then derivatized with trifluoroacetic anhydride. The enantiomeric excess purity of the (S,S) isomer of 2-methyl-3-hydroxy-valerolactone was determined to be 94% by utilizing gas chromatography (GC) analysis. GC analysis was conducted under the following conditions:

Chromatograph: HP 6890 gas chromatograph

Column: Astec Chiraldex B-PH analytical capillary column

Temperature: 150° C., isothermal

Carrier gas: He at 1.5 mL/min

Injector: 200° C., split ratio =1:200

Detector: Flame Ionization Detector (FID), 200° C. $H_2$ flow: 40 mL/min Air flow: 450 mL/min

EXAMPLE 3B

Mortierella isabellina ATCC 42613 100 L Scale Bioconversion of 2-methyl-3-keto-δ-valerolactone, Hydride or Potassium Salt Form Inoculum for the tank fermentation and bioconversion were prepared in two stages. A –70° C. frozen vegetative mycelia preparation of *Mortierella isabellina* ATCC 42613 was thawed and used to inoculate first stage vegetative medium consisting 2.6% dextrose, 1.6% yeast extract, and 0.1% Bacto Agar. One ml of culture stock was used to inoculate 50 mL of medium in a 250 mL Erlenmeyer flask. This inoculated medium was incubated at 26° C. for 48 hours on a shaker orbiting in a two inch circle at 250 rpm. This growth (10 mL) was used to inoculate a second stage vegetative medium (400 mL) of the same composition in 2 liter Erlenmeyer flasks. This second stage was incubated at 26° C. for 48 hours on a shaker orbiting in a two inch circle at 250 rpm. Two liters of the second stage were used to inoculate a 150 liter fermentor containing 100 liters of medium of same composition without the agar. Ammonium hydroxide and sulfuric acid were used to maintain the pH between 5.0–6.0. The culture was allowed to grow for 24 hours in the fermentor maintaining the temperature at 26° C. The dissolved oxygen level was controlled at 30% by the addition of sterile air at a flow rate from 0.5 to 3.5 scfm and an agitation rate from 150 to 450 rpm. At 24 hours the pH of the fermentation was adjusted to 4.5 with 30% sulfuric acid. The substrate 2-methyl-3-keto-d-valerolactone, hydride or potassium salt form, was added for a final concentration of 23.4 mmoles/ L. The rate of the bioconversion was monitored on high pressure liquid chromatography (HPLC). The HPLC system utilized was an isocratic system at 1.0 ml min$^{-1}$ on a Waters RCM 8×10 RadialPak containing a NovaPak C18 column cartridge with a NovaPak C18 guard column with a detection at 254 nm. The solvent system is comprised of 25 mM ammonium phosphate buffer, adjusted to pH 3.5 with acetic acid/acetonitrile (95/5, v/v). Retention time of substrate is 5.5 minutes. When bioconversion was complete, the cells were removed by filtration of broth through a 6" single plate filter. Sodium chloride was added to the filtrate (20%, w/v). This solution was extracted 3 times with equal volume of acetonitrile. The aqueous layer was discarded. The organic layer is concentrated under vacuum and then the concentrate is filtered to remove salts.

EXAMPLE 3C

*Mortierella isabellina* ATCC 42613 1000 L Scale Bioconversion of 2-methyl-3-keto-δ-valerolactone, Potassium Salt Form Inoculum for the tank fermentation and bioconversion were prepared in three stages. A −70° C. frozen vegetative mycelia preparation of *Mortierella isabellina* ATCC 42613 was thawed and used to inoculate first stage vegetative medium consisting of 2.6% dextrose, 1.6% yeast extract, and 0.1% Bacto Agar. One ml of culture stock was used to inoculate 50 mL of medium in a 250 mL Erlenmeyer flask. This inoculated medium was incubated at 26° C. for 48 hours on a shaker orbiting in a two inch circle at 250 rpm. This growth (10 mL) was used to inoculate a second stage vegetative medium (400 mL) of the same composition in 2 liter Erlenmeyer flasks. This second stage was incubated at 26° C. for 48 hours on a shaker orbiting in a two inch circle at 250 rpm. Two liters of the second stage were used to inoculate a 150 liter fermentor containing 100 liters of medium of same composition without the agar. Ammonium hydroxide and sulfuric acid were used to maintain the pH between 5.0–6.0. The culture was allowed to grow for 24 hours in the fermentor maintaining the temperature at 26° C. The dissolved oxygen level was maintained at 30% by first controlling the air flow rate between 0.5 to 3.5 scfm, then by controlling the agitation rate from 150 to 450 rpm using a PID controller. Twenty liters of this tank were used to inoculate a 1300 liter fermentor containing 1000 liters of medium consisting of 3.5% dextrose and 1.6% yeast extract. Ammonium hydroxide and sulfuric acid were used to maintain the pH between 5.0–6.0. The culture was allowed to grow until glucose depletion in the fermentor maintaining the temperature at 26° C. The dissolved oxygen level was controlled at 30% by controlling the air flow and agitation under a PID controller. At glucose depletion, the pH of the fermentation was adjusted to 4.5 with 30% sulfuric acid and the substrate 2-methyl-3-keto-δ-valerolactone was added for a final concentration of 23.4 mmoles/L. A glucose feed was started at the delivery rate of 200 grams of glucose/hour. Three additional shots of substrate at the same concentration were added to the bioconversion tank for a total addition of 93.6 moles. The rate of the bioconversion was monitored on high pressure liquid chromatography (HPLC). The HPLC system utilized was an isocratic system at 1.0 ml min$^{-1}$ on a Phenomenex Luna C18 (2), 5 m (250×4.6 mm) with a guard column (30×4.6 mm) of the same resin using a detection at 254 nm. The solvent system is comprised of 25 mM ammonium phosphate buffer, adjusted to pH 3.5 with acetic acid/acetonitrile (95/5, v/v). Retention time of substrate is 5.5 minutes. When bioconversion was complete, the cells were removed by filtration of broth through a 6" single plate filter. Sodium chloride was added to the filtrate (20%, w/v). This solution was extracted 3 times with equal volume of acetonitrile. The aqueous layer was discarded. The organic layer is concentrated under vacuum and then the concentrate is filtered to remove salts. Isolated yield of the 2-methyl-3-hydroxy-valerolactone were 61.5 moles or 65.7%. The diastereomeric and enantiomeric purity of the (S,S) isomer of 2-methyl-3-hydroxy-valerolactone in this example were determined to be 99% and 97% respectively by utilizing gas chromatography analysis. This analysis was conducted under the following conditions Chromatograph: HP 6890 gas chromatograph Column: Astec Chiraldex B-PH analytical capillary column Temperature: 150° C., isothermal Carrier gas: He at 1.5 mL/min Injector: 200° C., split ratio=1: 200

Detector: Flame Ionization Detector (FID), 200° C. H$_2$ flow: 40 mL/min Air flow: 450 mL/min

EXAMPLE 4

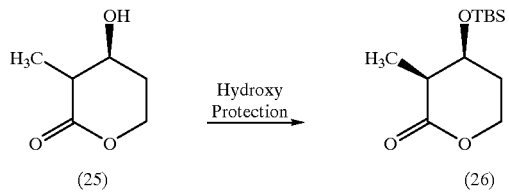

To a solution of the compound of formula (25) (6.56 g, 50.46 mmoles) in DMF (60.0 ml) at room temperature was added imidazole (13.74 g, 201.84 mmoles). After 10 minutes of stirring, t-butyldimethylsilyl chloride (15.21 g, 100.92 mmoles) and dimethylaminopyridine (0.3 g, 2.45 mmoles) were added. The reaction mixture was then stirred at room temperature overnight, and then quenched with 10% citric acid solution (80.0 ml). Extractive work up with methyl t-butyl ether (80.0 ml), drying of the organic extract with MgSO$_4$, filtration and subsequent concentration under reduced pressure afforded a light yellow oil which solidified upon equilibrating to room temperature. (26, 12.49 g; Melting point=54° C.; $^1$H NMR (CDCl$_3$) d 0.1(s,3H), 0.2(s,3H), 0.9(s,Si(C(CH$_3$)$_3$), 1.2(d, J=6.9 Hz, 3H), 1.75–1.85(m,1H), 2.05–2.10(m,1H), 2.4–2.6(m,1H), 4.08–4.15(m,1H), 4.19–4.28(m,1H), 4.4–4.6(m,1H); $^{13}$C NMR (CDCl$_3$) d 169.0, 63.79, 60.80, 37.86, 27.34, 21.36, 13.67, 8.67). The waxy material can be recrystallized from heptane at −20° C. to afford an off white product.

EXAMPLE 5

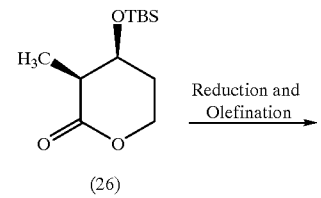

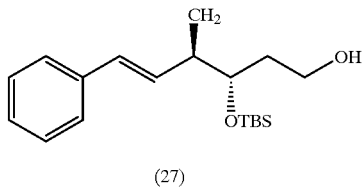

(27)

A). To a solution of the product of Example 4 (26, 37.0 g, 151.4 mmoles) in hexane (400.0 ml) at −10° C. under a nitrogen blanket was added a 1M hexane solution of DIBAL (157.0 ml, 157.0 mmoles) over a period of 30 minutes, while maintaining temperature below −10° C. The solution was stirred for another 30 minutes.

B). A separate reaction vessel was charged with benzyldiphenylphosphine oxide (79.6 g, 272.5 mmoles, Brown et al., *Tetrahedron Letters*, 35 (36), 6733 (1994)) and THF (318.0 ml). To this mixture under a nitrogen blanket was added 1.0 M solution of sodium bis(trimethylsilyl)amide (257.0 ml, 257.0 mmoles) all at once with vigorous stirring at room temperature. Reaction exothermed slightly. The reddish solution was then heated to 50° C., a solution of part A was added via canula over a period of 30.0 minutes. Reaction was then stirred for 1.25 hours at 50° C. and monitored by TLC (1:1 EtOAc/heptane). The reaction mixture was quenched by addition of solid sodium sulfate decahydrate (20.0 g) in several portions, resulting in a milky white suspension which was mixed with hexane (600.0 ml) and filtered. The filtering cake was washed with hexane (50.0 ml) and the combined filtrate was washed twice with 750 mL of 10% citric acid solution. The organic layer was then dried over MgSO$_4$, filtered and concentrated under reduced pressure to afford 51.0 g of an oil (27) with an E:Z ratio of 29:1 as determined by $^1$H NMR. $^1$H NMR (CDCl$_3$) d 0.1(s,3H), 0.2 (s,3H), 0.9 (s,SiCMe$_3$, 1.2 (d, J=6.9 Hz, 3H), 1.6–1.75 (m,2H), 2.4–2.55(m,1H), 3.60–3.7 (m,2H), 3.7–3.84 (m,1H), 6.0–6.6 (dd, J=16 Hz,8.6 Hz,1H), 6.25–6.35(d, J=16 Hz, 1H), 7.1–7.3(m,5H);$^{13}$C NMR (CDCl$_3$) d 128.11, 125.58, 124.04, 122.59, 121.37, 70.21, 56.14, 38.43, 30.72, 21.61, 14.0, 10.58, −11.0)).

EXAMPLE 6

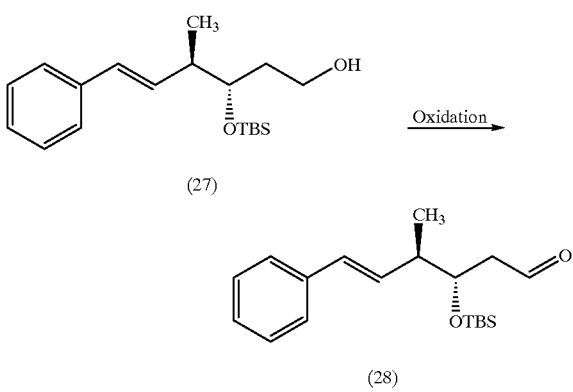

(3S,4R)-3-[(tert-butyldimethylsilyl)oxy]-4-methyl-6-phenylhex-5(E)-enal (28)

To a solution of oxalyl chloride (0.62 ml, 8.73 mmoles) and CH$_2$Cl$_2$ (20.0 ml) at −60° C. (dry ice/acetone bath) was added anhydrous DMSO via a syringe over a period of 3.0 minutes while maintaining temperature below −60° C. (gas evolution was observed and controlled by the rate of addition of DMSO). The mixture was then stirred for 15 minutes after which a solution of the product of Example 5 (27, 1.0 g, 3.12 mmoles) in CH$_2$Cl$_2$ (4.0 ml) was added over a period of 5 minutes. After 10 minutes, triethylamine (1.22 ml, 8.73 mmoles) was added and the cooling bath was removed to allow the reaction mixture to warm up to room temperature to complete the conversion as indicated by TLC (1:1 EtOAc/heptane). The reaction mixture was then quenched with 10% citric acid (20.0 ml), dried with MgSO$_4$, filtered and concentrated under reduced pressure to afford a light yellow oil (28, 1.0 g): $^1$H NMR (CDCl$_3$) d 0.1(s,3H), 0.2(s,3H), 0.9(s,Si(C(CH$_3$)$_3$), 1.2(d, J=6.9 Hz, 3H), 2.4–2.55(m,3H), 4.18–4.22(m,1H), 6.0–6.6(dd, J=16 Hz,8.6 Hz,1H), 6.25–6.35(d, J=16 Hz, 1H), 7.1–7.3(m,5H); $^{13}$C NMR (CDCl$_3$) d 189, 126, 125.5, 123.5, 121.9, 120.0, 66.0, 44.0, 38.0, 19.95, 12.5, 11.0, −11.0).

EXAMPLE 7

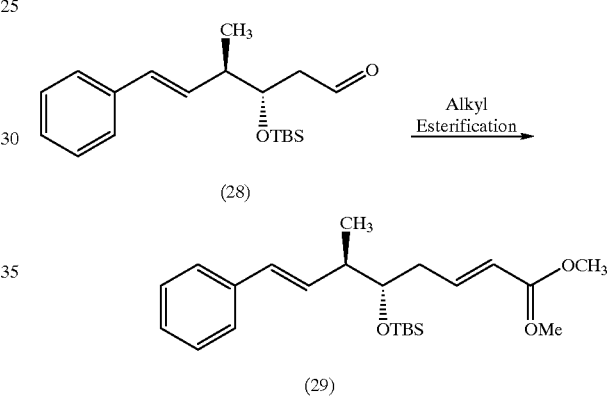

Methyl (5S,6R)-5-[(tert-butyldimethylsilyl)oxy]-6-methyl-8-phenylocta-2(E),7(E)-dienoate (29)

To a solution of the product of Example 6 (28, 14.63 g, 45.92 mmoles) and THF (60.0 ml) at room temperature was added trimethyl phosphonoacetate (8.5 ml, 52.82 mmoles) and 1,1,3,3-tetramethylguanidine (6.9 ml, 55.11 mmoles). After an hour of stirring, HPLC analysis indicated disappearance of starting material. After stirring overnight for convenience, the reaction mixture was treated with CH$_2$Cl$_2$ (150.0 ml) and water (50.0 ml). The lower organic layer was separated and washed with 1 N HCl (100.0 ml), dried over MgSO$_4$, filtered and concentrated under reduced pressure to give an red oil (29, 16.03 g): $^1$H NMR (CDCl$_3$) d 0.1(s,3H), 0.2(s,3H), 0.9(s,SiCMe$_3$), 1.2(d, J=6.9 Hz, 3H), 2.3–2.55(m, 2H), 2.36–2.44(m,1H), 3.68(s,3H), 3.69–3.73(m,1H), 5.81 (d, J=15.66 Hz,1H), 6.1(dd, J=16 Hz,8.6 Hz,1H), 6.35(d, J=16 Hz,1H), 6.3–6.6(m,1H), 7.1–7.35(m,5H); $^{13}$C NMR (CDCl$_3$) d 168.0, 142, 133.5, 127.45, 125.98, 124.03, 122.58, 118.0, 70.65, 47.06, 38.46, 33.3, 21.58, 14.1, 11.99, −11.0).

EXAMPLE 8

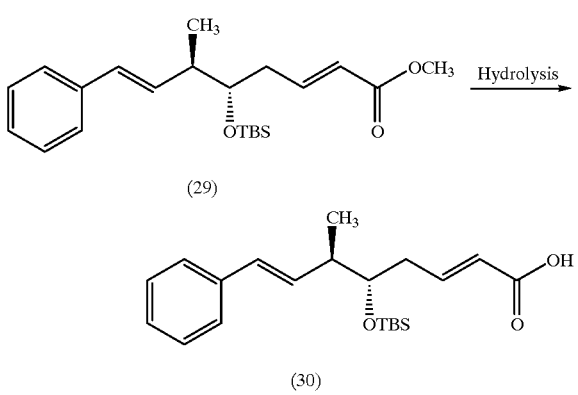

(5S, 6R) -5-[(tert-Butyldimethylsilyl)oxy]-6-methyl-8-phenylocta-2(E),7(E)-dienoic Acid (30)

To a solution of the product of Example 7 (29, 22.05 g, 58.83 mmoles) in 1,4-dioxane (118.0 ml) at room temperature was added 2 N KOH (118.0 ml, 235.3 mmoles). The solution was then heated at reflux for 2.5 hours when TLC (1:1 EtOAc/heptane) indicated no starting material was present. The reaction mixture was then allowed to warm up to temperature and quenched with 2N HCl (160.0 ml, 308.3 mmoles). Extractive work up with ethyl acetate (200.0 ml), drying over $MgSO_4$, filtration and concentration under reduced pressure afforded the title compound as a brown oil (30, 19.10 g) : $^1$H NMR ($CDCl_3$) d 0.1(s,3H), 0.2(s,3H), 0.9(s,Si(C(CH_3)_3), 1.2(d, J=6.9 Hz, 3H), 2.3–2.55(m, 2H), 2.36–2.44(m,1H), 3.7–3.8(m, 1H), 5.81(d, J=15.66 Hz,1H), 6.1(dd, J=16 Hz,8.6 Hz,1H), 6.35(d, J=16 Hz,1H), 6.3–6.6 (m,1H), 7.1–7.35(m,5H) ; $^{13}$C NMR ($CDCl_3$) d 168.0, 143.3, 142.0, 133.0, 127.35, 126.08, 124.06, 122.64, 121.61, 118.26, 70.56, 38.62, 33.33, 21.6, 14.0, 11.85).

EXAMPLE 9

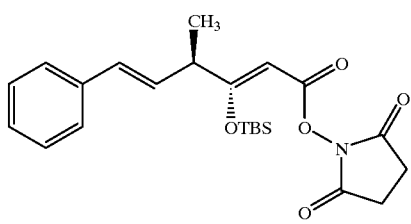

To a stirred solution of the carboxylic acid of formula (30) (720 mg, 2 mmol) in dry dimethylformamide (5.50 mL) was added 1-Ethyl-3-(3-dimethylaminopropyl)carbodiimide (459 mg, 2.4 mmol) and N-hydroxysuccinimide (299 mg, 2.6 mmol) at room temperature. The mixture was stirred for 28 h and then diluted with EtOAc (100 mL) and washed with 1N aqueous HCl (2×50 mL), $H_2O$ (75 mL), dried (MgSO4) and concentrated in vacuo to leave an oil. Crude product was purified by column chromatography (gradient elution : 5–30% EtOAc/Hexanes) to give active ester as a pale yellow oil (724 mg, 80%).

$[\alpha]_D^{589}$+71.3° (c 10.1, $CHCl_3$); $^1$H NMR ($CDCl_3$) δ7.36–7.20 (m, $PhH_5$, 3-H), 6.38 (d,J=16 Hz, 8-H), 6.14 (dd, J=16.1 and 8.0 Hz, 7-H). 6.03 (d, J=16 Hz, 2-H), 3.79 (q, J=4.3 Hz, 5-H), 2.94 (brs, $CH_2CH_2$), 2.58–2.42 (m, 6-H, 4-HH'), 1.10 (d,J=6.8 Hz, 6-Me), 0.90 (s, 9H, SiCMe3), 0.05 (s, 6H, $SiMe_2$) ppm; IR ($CHCl_3$) $\nu_{max}$ 2957, 2931, 2858, 1772, 1741, 1648, 1364, 1254, 1092, 1069, 838 cm$^{-1}$; MS (FD) 457 (M$^+$,100); Anal. calcd. for $C_{25}H_{35}NO_5$ requires: C,65.61; H,7.71; N,3.06%. Found: C,65.51; H,7.56; N, 3.02%.

EXAMPLE 10

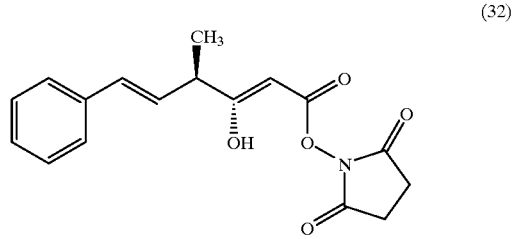

To a stirred solution of active ester of Example 9 (2.50 g,5.47 mmol) in $CH_3CN$ (130 mL) was added 48% aqueous HF (15mL) at 0 C. The solution was stirred at 0 C. for 0.75 h and then at room temperature for 4 h. The reaction was diluted with diethylether (300 mL) and washed with $H_2O$ until the wash was ~pH7. Organics were dried ($MgSO_4$) and concentrated in vacuo to give a yellow residue which was recrystallized from Et2O to give alcohol as white crystals (1.46 g,78%). $^1$H NMR ($CDCl_3$) d 7.41–7.20 (m,$PhH_5$,3-H), 6.48 (d,J=16 Hz,8-H), 6.15–6.07 (m,7-H,2-H), 3.71–3.65 (m,5-H), 2.83 (brs,$CH_2CH_2$), 2.60–2.33 (m,6-H,4-$CH_2$), 1.95 (brs, 5-OH), 1.14 (d,J=6.8 Hz,6-Me) ppm;

IR (KBr) $\nu_{max}$ 3457, 1804, 1773, 1735, 1724, 1209, 1099, 1067, 1049, 975, 744, 694 cm$^{-1}$;

UV (EtOH) $\lambda_{max}$ 250 ($\epsilon$=20535) nm;

MS (FD) 343.2 (M$^+$,100);

$[\alpha]_D$ –57.8° (c 10.56, $CHCl_3$);

Anal. calcd. for $C_{19}H_{21}NO_5S$ requires: C, 66.46; H,6.16; N,4.08%. Found: C,66.49; H,6.16; N, 4.07%.

EXAMPLE 11

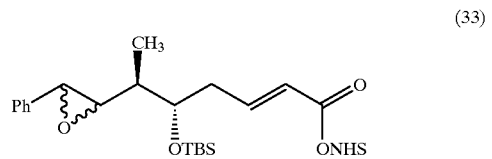

Acetone (10 mL) was added to a solution of the active ester of Example 9 (2.90 g, 6.35 mmol) in dichloromethane (20 mL) and the solution cooled to 0° C. An aqueous solution of oxone (11.7 g, 19 mmol) in $H_2O$ (30 mL) was slowly added to stirred solution of aqueous $NaHCO_3$ (5.3 g, 63.5 mmol) in $H_2O$ (30 mL) (gas evolution observed!). The resulting solution was added to the reaction mixture and stirred at 0° C. for 7 h (tlc- 50% conversion). Further oxone (6 g) and acetone (15 mL) were added and the mixture stirred for 1.5 h (tlc- all SM consumed). The reaction mixture was diluted with $H_2O$ (5 volumes) and product extracted with $CH_2Cl_2$ (5×100 mL). Combined, dried ($MgSO_4$) organics were concentrated in vacuo to give product as a yellow gummy solid (2.88 g). Tlc and $^1$H NMR indicated 90% desired epoxide product (α:β=1:1.62): 10% SM. Crude product was purified by column chromatography (SiO₂: gradient elution: 15%–25% EtOAc: Hexanes) to give recovered styrene (389 mg, 13%) and epoxide as a yellow oil (2.38 g, 80%). Epoxides (2 g, α:β=1:1.50) were separated by HPLC to give β-epoxide as a white crystalline solid (1.17 g, 59%. 99.8% de) and a-epoxide as white crystalline solid (0.864 g, 43.2%, 99% ee).

EXAMPLE 11A

Alternative Preparation (33)

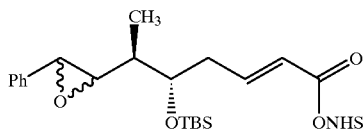

To a vigorously stirred solution of styrene (229 mg, 0.50 mmol) in acetonitrile (7.5 mL) was added 0.1M aqueous Na2EDTA (5 mL) and catalytic aqueous 0.1M tetra-n-butyl ammonium hydroxide (0.1 mL) at 0° C. A mixture of oxone (770 mg, 1.25 mmol) and sodium bicarbonate (326 mg, 3.88 mmol) were pulverized and a portion (~1/5) was added to the reaction mixture to bring the pH to ~7. After 5 min, ketone (194 mg, 0.752 mmol) was added portion wise over a 1 h period. Simultaneously, the remaining Oxone—sodium bicarbonate mixture was added over ~1 h. After the additions were completed, the reaction was allowed to be stirred at 0° C. for 4.5 h (HPLC showed styrene: epoxide 50:50 and α:β epoxide=1: 5.6). Further Oxone (380 mg) and sodium bicarbonate (170 mg) were added portionwise over 1 h and then the reaction allowed to stir for a further 3.5 h. the reaction was diluted with ethyl acetate (50 mL) and washed with water (50 mL). Organics were dried (MgSO₄) and concentrated in vacuo to give crude product as an oil (140 mg).

HPLC: Reverse phase C18 column, 70:30 CH₃CN:H₂O, flow rate 1.0 mL/min, 1=220 nm

β-epoxide Rt=6.80 min (38.3%), α-epoxide Rt=8.43 min (8.71%), styrene Rt=13.90 min (2.81%).

α:β epoxide=1:4.4 and styrene: epoxide=6:94

EXAMPLE 12

(34)

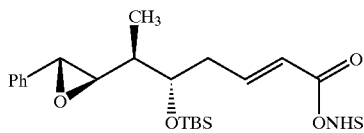

HPLC: C18 reverse phase, flow rate 1 mL/min, 60:40-CH₃CN:H₂O, $\lambda_{max}$=254 nm, β-epoxide Rt=17.2 mins (AUC 1.5); $[\alpha]_D^{589}$ +77.36 (c 1.06, CH₂Cl₂); ¹H NMR (CDCl₃) δ7.35–7.24 (m, 6H, ArH₅, 3-H), 6.08 (d, J=15.8 Hz, 2-H), 3.91–3.88 (m, 5-H), 3.70 (s, 8-H), 2.97 (dd, J=6 and 0.9 Hz, 7-H), 2.85 (s, 4H, CH₂CH₂), 2.56–2.51 (m, 4-HH'), 1.78–1.76 (m, 6-H), 1.06 (d, J=6.9 Hz, 6-Me), 0.86 (s, 6H, SiCMe₃), 0.05 (s, SiMe), 0.01 (s, SiMe) ppm; IR (CHCl₃) $v_{max}$ 2957, 2931, 1742, 1773, 1200, 1069, 839 cm⁻¹; UV (EtOH) $\lambda_{max}$ 217 (e=21180) nm; MS (FD) m/z 474 (M⁺, 10), 416 ([M−CMe₃]⁺, 100); Anal. calcd. for C₂₅H₃₅NO₆ requires: C, 63.40; H, 7.45; N, 2.96%. Found: C, 63.45; H, 7.31; N, 3.21%.

EXAMPLE 13

(35)

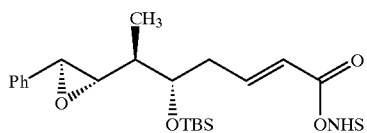

HPLC: C18 reverse phase, flow rate 1 mL/min, 60:40-CH₃CN:H₂O, $\lambda_{max}$=254 nm, α-epoxide Rt=21.0 mins (AUC 1.0); $[\alpha]_D^{589}$ +10.68° (c 1.03, CH₂Cl₂); ¹H NMR (CDCl₃) δ7.38–7.26 (m, 6H, ArH₅, 3-H), 6.13 (d, J=15.7 Hz, 2-H), 3.94–3.89 (m, 5-H), 3.60 (s, 8-H), 2.99 (dd, J=7.3 and 1.3 Hz, 7-H), 2.85 (s, 4H, CH₂CH₂), 2.76–2.71 (m, 4-H), 2.61–2.54 (m, 4-H'), 1.64 (dt, J=7.2 and 2.8 Hz, 6-H), 1.03 (d, J=7 Hz, 6-Me), 0.90 (s, 9H, SiMe₃), 0.08 (s, SiMe), 0.05 (s, SiMe) ppm; IR (CHCl₃) $v_{max}$ 2957, 2931, 1741, 1773, 1649, 1254, 1200, 1125, 1095, 1069, 891, 839 cm⁻¹; UV (EtOH) $\epsilon_{max}$ 218 ($\epsilon$=21727) nm; MS (FD) m/z 474 (M⁺, 10), 416 ([M−CMe₃]⁺, 100); Anal. calcd. for C₂₅H₃₅NO₆ requires: C, 63.40; H, 7.45; N, 2.96%. Found: C, 63.20; H, 7.63; N, 3.07%.

EXAMPLE 14

(36)

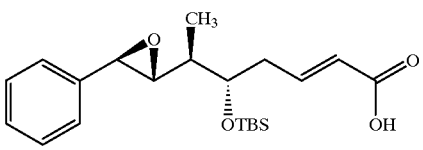

Preparation of b-Epoxy Fragment A Acid (36)

A solution of 36a (1.91 g, 5.30 mmol) of the formula:

(36a)

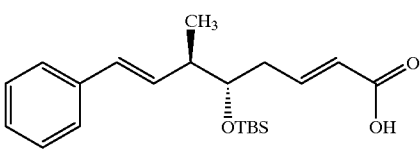

in CH₂Cl₂ (18 mL) was treated with m-chloroperbenzoic acid (0.96 g, 5.6 mmol) and the mixture stirred for 4 h before the volatiles were evaporated to give a colorless oil (2.88 g). Preparative HPLC was used to separate the epoxides (1.2:1 b:a) to give the desired b-epoxide as a colorless solid (42%). ¹H NMR (500 MHz, CDCl₃) d 7.37–7.27 (m, 5H), 7.11 (ddd, 1H, J=15.5, 7.6, 7.6 Hz), 5.92 (d, 1H, J=15.5 Hz), 3.90 (ddd, 1H, J=5.6, 5.6, 5.4 Hz), 3.70 (d, 1H, J=2.0 Hz), 3.00 (dd, 1H, J=6.6, 2.1 Hz), 2.51 (dd, 2H, J=6.5, 6.5 Hz), 1.77–1.73 (m, 1H), 1.10 (d, 3H, J=6.8 Hz), 0.89 (s, 9H), 0.07 (s, 3H), 0.03 (s, 3H). MS (FD) m/z 377 (M+1, 43), 319 (M−57, 100).

EXAMPLE 14A

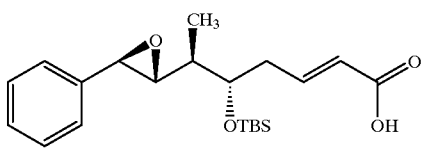

(36)

Alternate Preparation of b-Epoxy Fragment A Acid

To a stirred solution of acid 2a' (100 mg, 0.277 mmol) in CH$_3$CN (3.7 mL) at 0° C. was added a solution of Na$_2$EDTA (1×10$^{-4}$ M in H$_2$O, 2.8 mL, 0.28 mmol) and tetrabutylammonium hydroxide (1 M in MeOH, 28 mL, 28 mmol). After NaHCO$_3$ (23.3 mg, 0.277 mmol) was added, the pH was adjusted to 8.0 with 2 M NaOH and a mixture of Oxone (1.70 g, 2.77 mmol) and NaHCO$_3$ (722 mg, 8.59 mmol) prepared. A 100 mg portion of the Oxone/NaHCO$_3$ was added followed by ketone (9f) (143 mg, 0.554 mmol). The pH was immediately adjusted to 7.8–8.0 with 2 M NaOH. The rest of the Oxone/NaHCO$_3$ mixture was added in 95 mg portions in 10 min intervals and a solution of (9f) (143 mg, 0.554 mmol) in CH$_3$CN (500 mL) was added to the mixture during this period via a syringe pump. Throughout the experiment the pH was maintained at 7.8–8.0 with 2 M NaOH and 1 N H$_2$SO$_4$. HPLC analysis (C18 reverse phase, detection at 220 nm, flow rate at 1 mL/min, CH$_3$CN (0.05% TFA)/H$_2$O (0.05% TFA) –% CH$_3$CN: 80% to 90% over 10 min) 3 h after the Oxone addition revealed that the conversion was greater than 95% with a b/a epoxide ratio of 5.0:1. The mixture was filtered and the wetcake washed with CH$_2$Cl$_2$ (15 mL). The filtrate was washed with H$_2$O (15 mL) and the aqueous phase back extracted with CH$_2$Cl$_2$ (15 mL). The combined organic phases were washed with 0.1 M HCl (10 mL) and H$_2$O (10 mL), dried (MgSO$_4$), and concentrated to give the crude product[4a] as a yellow oil (104 mg, 100%).

EXAMPLE 15

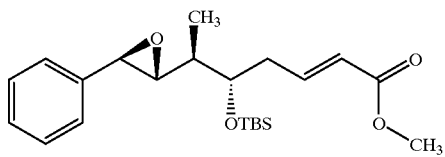

(37)

Preparation of b-Epoxy Fragment A Methyl Ester

The epoxidation of the methyl ester of formula (29) (104 mg, 0.278 mmol) was performed in the same manner as described in Example 14A except that the pH was lowered to 3.3 with 1 N H$_2$SO$_4$ after the tetrabutylammonium hydroxide was added, prior to the addition of sodium bicarbonate. HPLC analysis (same method as used for the analysis of the product of Preparation 9 except % CH$_3$CN: 95%, isocratic) 2 h after the Oxone addition revealed that conversion was greater than 95% with a b/a epoxide ratio of 4.9:1. After CH$_2$Cl$_2$ (6 mL) was added, the mixture was filtered and the wetcake washed with CH$_2$Cl$_2$ (14 mL). The filtrate was washed with H$_2$O (10 mL) and the aqueous phase back extracted with CH$_2$Cl$_2$ (2×20 mL). The combined organic phases were dried (MgSO$_4$) and concentrated to give the crude product as a yellow oil (123 mg, 113%). $^1$H NMR (500 MHz, CDCl$_3$) d 7.38–7.26 (m, 5H), 6.99 (ddd, 1H, J=15.8, 7.6, 7.6 Hz), 5.91 (d, 1H, J=15.8 Hz), 3.87 (ddd, 1H, J=5.6, 5.6, 5.4 Hz), 3.75 (s, 3H), 3.70 (d, 1H, J=2.1 Hz), 3.00 (dd, 1H, J=6.8, 2.1 Hz), 2.49–2.45 (m, 2H), 1.75–1.69 (m, 1H), 1.10 (d, 3H, J=6.8 Hz), 0.88 (s, 9H), 0.06 (s, 3H), 0.02 (s, 3H). MS (FD) m/z 391 (M+1, 8), 333 (M–57, 100).

EXAMPLE 16

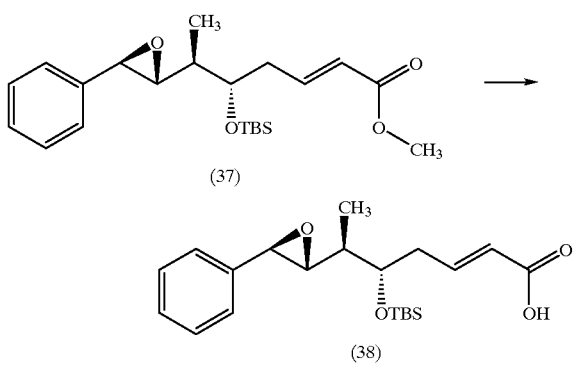

(37)

(38)

Alternate Preparation of β-Epoxy Fragment A

To a solution of the methyl ester of formula (37) (7.35 g, 18.8 mmol) in 35 mL of tetrahydrofuran was added 35 mL of 2N potassium hydroxide. The biphasic mixture was allowed to stir at 56° C. for 14 h. Upon cooling to room temperature the layers were separated and the aqueous layer was washed with t-butyl methyl ether (1×50 mL). The combined organics were washed with 1N hydrochloric acid (1×35 mL) followed by brine (1×35 mL). Drying (Na$_2$SO$_4$) with simultaneous Darco (20–40 mesh) treatment followed by filtration and concentration in vacuo provided 7.85 g of the crude acid as a brown oil.

EXAMPLE 17

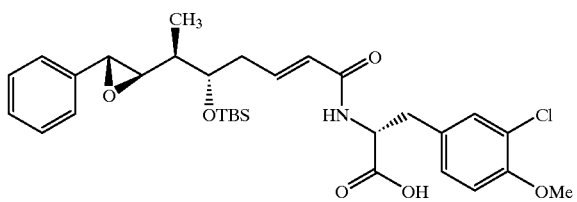

(39)

To a solution of β-epoxide of Example 12 (473 mg, 1.0 mmol) in dry DMF (6.7 mL) was added amino acid "β" (459 mg, 2.0 mmols), represented by the formula:

(39a)

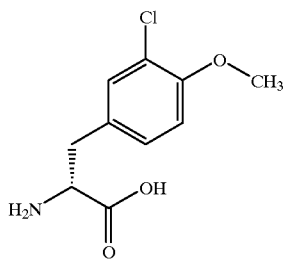

PCT Intnl. Publ. No. WO 97/07798, published Mar. 6, 1997; followed by N,O-bis-(trimethylsilyl)acetamide (618 uL, 2.5 mmols) at room temperature under a nitrogen atmosphere. The resulting mixture was heated at 55° C. (solution formed) for 8 h, diluted with EtOAc (250 mL) and washed with 1N aqueous HCl (3×80 mL), H$_2$O (100 mL). Combined, dried (MgSO$_4$) organics were concentrated in vacuo to give a yellow foam (590 mg), which further purified by column chromatography (SiO$_2$, gradient elution; CH$_2$Cl$_2$—5%–10% MeOH: CH$_2$Cl$_2$) to give silyl ether product as white foam (489 mg, 89%). $[\alpha]_D^{589}$ +28.330 (c 1.06, MeOH); $^1$H NMR (DMSO-d6)6 Unit A: 7.33–7.17 (m, ArH5), 6.55–6.40 (m, 3-H), 6.03 (d, J=15.3 Hz, 2-H), 3.83–3.76 (m, 5-H), 3.71 (s, 8-H), 2.90 (d, J=6.8 Hz, 7-H), 2.46–2.27 (m, 4-HH'), 1.50–1.44 (m, 6-H), 0.94 (d, J=6.7 Hz, 6-Me), 0.74 (s, 9H, SiMe3), −0.54 (s, SiMe), −0.13 (s, SiMe); Unit B: 7.76 (d, J=7.3, NH), 7.33–7.17 m, ArH), 7.04 (d, J=8.5, ArH), 6.90 (d, J=8.5, ArH), 4.27–4.23 (m, 2-H), 3.72 (s, 3H, OMe), 3.02 (dd, J=13.3 and 4.3 Hz, 3-H), 2.78 (dd, J=13.5 and 7.8 Hz, 3-H') ppm; IR (KBr) u 2955, 2930, 2857, 1668, 1605, 1504, 1463, 1454, 1279, 1258, 1067, 1026, 837, 776 cm$^{-1}$; UV (EtOH) 1$_{max}$ 278 (e=2219) nm.

EXAMPLE 18

(40)

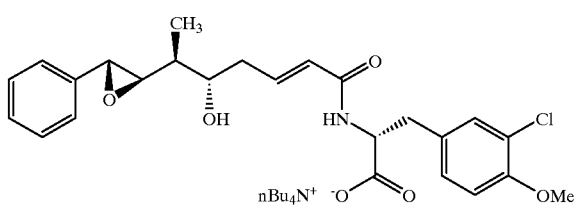

Method A

To a solution of silyl ether of Example 17 (160 mg, 0.272 mmols) in dry DMF (3.5 mL) was added sodium bicarbonate (228 mg, 2.72 mmols) followed by solid tetrabutylammonium fluoride-hydrate (TBAF)(358 mg, 1.36 mmols). The mixture was heated at 60° C. for 17 h and then further TBAF (358 mg, 1.36 mmols) and heated for 9 h and finally a solution of 1M TBAF in THF (360 uL, 1.36 mmols) added turning the reaction a brown colour. The mixture was heated for 20 mins and then the reaction quenched in water (100 mL) and extracted with EtOAc (3×50 mL). Combined, dried (Na$_2$SO$_4$) organics were concentrated in vacuo to give a brown oily gum (248 mg). Crude carboxylate salt was used in the next step without further purification.

EXAMPLE 18A (40)

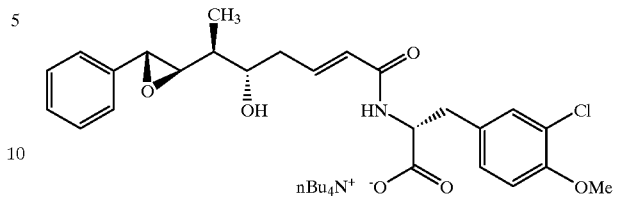

Method B

To a solution of silyl ether of Example 17 (145 mg, 0.247 mmols) in dry tetrahydrofuran (3.0 mL) was added a 1M solution of tetrabutylammonium fluoride (800 uL, 0.8 mmols) under a dry nitrogen atmosphere. The resulting solution was heated at 60° C. for 7 h and then worked-up as described above to give a brown residue (166 mg, 94%). Crude carboxylate salt was used in the next step without further purification.

EXAMPLE 19

(41)

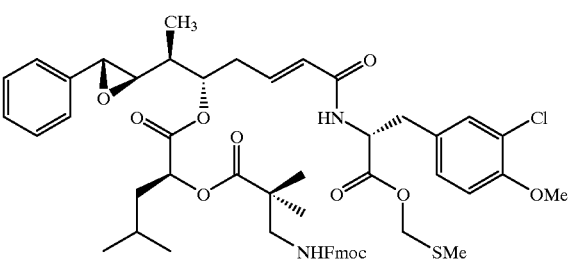

To a dry solution of crude carboxylate salt (40, 0.272 mmols) in DMSO (3.5 mL) was added sodium bicarbonate (274 mg, 3.26 mmols) followed by slow addition of a solution of t-butyl bromide (373 mg, 2.72 mmols) in DMSO (1.5 mL) over ~2 h at room temperature and under nitrogen. The mixture was stirred for a further 21 h and then quenched in brine (50 mL) and extracted with EtOAc (3×30 mL). Combined organics were washed with water (50 mL), dried (Na$_2$SO$_4$) and concentrated in vacuo to give crude ester as a gummy solid (117 mg, 81%). The crude alcohol A-B was used in the next step without further purification.

EXAMPLE 20

(42)

To a stirred solution of carboxylic acid D-C' of Preparation 2 (129 mg, 0.285 mmols) in dry dichloromethane (1.0 mL) was added DMAP (5.4 mg, 0.044 mmols) and DCC (59 mg, 0.285 mmols) at room temperature under a dry nitrogen atmosphere. The solution was stirred for 0.5 h and then solid sodium bicarbonate (37 mg, 0.44 mmols) added followed by a solution of crude alcohol A-B of Example 4 (117 mg, 0.22 mmols) in dry dichloromethane (1.2 mL). A precipitate formed within 10 mins and the mixture was stirred for a further 50 mins. The crude reaction mixture was directly applied onto a $SiO_2$ column and purified (gradient elution; 10%–40% EtOAc:Hexanes) to give methyl sulphide product as pale yellow solid (122 mg, 46% over 3 steps).

$^1$H NMR ($CDCl_3$) δ Unit A: 7.43–7.20 (m, $ArH_5$), 6.90–6.81 (m, 2H, 3-H, ArH), 5.93 (d, J=15.6 Hz, 2-H), 5.14–4.93 (m, 5-H), 3.05 (dd, J=14.5 and 8.3 Hz, 7-H), 2.65–2.63 (m, 4-HH'), 2.00–1.95 (m, 6-H), 1.17 (d, J=7.0, 6-Me); Unit B: 7.43–7.20 (m, ArH), 7.06 (d, J=8.1 Hz, ArH), 6.90–6.81 (m, ArH), 6.44 (d, J=7.7 Hz, NH), 5.19 (q, $J_{AB}$=11.8 Hz, 1'-HH), 5.14–4.93 (m, 2-H), 3.87 (s, OMe), 3.20–3.10 (m, 3-HH'), 2.21 (s, SMe); Unit C': 7.79 (d, J=7.4 Hz, $ArH_2$), 7.67 (d, J=6.9 Hz, $ArH_2$) 7.43–7.20 (m, $ArH_4$), 6.04 (d, J=7.7 Hz, NH), 4.42–4.34 (m, 3'-HH'), 4.30–4.25 (m, 4'-H, 3.42 (d, J=6.2 Hz, 3-HH'), 1.27 (s, 2-Me), 1.20 (s, 2-Me); Unit D: 5.22–5.18 (m, 2-H), 1.82–1.58 (m, 3H, 3-HH',4-H), 0.96 (s, 5-H3), 0.94 (s, 4-Me) ppm.

EXAMPLE 21

(43)

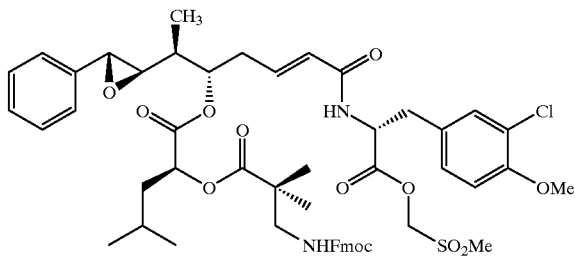

To a stirred solution of methyl sulphide of Example 20 (56 mg,0.058 mmols) in acetone (10 mL) was added sodium bicarbonate (64 mg, 0.764 mmols) followed by an aqueous solution of oxone (234 mg, 0.382 mmols) in water (3.0 mL). The reaction mixture was stirred at room temperature for 20 mins (SM is rapidly converted to a very polar component sulphoxide and then with time to the less polar sulphone product). The reaction was quenched in water (40 mL) and extracted with EtOAc (3×20 mL). Organics were washed with brine (30 mL), dried ($MgSO_4$) and concentrated in vacuo to give a solid. Crude product was purified by column chromatography ($SiO_2$: gradient elution; 25%–60% EtOAc:Hexanes) to give sulphone as a white foamy solid (43 mg, 74%).

$^1$H NMR ($CDCl_3$) δ Unit A: 7.58–7.17 (m, $ArH_5$), 6.82–6.75 (m, 3-H), 5.87 (d, J=16 Hz, 2-H), 4.98–4.86 (m, 5-H), 3.70 (d, J=1.1 Hz, 7-H), 2.92–2.89 (m,7-H), 2.61–2.58 (m,4-HH'), 1.94–1.89 (m, 6-H), 1.13 (d, J=7.1 Hz, 6-Me); Unit B: 7.58–7.17 (m, ArH), 7.04 (d, J=7.7 Hz, ArH), 6.81 (d, J=8.1 Hz, ArH), 6.54 (d, J=7.5 Hz, NH), 4.98–4.86 (m, 2-H), 3.84 (s, 7-OMe), 3.17–2.98 (dq, $J_{AB}$ =14 and 6.6 Hz, 2-HH'); Unit C': 7.75 (d, J=7.4 Hz, $ArH_2$), 7.62 (d, J=6.8 Hz, $ArH_2$), 7.58–7.17 (m, $ArH_4$), 5.97 (t, J=5.5 Hz, NH), 5.00 (s, $SO_2Me$), 4.98–4.86 (m, 2H, 1'-HH'), 4.38–4.33 (m, 3'-HH'), 4.25–4.20 (m, 4'-H), 3.40–3.36 (m, 3-HH'), 1.22 (s, 2-Me), 1.15 (s, 2-Me); Unit D: 5.19 (q, $J_{AB}$=5 Hz, 2-H), 1.80–1.61 (m, 2H, 3-H, 4-H), 1.57–1.49 (m, 3-H'), 0.91 (s, 5-$H_3$), 0.89 (s, 4-Me) ppm.

EXAMPLE 22

Cryptophycin 52

(44)

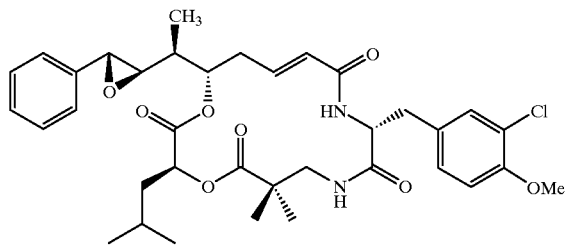

To a stirred solution of sulphone of Example 21 (18 mg, 17.98 umols) in dry DMF (2.0 mL) was added neat piperidine (8.9 uL, 90 umols) at room temperature and under nitrogen. The resulting solution was stirred for 5 h and then concentrated in vacuo to give crude amine as a foam. The amine was dissolved in toluene (3 mL) and heated at 60° C. under nitrogen for 40 mins. The reaction solution was directly purified by column chromatography ($SiO_2$; gradient elution; 20%–75% EtOAc:Hexanes) to give cryptophycin 52 as a white glass (6.1 mg, 51% over 2 steps).

$^1$H NMR ($CDCl_3$) δ Unit A: 7.45–7.38 (m, $ArH_3$), 7.31–7.23 (m, $ArH_2$), 6.85–6.76 (m, 3-H), 5.76 (d, J=15.6 Hz, 2-H), 5.27–5.23 (m, 5-H), 2.97 (dd, J=7.5 and 1.7 Hz, 7-H), 2.66–2.44 (m, 4-HH'), 1.86–1.67 (m, 6-H), 1.19 (d, J=6.9 Hz, 6-Me); Unit B: 7.31–7.23 (m, ArH), 7.09 (dd, J=8.3 and 2.0 Hz, ArH), 6.88 (d, J=8.4 Hz, ArH), 5.50 (d J=7.8 Hz, NH), 4.79 (q, J=6.4 Hz, 2-H), 3.92 (s, OMe), 3.73 (d, J=1.5 Hz, 8-H), 3.17–3.11 (m, 3-HH') ; Unit C': 3.47 (dd, J=13.4 and 8.7 Hz, 3-H), 3.17–3.11 (m, 3'-H), 1.27 (s, 2-Me), 1.20 (s, 2-Me); Unit D: 4.87 (dd, J=10 and 3.3 Hz, 2-H), 1.86–1.67 (m, 2H, 3-H, 4-H), 1.40–1.30 (m, 3-H'), 0.88 (app t, J=6.3 Hz, 6H, 5-$H_3$, 4-Me) ppm.

EXAMPLE 22A

Alternative Preparation of Cryptophycin 52

(44)

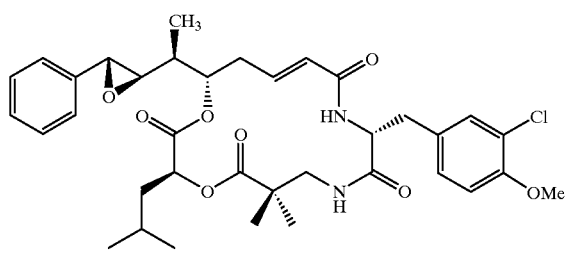

After a mixture of a compound of Example 20 (325 mg, 0.335 mmol) and piperidine (166 mL, 1.68 mmol) in DMF (34 mL) was stirred for 1 h at rt and 2 h at 60° C., HPLC (C18 reverse phase, detection at 220 nm, flow rate at 1 mL/min, $CH_3CN$ (0.05% TFA)/$H_2O$ (0.05% TFA)-% $CH_3CN$: 60% to 95% over 25 min) revealed that the Fmoc protection had been removed and a mixture of the intermediate free amine and Cryptophycin 52 was now present. 2-Hydroxypyridine (63.7 mg, 0.670 mmol) was added and the reaction allowed to stir for 18 h before it was checked again by HPLC which showed that intermediate still remained. Additional piperidine (66 mL, 0.67 mmol) was added and the reaction stirred for another 64 h at which time HPLC showed that it was done. The mixture was diluted with EtOAc (90 mL) and washed with $H_2O$ (3×90 mL). The combined aqueous phases were back extracted with EtOAc (30 mL) and the combined organic phases were dried ($MgSO_4$) and concentrated to an orange oil. Chromatography on silica gel with EtOAc/hexane (1:1 to 4:1) gave Cryptophycin 52 as a colorless solid (143 mg, 64% corrected to 58% due to contamination by N-formyl piperidine).

EXAMPLE 23

Cryptophycin 55

(45)

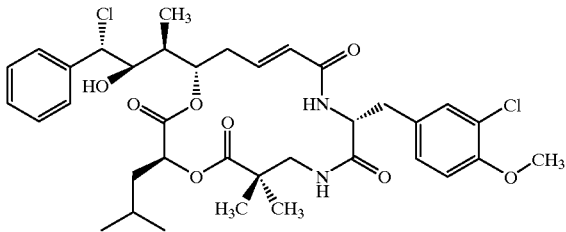

To a solution of Cryptophycin 52 (6 mg, 0.009 mol, Example 22 or 22A) in 0.6 mL of 2:1 1,2-dimethoxymethane/water was added 2 μL of 12 N HCl. The solution was allowed to stir at room temperature for 20 h, neutralized with potassium carbonate, filtered through a 5μ filter, and evaporated. The acetonitrile-soluble material was purified by reverse-phase HPLC on C18 (250×10 mm column) using 4:1 MeOH/$H_2O$ to obtain 3.0 mg of Cryptophycin 55 (48%).

$[\alpha]_D$+42.5° (c 1.1, $CHCl_3$); EIMS m/z 704/706/708 ($M^+$<1), 668/670 (1.5/0.5, $M^+$-HCl), 445(6), 226(8), 195/197(16/5), 184(10), 155/157 (33/11), 135(100), 91(99), 77(30); HREIMS m/z 668.2873 ($M^+$-HCl, $C_{36}H_{45}N_2O_8$ $^{35}$Cl, Δ-0.8 mmu); UV (MeOH)$\lambda_{max}$ (ε) 204(48400), 218 (29200), 284 (1600)nm; IR(NaCl) $\nu_{max}$ 3410, 3286, 2959, 1748, 1723, 1666, 1538, 1504, 1455, 1257, 1178, 1066, 753 $cm^{-1}$. $^1$H NMR ($CDCl_3$) δ unit A 7.35–7.42 (10-H/11-H/12-H/13-H/14-H; m), 6.78 (3-H; ddd, 15.1/10.6/4.5), 5.78 (2-H; dd, 15.1/1.7), 5.16 (5-H; ddd, 11.1/8.3/2.1), 4.65 (8-H; d, 9.7), 4.01 (7-H; bd, 9.7), 2.69 ($^4$-$H_b$; dddd, -14.5/4.5/2.1/1.7), 2.50 (6-H; bm, $W_{1/2}$≈15), 2.38 (4-$H_a$; ddd, -14.5/11.1/10.6), 1.53 (7-OH, s), 1.04 (6-Me, d, 7.1); unit B 7.21 (5-H; d, 2.2), 7.07 (9-H; dd, 8.5/2.2), 6.85 (8-H; d, 8.5), 5.57 (2-NH; d, 7.8), 4.74 (2-H; ddd, 7.8/7.6/5.2), 3.88 (7-$OCH_3$; s), 3.13 (3-$H_b$; dd, 14.5/5.2), 3.05 (3-$H_a$; dd, 14.5/7.6); unit C 7.21 (3-NH; m), 3.38 (3-$H_b$; dd, 13.5/8.3), 3.17 (3-$H_a$; dd, 13.5/4.1), 1.23 (2-$CH_3$; s), 1.17 (2-$CH_3$'; s), unit D 4.93 (2-H; dd, 10.1/3.5), 1.78 (3-$H_b$; ddd, 13.5/10.1/5.0), 1.72 (4-H; bm, $W_{1/2}$≈20), 1.43 (3-$H_a$; ddd, 13.5/8.8/3.5), 0.92 (4-$CH_3$; d, 6.6), 0.92 (5-$H_3$, d, 6.4). $^{13}$C NMR ($CDCl_3$) δ unit A 165.1 (C-1), 142.4 (C-3), 138.4 (C-9), 129.0 (C-11/13), 128.3 (C-12), 128.0 (C-10/14), 124.6 (C-2), 76.1 (C-5), 74.1 (C-7), 62.0 (C-8), 38.4 (C-6), 36.5 (C-4), 8.6 (6-Me); unit B 170.3 (C-1), 154.1 (C-7), 130.9 (C-5), 129.6 (C-4), 129.2 (C-9), 122.6 (C-6), 112.3 (C-8), 56.1 (7-OMe), 54.3 (C-2), 35.3 (C-3); unit C 177.8 (C-1), 46.5 (C-3), 42.8 (C-2), 22.9 (2-Me), 23.0 (C-2-Me'); unit D 170.3 (C-1), 71.3 (C-2), 39.7 (C-3), 24.8 (C-4), 22.7 (4-Me), 21.6 (C-5).

EXAMPLE 24

Cryptophycin 55 Glycinate Hydrochloride (46)

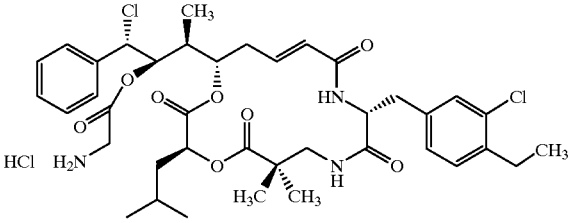

(a) Preparation of Cryptophycin 55 N-t-Boc-glycinate

To a solution of a compound of Example 23 (118 mg, 0.167 mmol), N-t-Boc-glycine (44 mg, 0.251 mmol), and 4-dimethylamino pyridine (2.0 mg, 0.0167 mmol) in 490 ml of anhydrous methylene chloride at room temperature was added a solution of 1,3-dicyclohexylcarbodiimide (52 mg, 0.251 mmol) in 67 ml of methylene chloride. After stirring for 50 min, the cloudy white reaction mixture was diluted with ethyl acetate-hexanes (3:1, 1 ml), stirred for 10 min, and filtered through a plug of celite, washing with ethyl acetate-hexanes (3:1). The filtrate and washings were concentrated in vacuo to a colorless oil. Chromatography (19 g of flash silica gel, 3:1/ethyl acetate-hexanes) afforded 138 mg (96%) of the title compound as a white foam: 500 MHz $^1$H NMR ($CDCl_3$) d 7.34 (s, 5H), 7.24 (d, 1H, J=2.0 Hz), 7.23–7.19 (m, 1H), 7.10 (dd, 1H, J=8.4, 2.0 Hz), 6.88 (d, 1H, J=8.4 Hz), 6.79–6.70 (m, 1H), 5.77 (d, 1H, J=13 Hz), 5.50 (d, 1H, J=8.0 Hz), 5.47 (d, 1H, J=9.8 Hz), 4.97 (dd, 1H, J=11, J=8.0 Hz), 4.89 (t, 1H, J=10 Hz), 4.83 (d, 1H, J=9.8 Hz), 4.79–4.72 (m, 1H), 4.68 (br s, 1H), 3.91 (s, 3H), 3.66 (dd, 1H, J=18, 5.3 Hz), 3.42–3.35 (m, 2H), 3.21 (dd, 1H, J=13, 4.0 Hz), 3.17 (dd, 1H, J=15, 5.1 Hz), 3.08 (dd, 1H, J=15, 7.6 Hz), 2.66–2.57 (m, 2H), 2.47–2.38 (m, 1H), 1.95 (ddd, 1H, J=14, 12, 4.7 Hz), 1.85–1.77 (m, 1H), 1.75–1.67 (m, 1H), 1.43 (s, 9H), 1.27 (s, 3H), 1.20 (s, 3H), 1.08 (d, 3H, J=7.0 Hz), 1.03 (d, 3H, J=6.7 Hz), 0.98 (d, 3H, J=6.5 Hz).

(b) Preparation of Cryptophycin 55 glycinate hydrochloride salt

To a solution of a compound of Example 24, step (a) (122 mg, 0.141 mmol) in 471 ml of methylene chloride at room temperature was added a 4.0 M solution of hydrogen chloride in 1,4-dioxane (178 ml, 0.707 mmol). After stirring for 1 h 20 min, the clear, colorless reaction mixture was concentrated in vacuo to provide 120 mg (99%, corrected for 7 wt % dioxane) of the title compound as a white foam: 500 MHz $^1$H NMR (MeOH-$d_4$) d 7.81 (dd, 1H, J=8.5, 2.2 Hz), 7.46–7.41 (m, 2H), 7.40–7.36 (m, 3H), 7.31 (d, 1H, J=2.1 Hz), 7.20 (dd, 1H, J=8.4, 2.1 Hz), 7.01 (d, 1H, J=8.4 Hz), 6.70 (ddd, 1H, J=15, 13, 3.7 Hz), 5.97 (dd, 1H, J=15, 1.7 Hz), 5.55 (d, 1H, J=9.9 Hz), 5.18 (d, 1H, J=9.9 Hz), 5.14 (dd, 1H, J=10, 2.8 Hz), 4.84 (t, 1H, J=10 Hz), 4.52 (dd, 1H, J=11, 3.7 Hz), 3.87 (s, 3H), 3.78 (d, 1H, J=18 Hz), 3.50 (dd, 1H, J=13, 9.8 Hz), 3.23 (d, 1H, J=18 Hz), 3.20 (dd, 1H, J=14, 3.6 Hz), 3.13 (dd, 1H, J=13, 2.4 Hz), 2.80–2.69 (m, 3H), 2.41–2.32 (m, 1H), 1.99–1.92 (m, 1H), 1.91–1.81 (m, 2H), 1.25 (s, 3H), 1.20 (s, 3H), 1.12 (d, 3H, J=7.0 Hz), 1.06 (d, 3H, J=6.2 Hz), 1.04 (d, 3H, 6.2 Hz).

Preparation 6

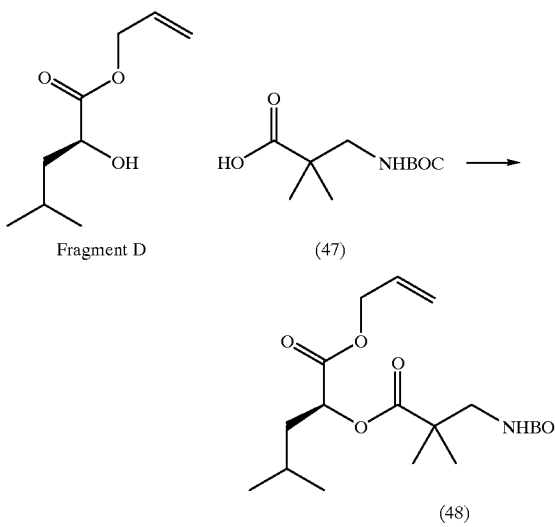

Fragment D        (47)

Allyl (2S)-2-[[3-[tert-Butoxycarbonyl)amino]-2'-dimethylpropanoyl]oxy]-4-methylpentanoate (48)

To a solution of 1,1'-carbonyldiimidazole ("CDI", 1346 g, 8.30 mol) in 3 L of THF was added a solution of compound 47 (1803 g, 8.3 mol) in 4 L of THF over 30 min. The reaction was stirred for 2 h at which time NMR analysis showed complete reaction of compound (47). Fragment D (1450 g, 7.54 mol) was added as a solid, and the reaction mixture was heated to approximately 70° C. for 16 h. The reaction mixture was cooled to 25° C. and concentrated in vacuo to give a suspension. Heptane (4 L) was added, and the mixture was extracted with 0.2 N HCl solution (6 L) to remove imidazole. The aqueous layer was extracted with 2 L of heptane. The combined organic layers were extracted successively with 0.2 N HCl solution (3 L), deionized water (3 L), and brine (3 L). The organic layer was dried (sodium sulfate) and concentrated in vacuo to give 2984 g of compound (48) as an oil. $^1$H NMR (CDCl$_3$, 500 MHz) δ0.94 (d, 3H, J=8.4 Hz), 0.98 (d, 3H, J=8.4 Hz), 1.27 (d, 6H, J=5 Hz), 1.45 (s, 9H), 1.71 (m, 3H), 3.31 (m, 2H), 4.66 (m, 2H), 5.1 (m, 1H), 5.3 (m, 3H), 5.9 (m, 1H). $^{13}$C NMR (CDCl$_3$, 75 MHz) δ176.4, 170.7, 156.4, 131.5, 119.1, 78.9, 70.9, 66.0, 48.7, 44.0, 39.6, 28.4, 24.9, 23.1, 23.0, 22.3, 21.6. IR (CHCl$_3$) 3398, 2964, 1739, 1720, 1511, 1472, 1366, 1266, 1252 cm$^{-1}$. MS {FD$^+$} m/z (relative intensity) 371 (100).

Preparation 7

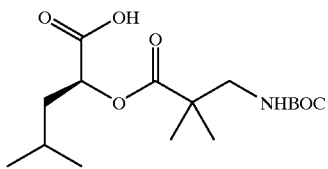

(49)

To a solution of the (48), obtained supra, in 8 L of THF was added Pd(PPh$_3$)$_4$ (3.0 g, 2.6 mmol). Morpholine (800 mL, 9.15 mol) was then added dropwise over 30 min at 15–25° C., and the reaction was then stirred at that temperature for 1.5 h. The reaction mixture was concentrated in vacuo to an oil, which was dissolved in 6 L of heptane. The heptane solution was extracted with 1 N HCl (9.8 L). The aqueous layer was back-extracted with 2 L of heptane. The combined organic layers were washed with 3 L of brine, dried (sodium sulfate), and filtered. The filtrate was stirred at room temperature and seeded with 200 mg of compound (49). The product crystallized, and the slurry was stirred for 64 h (4 h is sufficient). The slurry was cooled to 0–10° C. for 3.5 h and filtered. The filter cake was washed with cold heptane (2×500 mL) and vacuum dried at 45–50° C. to give 2324 g (93% overall yield from Fragment D) of compound (49) as a white solid, mp 70–73° C.

Preparation 7A

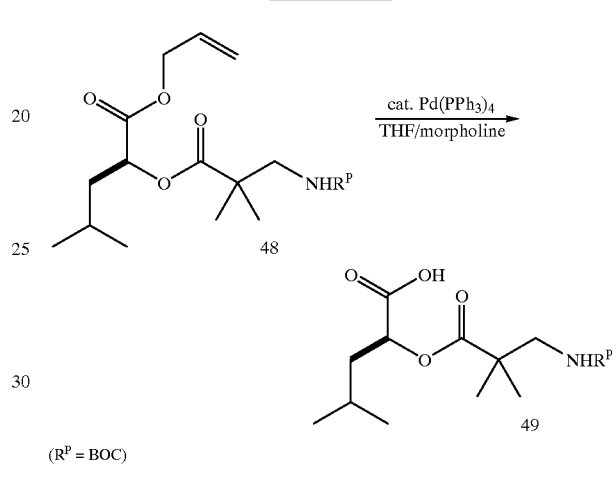

(R$^P$ = BOC)

(2S)-2-[[3'-[(tert-Butoxycarbonyl)amino]-2',2-dimethylpropanoyl]oxy]-4-methylpentanoic Acid (49)

A three-neck flask with an overhead stirrer was charged with compound (48) (23.92 g, 64.5 mmol), Pd(PPh$_3$)$_4$ (149 mg, 0.13 mmol), and dry THF (100 mL). The mixture was cooled to 8° C. under nitrogen. Morpholine (6.8 mL, 77.4 mmol) in 10 mL of THF was add dropwise over 10 min. No exotherm was observed. The cooling bath was removed, and the solution was stirred for 1 h. The solvent was then removed from the reaction mixture under vacuum. The resulting viscous oil was dissolved in 250 mL of hexane, and 70 mL of 0.01N HCl was added. Then, 1N HCl (77 mL) was added dropwise over 5 min. A small amount of yellow precipitate formed at the interface. The layers were separated, and the aqueous layer was extracted with 100 mL of hexane. The combined hexane layers were filtered to remove residual palladium complexes, dried with sodium sulfate, and concentrated in vacuo to obtain 21.3 g of (49) as a very viscous oil. (The NMR spectrum showed 6% (by weight) hexane in the oil; corrected yield of (49)=94%.) [α]$_D$=−34.2° (c 0.032, CHCl$_3$). $^1$H NMR (CDCl$_3$, 500 MHz) δ0.97 (d, J=6.3, 3H), 0.99 (d, J=6.3 Hz, 3H), 1.22 (d, J=9.0 Hz, 6H), 1.43 (s, 9H), 1.75 (m, 3H), 3.31 (m, 2H), 5.09 (dd, J=9.7, 3.4 Hz, 1H), 5.5 (bs, 0.7H), 6.16 (bs, 0.3H), 10.5 (bs, 1H). $^{13}$C NMR (CDCl$_3$, 75 MHz) δ176.6, 175.6, 156.8, 79.4, 70.6, 48.6, 44.0, 39.6, 28.4, 24.9, 23.1, 22.2, 21.5. IR (CHCl$_3$) 3691, 2963, 1710, 1512, 1151 cm$^{-1}$. MS {FD$^+$} m/z (relative intensity) 332 (100). Anal. Calcd. for C$_{16}$H$_{29}$NO$_6$: C, 57.99; H, 8.82; N, 4.23. Found: C, 58.05; H, 8.72; N, 4.13.

TABLE 1

Preparation of Fragment CD Intermediates

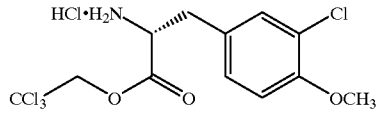

| R | Conditions | % Yield |
|---|---|---|
| methyl | CDI, 0.1N THF, 17h reflux | 94 |
| ethyl | CDI, 1N THF, 72h reflux | 78 |
| spirocyclopentyl | CDI, 0.1N THF, 17h reflux | 55 |
| spirocyclohexyl | CDI, 0.1N THF, 17h reflux | 19 |
| benzyl | CDI, 0.1N THF, 17h reflux | 21 |
| n-propyl | CDI, 0.1N THF, 17h reflux | 0 |
| n-propyl | CDI, 0.4N PhMe, 17h reflux | 59* |
| i-butyl | CDI, 0.4N PhMe, 17h reflux | 52* |

*About 50%/wt unknown impurities

Preparation 8

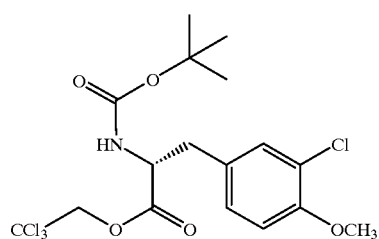

Preparation of 3-(3-Chloro-4-methoxyphenyl)-D-alanine 2,2,2-trichloroethyl ester hydrochloride salt (50)

To a 1000-mL 3-necked flask fitted with a calcium chloride drying tube and a mechanical stirrer and containing a solution of a compound of the formula:

(51)

(46.2 g, 100 mmol) in 370 mL of ethyl acetate was added a solution of hydrochloric acid in ethyl acetate (ca. 4.5 M, 800 mmol). After stirring for 19 h at room temperature, the resulting thick white reaction was cooled to 0° C. and filtered. The collected solid was washed with cold ethyl acetate (1×90 mL) followed by drying in vacuo at 40° C. to provide 36.9 g (93%) of compound (50) as a white powder: mp 217–219° C.; [a]+3.1° (c 1.21, MeOH); IR (KBr) 2830 (m), 1755 (s), 1502 (s), 1282 (s), 1258 (s), 1229 (s), 814 (s) cm$^{-1}$; 500 MHz $^1$H NMR (DMSO-d$_6$) δ8.88 (br s, 3H), 7.45 (d, 1H, J=2.0 Hz), 7.28 (dd, 1H, J=8.5, 2.0 Hz), 7.11 (d, 1H, J=8.5 Hz), 5.01 and 4.96 (AB quartet, 2H, J=12.2 Hz), 4.48 (t, 1H, J=6.6 Hz), 3.84 (s, 3H), 3.23 (dd, 1H, J=14.4, 5.9 Hz), 3.17 (dd, 1H, J=14.4, 7.3 Hz); 125 MHz $^{13}$C NMR (DMSO-d$_6$) d 168.8, 154.7, 131.8, 130.3, 128.4, 121.9, 113.8, 95.2, 75.1, 57.0, 53.8, 35.3. Anal. calcd. for C$_{12}$H$_{14}$Cl$_5$NO$_3$: C, 36.26; H, 3.55; N, 3.52. Found: C, 36.24; H, 3.59; N, 3.44.

EXAMPLE 25

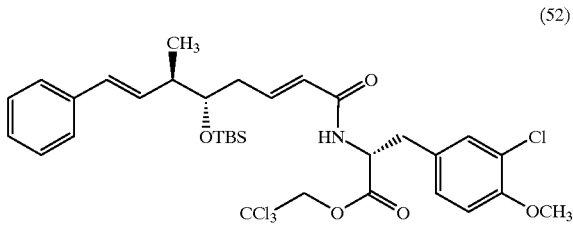

[5S-(2E,5R*,6S*,7E)]-3-chloro-N-[5-[[(1,1-dimethylethyl)dimethylsilyl]oxy]-6-methyl-1-oxo-8-phenyl-2,7-octadienyl]-O-methyl-2,2,2-trichloroethyl ester D-Tyrosine (52)

A solution of (5S,6R)-5-[(tert-butyldimethylsilyl)oxy]-6-methyl-8-phenylocta-2 (E), 7 (E)-dienoic acid (30) (551 mg, 1.53 mmol) in 3.1 mL of DMF was treated with N,N-diisopropylethylamine (799 mL, 4.58 mmol). Upon cooling to 0° C., the mixture was treated with diphenylphosphinic chloride (306 mL, 1.60 mmol). After the reaction was stirred at 0° C. for 5 min and at room temperature for 30 min, hydrochloride salt (50) (668 mg as a solid, 1.68 mmol) was added over ca. 3 min. The mixture was allowed to stir for 1 h 15 min at which time the reaction was poured onto 20 mL of water and washed with diethyl ether (2×20 mL). The combined organic extracts were washed with 1N hydrochloric acid (1×10 mL). The acid wash was extracted with diethyl ether (1×10 mL); and the combined organic extracts were dried (MgSO$_4$), filtered, and concentrated in vacuo to a yellow oil. Chromatography on 55 g of flash silica gel, eluting with ethyl acetate:hexanes (1:4), afforded 903 mg (84%) of compound (52) as a faint yellow foam.

EXAMPLE 25A

Alternate Preparation of [5S-(2E,5R*,6S*,7E)]-3-chloro-N-[5-[[(1,1-dimethylethyl)dimethylsilyl]oxy]-6-methyl-1-oxo-8-phenyl-2,7-octadienyl]-O-methyl-2,2,2-trichloroethyl ester D-Tyrosine (52)

A solution of acid (30) (130 mg, 0.361 mmol) in 720 µL of DMF was treated with N,N-diisopropylethylamine (188 µL 1,08 mmol), followed by diphenyl chlorophosphate (82 µL , 0.396 mmol). After the mixture had stirred for 1 h, hydrochloride salt (50) (157 mg, 0.395 mmol) was added as a solid. The mixture was allowed to stir for 2 h 45 min at which time the reaction was diluted with diethyl ether (15 ml) and washed with 1N hydrochloric acid (10 mL), saturated sodium bicarbonate solution (10 mL), and brine (10 mL). The organic phase was dried (MgSO$_4$), filtered, and concentrated in vacuo to a yellow oil. Chromatography on 15 g of flash silica gel, eluting with ethyl acetate:hexanes (1:2), afforded 199 mg (78%) of compound (52) as a faint yellow oil.

EXAMPLE 26

(53)

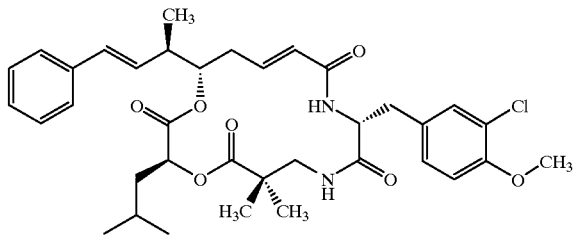

Preparation of Cryptophycin 51 (Compound 53)

To a solution of the cryptophycin seco-acid of formula:

(53a)

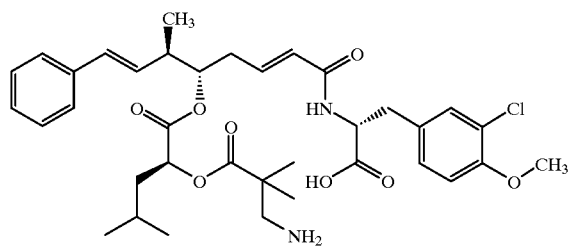

(671 mg, 0.963 mmol) in 10 mL of DMF was added N,N-diisopropylethylamine (503 mL, 2.89 mmol), followed by diphenylphosphinic chloride (202 mL, 1.06 mmol). After being stirred at room temperature for 3 h, the reaction was diluted with ethyl acetate (50 mL) and washed successively with water (1×25 mL), 1 N HCl (1×25 mL), saturated aqueous NaHCO$_3$ (1×25 mL), and brine (1×25 mL). Each aqueous layer was washed with ethyl acetate (1×25 mL). The combined organic extracts were dried (Na$_2$SO$_4$), filtered, and concentrated in vacuo to a crude solid residue which was diluted with ethyl acetate. After standing at room temperature overnight, the mixture was filtered to provide 188 mg (30%) of Cryptophycin 51 (53) as a white solid. The filtrate was chromatographed over flash silica gel, eluting with ethyl acetate:hexanes (2:1 followed by 3:1) to afford another 304 mg (48%) of compound (53).

Preparation 9 a) Preparation of Ethyl 2-cyano-2,2-dimethylpropanoate (54).

Cesium carbonate (4324 g, 13.27 mol) and DMF (2.25 L) were added to a 22 L flask with an overhead stirrer. Methyl iodide (2828 g, 19.9 mol), was added and the mixture was cooled to −10° C. under nitrogen. Ethyl cyanoacetate (750 g, 6.63 mol) was added over 30 min, keeping the reaction temperature below 30° C. The cooling bath was removed, and the reaction mixture was stirred for 2 h. The reaction mixture was then filtered, and the salt cake was washed with 6 L of methyl tert-butylether (MTBE). The filtrate was combined with 3 L of 0.1N HCl and the layers were separated. The aqueous layer was extracted with 3 L of MTBE. The combined organic layers were washed with 5% LiCl solution (2×3 L), dried with sodium sulfate, and concentrated via distillation at atmospheric pressure to give compound (54) as a light yellow oil. The oil was vacuum distilled at 50–60° C., 10 mm Hg to give 882 g (94% yield) of (54) as a colorless oil. $^1$H NMR (CDCl$_3$, 500 MHz) δ1.32 (t, 3H), 1.60 (s, 6H), 4.26 (m, 2H). $^{13}$C NMR (CDCl$_3$, 75 MHz) δ169.8, 120.9, 62.9, 38.7, 31.7, 24.9, 14.1. IR (CHCl$_3$) 3021, 2994, 2944, 2909, 2877, 2247, 1743, 1469, 1388, 1369, 1266, 1156 cm$^{-1}$. MS {FD$^+$} m/z (relative intensity): 142.1 (100). Anal. Calcd for C$_7$H$_{11}$NO$_2$: C, 59.56; H, 7.85; N, 9.92. Found: C, 58.90; H, 7.39; N, 10.00.

b) Preparation of Ethyl 3-[(tert-butoxycarbonyl)amino]-2,2-dimethylpropanoate (54a).

To a 500 mL stainless steel autoclave were charged 5% rhodium on alumina (2.5 g), BOC anhydride (8.4 g, 38.5 mmol), compound (54) (5.0 g, 35.4 mmol) and THF (140 mL). The stirred mixture was placed under 60 psi hydrogen at 70° C. After 16 h, an NMR spectrum of the reaction mixture showed the reaction was complete. The reaction mixture was allowed to cool to 25° C., vented, and purged with nitrogen. The mixture was then filtered through a Celite pad and concentrated in vacuo to give 8.64 g (99% crude yield) of compound (54a) as an oil. $^1$H NMR (CDCl$_3$, 500 MHz) δ1.06 (s, 6H), 1.15 (t, 3H), 1.32 (s, 9H), 3.1 (d, 2H), 4.05 (m, 2H), 5.0 (bs, 1H). $^{13}$C NMR (CDCl$_3$, 300 MHz) δ177.3, 156.3, 79.2, 60.8, 48.4, 43.7, 28.5, 23.1, 14.3. IR (CHCl$_3$) 3691, 3457, 2983, 2936, 2875, 1714, 1602, 1509, 1473, 1367, 1312, 1240, 1155 cm$^{-1}$. MS {FD$^+$} m/z (relative intensity) 245.2 (100). Anal. Calcd. for C$_{12}$H$_{23}$NO$_4$: C, 58.75; H, 9.45; N, 5.71. Found: C, 58.40; H, 8.95; N, 5.65.

Preparation 10

(55)

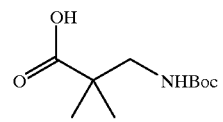

To Compound 54a (164.2 g, approximately 670 mmol) was added 1.4 L of 5N NaOH, and the mixture was stirred under a nitrogen atmosphere until homogeneous (48 h). CH$_2$Cl$_2$ (1.3 L) was added, and the mixture was cooled to 10° C. The pH of the aqueous layer was adjusted to 3 by adding (dropwise) IL of 6N HCl followed by 400 mL of IN HCl. The temperature was maintained below 20° C. The mixture stirred for 20 min, and the layers were separated. The aqueous layer was extracted with 1 L of CH$_2$Cl$_2$. The organic layers were combined, dried over Na$_2$SO$_4$ and concentrated in vacuo to give 116.8 g of a crude yellow solid. The solid was stirred in 400 mL of hexane for 4 h. The slurry was filtered and the solid dried to give 114.7 g (78% yield) of compound (55) as a white solid, mp 115–16°C. $^1$H NMR (CDCl$_3$, 500 MHz) δ 1.23 (s, 6H), 1.48 (s, 9H), 3.26 (bs, 2H), 5.09 (bs, 0.7 H), 6.41 (bs, 0.3 H), 11.68 (bs, 1H). $^{13}$C NMR (CDCl$_3$, 75 MHz) δ183.3, 181.7, 158.5, 156.4, 81.6, 79.6, 49.7, 48.1, 44.1, 43.7, 28.5, 23.0. IR (CHCl$_3$)

3315, 3004, 2542, 1895, 1700, 1648, 1414, 1367, 1350, 1278, 1157. MS {FD$^+$} m/z (relative intensity) 173 (19), 218 (100). Anal. Calcd for $C_{10}H_{19}NO_4$: C, 55.28; H, 8.81; N, 6.45. Found: C, 55.33; H, 8.59; N, 6.33.

Preparation 11

Large Scale Preparation a) Compound 54a

To a 10 gallon stainless steel autoclave were charged 5% rhodium on alumina (390 g), BOC anhydride (1363 g, 6.25 mol), compound 54 (779 g, 5.52 mol), and THF (20 L). The stirred mixture was placed under 60 psi hydrogen at 70° C. After 22 h, an NMR spectrum of the reaction mixture showed 83% conversion to 54a. Additional 5% rhodium on alumina catalyst (195 g) was added. The hydrogenation was continued for another 4 h, at which time NMR assay of the reaction mixture showed 98% conversion. The reaction mixture was allowed to cool to 25° C., vented, and purged with nitrogen. The mixture was then filtered through a multi-plate filter and concentrated in vacuo to give 1173 g (87% yield) of compound 54a as an oil, which was used directly in the next step.

b) Preparation of 3-[(tert-Butoxycarbonyl)amino]-2,2-dimethylpropanoic acid (55).

Two 22 L flasks were each charged with compound 54a (583 g, 2.38 mol), LiOH.H$_2$O (204.5 g, 4.87 mol), THF (5.7 L), and water (4.75 L). The reaction mixtures were heated to 64° C. for 19 h. The mixtures were then cooled to 10° C. with an ice bath. Approximately 1 L of 6N HCl was added to each reaction mixture to bring the pH to 3–3.5. Each mixture was combined with 2.9 L of CH$_2$Cl$_2$, and the aqueous layers were separated. The aqueous layers were extracted with another 1.5 L portion of CH$_2$Cl$_2$. The combined organic layers were dried with sodium sulfate and concentrated in vacuo to give a white solid. The solid was slurried in 5 L of heptane for 1 h, filtered, and vacuum dried to give 830 g (80% yield) of compound 55 as a white solid, mp 114–116° C. Anal. Calcd for $C_{10}H_{19}NO_4$: C, 55.28; H, 8.81; N, 6.45. Found: C, 55.55; H, 8.77; N, 6.56.

EXAMPLE 27

(53)

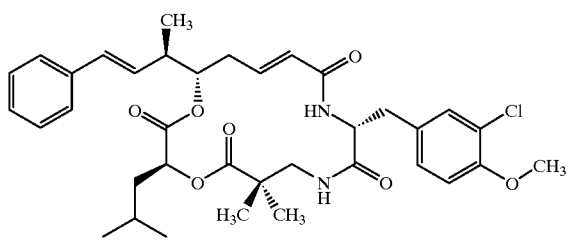

Alternate Preparation of Cryptophycin 51
(Compound 53)

(53b)

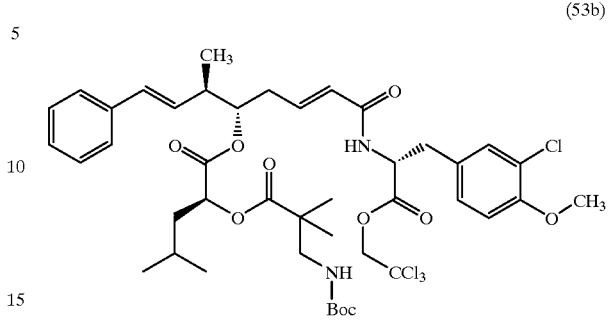

Compound (53b) (10.2 g, 11.2 mmol, Barrow, R. A. et al., J. Am. Chem. Soc. 117, 2479 (1995)) was cooled to 0° C. and dissolved in trifluoroacetic acid (TFA) (50 mL). The resulting solution was stirred at 0° C. for 30 min and was then concentrated under reduced pressure. The resultant syrup was diluted with toluene (250 mL) and washed with 1N NaOH (2×100 mL) using brine (50 mL) to break up emulsions. The aqueous extracts were back-extracted with fresh toluene (1×50 mL) and the organic phases were combined and dried (MgSO$_4$). TLC analysis indicated no trace of starting material (53b). The filtered solution of amino ester (53a) was diluted to 500 mL and 2-hydroxypyridine (5.34, 56.2 mmoles) was added. The resulting clear, pale yellow solution was allowed to stir at room temperature for 14 h. The reaction mixture became turbid so the suspension was diluted with CH$_2$Cl$_2$ (250 mL) to assure solubility of product. The mixture was washed with saturated, aqueous NaHCO$_3$ (3×100 mL) and brine (1×100 mL). The aqueous extracts were back-extracted with CH$_2$Cl$_2$ (1×100 mL) and the organic extracts were combined, dried (MgSO$_4$), and concentrated to a thick syrup. A solution of hexanes and EtOAc (100 mL, 1:1 v/v) was added and the solution was cooled to 0° C. Spontaneous crystallization occurred after 30 min. The mixture was filtered, and the filtrate was concentrated and induced to crystallize two additional times. The collected crops were combined to give 5.04 g (69%) of compound (53) (Cryptophycin 51) as a white powder. HPLC (85:15 CH$_3$CN/H$_2$O, 0.05% TFA in both organic and aqueous phases; flow 1 mL/min; wavelength: 225 nm; column: Zorbax SB-C18) R$_t$=6.09 min 95% pure. $^1$H NMR (300 MHz, CDCl$_3$) d 7.32–7.17 (m, 8H); 7.04 (dd, 1H, J=2.2, 8.4); 6.82 (d, 1H, J=8.5); 6.76 (m, 1H); 6.39 (d, 1H, J=15.9); 5.99 (dd, 1H, J=8.8, 15.8); 5.73 (dd, 1H, J=2.3, 16.4); 5.50 (d, 1H, J=7.8); 5.03 (m, 1H); 4.83 (dd, 1H, J=3.3, 9.9); 4.73 (ABq, 1H, J=6.4); 3.86 (s, 3H); 3.39 (dd, 1H, J=8.6, 13.5); 3.10 (m, 2H); 2.53 (m, 2H); 2.36 (m, 1H); 1.62 (m, 3H); 1.21 (s, 3H); 1.14 (s, 3H); 1.11 (d, 3H, J=6.9); 0.71 (app. t, 6H, J=6.0).

EXAMPLE 28

Alternative Preparation of Cryptophycin 55
(Compound 45)

A solution of the olefin cryptophycin 51 (Compound 53) (2.15 g, 3.29 mmol) in CH$_2$Cl$_2$ (11 mL) was cooled to 0° C. under nitrogen. m-CPBA (596 mg, 3.45 mmol) was added, and the solution was allowed to stir at 0° C. for 30 min, then at room temperature for 19.5 h. The reaction mixture was then diluted with CHCl$_3$ (55 mL) and cooled to −60° C. Chlorotrimethylsilane (TMS-Cl) (1.67 mL, 13.2 mmol) was then added dropwise, and the resulting mixture was stirred at the same temperature for 45 min. Another aliqout of TMS-Cl was added with continued stirring for a further 1.5 h. The reaction mixture was concentrated to dryness in vacuo and flash chromatographed over $SiO_2$ with hexane:EtOAc (1:1 to 1:2 to 1:3). Cryptophycin 55 (Compound 45) was isolated as a white foam, 1.18 g, 51%.

EXAMPLE 29

(56)

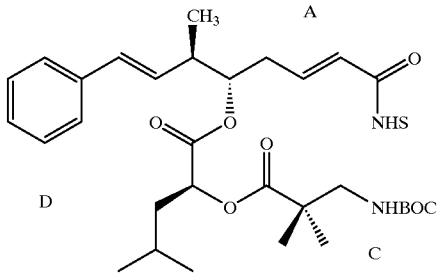

To a suspension of carboxylic acid (49) (1.28 g, 3.87 mmol), in dry dichloromethane (6 mL) was added EDCI (742 mg,3.87 mmol) and DMAP (73 mg,0.60 mmol), and the mixture was stirred at room temperature for 0.5 h. A solution of active ester (32) (1.02 g, 2.97 mmol) in dichloromethane (5.5 mL) was added to the reaction mixture and stirred for a further 0.3 h. The reaction was diluted with $CH_2Cl_2$ (200 mL) and washed with 1N aq. HCl (2×50 mL), sat. aq. $NaHCO_3$ (2×50 mL) and $H_2O$ (50 mL). The organics were dried ($MgSO_4$) and concentrated in vacuo to leave an oily residue, which was purified by column chromatography (gradient: 10–30% EtOAc/hexanes) to give the desired ester (56) as a yellow solid (1.68 g,79%)

$^1$H NMR (CDCl$_3$) unit A d 7.35–7.20 (m,PhH$_5$,3-H), 6.43 (d,J=15.8 Hz,8-H), 6.12 (d,J=15.9 Hz,2H), 5.99 (dd,J=8.5 and 15.8 Hz,7-H), 5.06–5.08 (m, 5-H), 2.85 (brs,CH$_2$CH$_2$), 2.68–2.61 (m,6-H,4—CH$_2$), 1.13 (d,J=6.8 Hz,6-Me); unit C d 5.31 (brt,NH),3.28–3.25 (m,3-CH$_2$),1.43 (s,CMe$_3$), 1.21 (s,2-Me), 1.19 (s,2-Me); unit D d 4.95 (dd,J=9.8 and 3.8 Hz,2-H), 1.73–1.64 (m,3-H,4-H), 1.59–1.49 (m,3-HI), 0.85 (d,J=6.4 Hz,5-Me), 0.82 (d,J=6.4 Hz,4-Me) ppm;

IR γ (KBr) 3400, 2975,1743,1367,1206,1126,1145,1068 cm$^{-1}$; MS (FD) 657 (M$^+$,100);

$[\alpha]_D$+39.5° (c 10.38, CHCl$_3$);

Anal. calcd. for $C_{35}H_{48}N_2O_{10}$ requires: C,64.01; H,7.37; N,4.27%. Found: C,64.19; H,7.27; N,4.52%.

EXAMPLE 30

(57)

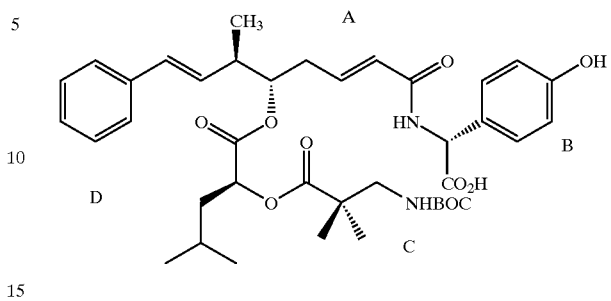

To a stirred solution of active ester (56) (150 mg, 0.229 mmol) in dry DMF (2.5 mL) was added bis(trimethylsilyl)-acetamide (BSA) (282 µL,1.143 mmol) followed by D-hydroxy-phenylglycine (57 mg, 0.343 mmol). The mixture was heated in a sealed tube under $N_2$ at 55° C. for 20 h. The reaction solution was diluted with EtOAc (180 mL) and washed with 1N aq. HCl (50 mL), $H_2O$ (50 mL), brine (50 mL), dried ($MgSO_4$) and concentrated in vacuo to give a yellow solid. Purification of the crude solid by column chromatography (gradient: 5–20% MeOH/CH$_2$Cl$_2$) provided the Boc-amine (57) (122 mg,75%).

$^1$H NMR (CD$_3$OD/CDCl$_3$) Unit A d 7.27–7.20 (m,PhH$_5$), 6.75–6.69 (m,3-H), 6.43 (d,J=15.9 Hz,8-H), 5.96 (d,J=15.7 Hz,7-H), 5.93 (d,J=15.6 Hz,2-H), 4.95–4.93 (m,5-H), 2.56–2.49 (m,6H,4—CH$_2$), 1.04 (d,J=6.8 Hz,6-Me); Unit B d 7.16 (d,J=8.3 Hz,ArH$_2$), 6.66 (d,J=8.2 Hz,ArH$_2$), 5.62 (brt, NH), 5.19–5.18 (m,2-H); Unit C d 3.15 (d,J=6.3 Hz,3—CH$_2$), 1.36 (s,CMe$_3$), 1. 11 (s,2-Me), 1.08 (s,2-Me); Unit D d 4.85 (dd,J=9.6 and 3.3 Hz,2-H), 1.64–1.57 (m,3-H,4-H), 1.55–1.47 (m,3-H'), 0.76 (d, J=6.3 Hz,5-Me), 0.73 (d,J=6.3 Hz,4-Me) ppm;

IR y (KBr) 3400, 2972, 1728, 1672, 1614, 1515, 1450, 1416, 1171, 1147 cm$^{-1}$;

MS (FAB) 610.6 ([MH$_2$-Boc]$^+$,100);

$[\alpha]_D$–19.9° (c 6.53, MeOH).

EXAMPLE 31

(58)

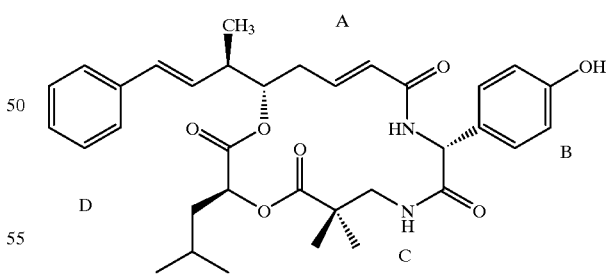

The Boc-amine (57), as prepared by Example 30 (109 mg,0.154 mmol), was dissolved in trifluoroacetic acid (5 mL,5 mM) and stirred at room temperature for 2 h. The reaction was concentrated in vacuo and dried under high vacuum to give the trifluoroacetate salt of amine (57) as a light brown foam. The crude amine salt (max. 0.154 mmol) was dissolved in dry DMF (31 mL) and diisopropylethylamine (80 µL, 0.462 mmol), followed by addition of pentafluorophenyl diphenylphosphinate (77 mg,0.2 mmol).

The resulting solution was stirred at room temperature under dry $N_2$ for 15 h, and concentrated in vacuo, and the residue was purified by column chromatography (gradient: 1–4% MeOH/$CH_2Cl_2$) to provide styrene (58) as a tan solid (54 mg, 59%).

$^1$H NMR ($CDCl_3$) Unit A d 7.36–7.15 (m,$PhH_5$), 6.79–6.69 (m,3-H), 6.54 (d,J=15.8 Hz,8-H), 5.98 (dd,J=15.8 and 8.8 Hz,7-H), 5.06–5.0 (m,5-H), 2.61–2.49 (m,6-H,4-H), 2.39–2.30 (m,3-H'), 1.10 (d,J=6.8 Hz,6-Me); Unit B d 7.90 (dd,J=10 and 1.68 Hz,OH), 7.65 (d,J=6.3 Hz,NH), 7.10 (d,J=8.5 Hz,$ArH_2$), 6.71 (d,J=8.4 Hz,$ArH_2$), 5.28 (d, J=6.5 Hz,2-H); Unit C d 3.55–3.47 (dd, J=13.3 and 10.1 Hz,3-$CH_2$), 3.00 (d,J=13.4 Hz,NH) 1.19 (s,2-Me), 1.16 (s,2-Me); Unit D d 4.90 (dd,J=10 and 3.5 Hz,2-H), 1.66–1.54 (m,3-H,4-H), 1.32–1.25 (m,3-H'), 0.67 (apparent t,J=7.1 Hz,5-Me,4-Me) ppm;

IR γ (KBr) 3418,3340,2960,1740,1713,1671,1514,1271, 1198,1155,972 $cm^{-1}$;

MS (FD) 590 ($M^+$,100);

$[\alpha]_D$+15.35° (c 3.91, $CHCl_3$).

EXAMPLE 32

(59)

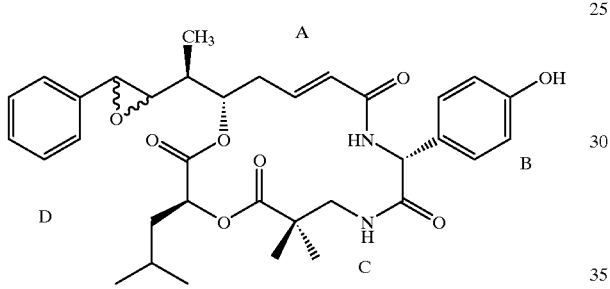

Styrene (58), prepared as described by Example 31 (42 mg, 0.0712 mmol) was suspended in dry dichloromethane (2.2 mL, 0.035 mM), and m-chloroperbenzoic acid (49 mg, 0.285 mmol) was added in one portion at room temperature. Dry tetrahydrofuran (0.3 mL) was added to produce a homogeneous solution. The reaction was stirred under $N_2$ at room temperature for 21 h and then diluted with further $CH_2Cl_2$ (15 mL). Organics were washed with 10% aq. $Na_2S_2O_5$ (10 mL), sat. aq. $NaHCO_3$ (10 mL), $H_2O$ (10 mL), dried ($MgSO_4$) and concentrated in vacuo to give a yellow solid. The crude product was initially purified by column chromatography (gradient: 1–5% MeOH/$CH_2Cl_2$) to give a 1:1.15 mixture of α:β $C_7$–$C_8$ epoxides as a white solid (23 mg, 54%). Reverse phase HPLC (column: 4.6×250 mm Kromsil C18; Eluent: 60% $CH_3CN$/$H_2O$; Flow: 1.0 mL/min; UV: 220 nm). Separation of the α:β mixture provided α-epoxide (2.3 mg, t=13.7 min) and β-epoxide (5.8 mg, t=12.1 min) as white solids.

β-Epoxide:
$^1$H NMR ($CDCl_3$) Unit A d 7.36–7.16 (m,PhH5), 6.70–6.79 (m,3-H), 5.91 (dd,J=15.5 and 5.18 Hz,2-H) 5.23–5.18 (m,5-H), 3.75 (d,J=1.67 Hz,8-H), 2.96 (dd,J=7.4 and 2.0 Hz,7-H), 2.72–2.67 (m,4-H), 2.44–2.39 (m,4-H) 1.81–1.88 (m,6-H), 1.13 (d,J=6.9 Hz,6-Me) ; Unit B d 7.66 (s,NH), 7.13 (d,J=8.5 Hz,$ArH_2$), 6.74 (d,J=8.5 Hz,ArH2), 5.27 (s,2-H); Unit C d 7.66 (s,NH), 3.49 (dd,J=13.6 and 10 Hz,3-$CH_2$), 1.20 (s,2-Me),1.18 (s,2-Me); Unit D d 4.93 (dd,J=10 and 3.2 Hz,2-H), 1.69–1.59 (m,3-H,4-H), 1.30–1.22 (m,3-H'), 0.79 (d,J=6.2 Hz,5-Me), 0.78 (d,J=6.3 Hz,4-Me) ppm.

We claim:

1. A process for the preparation of a compound of the formula:

(I)

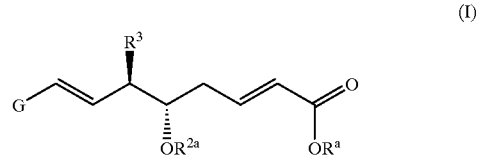

wherein

G is $C_1$–$C_{12}$ alkyl, $C_2$–$C_{12}$ alkenyl, $C_2$–$C_{12}$ alkynyl, or Ar;

Ar is an aromatic or heteroaromatic group or a substituted aromatic or heteroaromatic group;

$R^3$ is $C_1$–$C_6$ alkyl;

$R^{2a}$ is trityl or a suitable silyl protecting group; and $R^a$ is hydrogen, allyl or $C_1$–$C_6$ alkyl; or a pharmaceutically acceptable salt thereof;

said process comprising the steps of:

(a) contacting a compound of the formula:

(2)

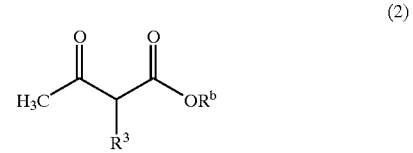

wherein $R^b$ is a suitable carboxy protecting group; and $R^3$ is as defined above; with a cyclizing agent to form a compound of the formula:

(3)

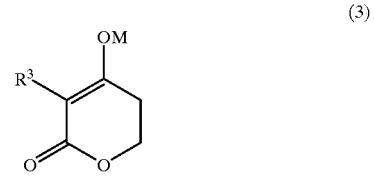

wherein $R^3$ is as defined above and M is hydrogen or a cation;

(b) stereoselectively reducing the compound of formula (3) with a stereoselective reducing agent to yield a compound of the formula:

(4)

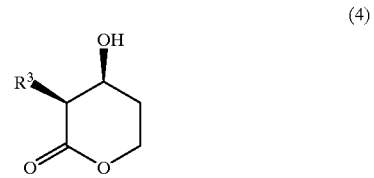

wherein $R^3$ is defined as above;

(c) reacting a compound of formula (4) with a hydroxy protecting agent to yield a compound of the formula:

(5)

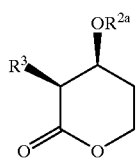

wherein $R^{2a}$ is tri($C_1$–$C_6$ alkyl)silyl, and $R^3$ is as defined above;

(d) reacting the compound of formula (5) with a reducing agent followed by an olefinating reagent to form a compound of the formula:

(6)

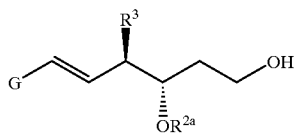

wherein G, $R^3$ and $R^{2a}$ are as defined above;

(e) reacting the compound of formula (6) with an oxidizing agent to provide a compound of the formula:

(7)

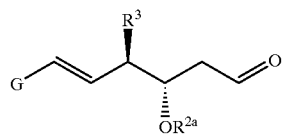

wherein G, $R^3$ and $R^{2a}$ are as defined above; and (f) reacting the compound of formula (7) with an alkyl ester forming agent, optionally with a hydrolyzing agent to provide a compound of formula (I) and optionally forming a pharmaceutically acceptable salt thereof.

2. A process according to claim 1 wherein G is Ar.

3. A process according to claim 1 wherein G is phenyl.

4. A process according to claim 3 wherein $R^3$ is methyl.

5. A process according to claim 3 wherein $R^a$ is hydrogen.

6. A process according to claim 3 wherein $R^a$ is methyl.

7. A process according to claim 1 wherein said compound of formula (I) is (5S,6R)-5-[(tert-butyldimethylsilyl)oxy]-6-methyl-8-phenylocta-2(E),7(E)-dienoic acid.

8. A process according to claim 1 wherein said compound of formula (I) is methyl (5S,6R)-5-[(tert-butyldimethylsilyl)oxy]-6-methyl-8-phenylocta-2(E),7(E)-dienoate.

9. A process according to claim 1 wherein said cyclizing agent is potassium t-butoxide.

10. A process according to claim 9 wherein said step (b) reducing agent is *Mortierella isabellina*.

11. A process according to claim 10 wherein said hydroxy protecting agent is t-butyldimethylsilyl chloride, t-butyldimethylsilyl trifluoromethane sulfonate, or chlorotrimethylsilane.

12. A process according to claim 11 wherein said step (d) reducing agent is an alkylated aluminum hydride and said olefinating reagent is benzyldiphenylphosphine oxide.

13. A process according to claim 12 wherein said oxidizing agent is oxalyl chloride/DMSO.

14. A process according to claim 13 wherein said alkyl ester forming agent is trimethyl phosphonoacetate.

15. The process according to claim 1 further comprising reacting the compound of formula (I) to prepare a cryptophycin compound of formula (II):

(II)

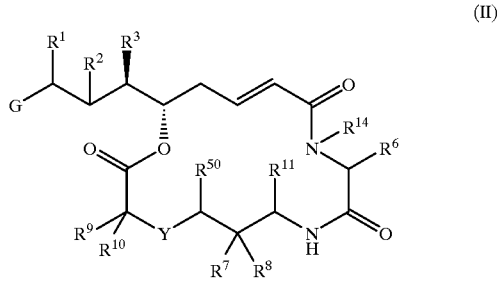

wherein

G is $C_1$–$C_{12}$ alkyl, $C_2$–$C_{12}$ alkenyl, $C_2$–$C_{12}$ alkynyl, or Ar;

Ar is an aromatic or heteroaromatic group or a substituted aromatic or heteroaromatic group;

$R^1$ is halogen and $R^2$ is OH or glycinate ester; or $R^1$ and $R^2$ may be taken together to form an epoxide ring; or $R^1$ and $R^2$ may be taken together to form a bond;

$R^3$ is $C_1$–$C_6$ alkyl;

$R^7$ and $R^8$ are each independently hydrogen or $C_1$–$C_6$ alkyl; or $R^7$ and $R^8$ taken together form a cyclopropyl or cyclobutyl ring;

$R^9$ is hydrogen, $C_1$–$C_6$ alkyl, $C_2$–$C_6$ alkenyl, $C_2$–$C_6$ alkynyl, —($CH_2$)$_m$—($C_3$–$C_5$)cycloalkyl or benzyl, wherein m is the integer one to three;

$R^{10}$ is hydrogen or $C_1$–$C_6$ alkyl;

$R^{11}$ is hydrogen, $C_1$–$C_6$ alkyl, phenyl or benzyl;

$R^{14}$ is hydrogen or $C_1$–$C_6$ alkyl;

$R^{50}$ is hydrogen or (=O);

Y is CH, O, $NR^{12}$, S, SO, $SO_2$, wherein $R^{12}$ is H or $C_1$–$C_3$ alkyl;

$R^6$ is $C_1$–$C_6$ alkyl, substituted ($C_1$–$C_6$)alkyl, ($C_3$–$C_8$) cycloalkyl, substituted ($C_3$–$C_8$)cycloalkyl, a heteroaromatic or substituted heteroaromatic group or a group of formula (IA), (IB) or (IC):

(IA)

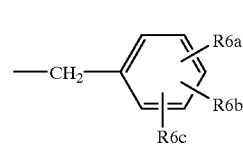

(IB)

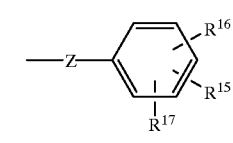

(IC)

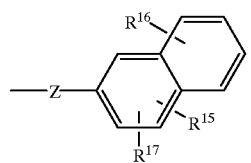

$R^{6a}$, $R^{6b}$, and $R^{6c}$ independently are H, ($C_1$–$C_6$)alkyl, halo $NR^{18}R^{19}$ or $OR^{18}$;

$R^{15}$, $R^{16}$, and $R^{17}$ independently are hydrogen, halo, ($C_1$–$C_6$)alkyl, $OR^{18}$, O-aryl, $NH_2$, $NR^{18}R^9$, $NO_2$, $OPO_4H_2$, ($C_1$–$C_6$ alkoxy)phenyl, S-benzyl, $CONH_2$, $CO_2H$, $PO_3H_2$, $SO_2R^{23}$, or Z';

$R^{18}$ and $R^{19}$ independently are hydrogen or $C_1$–$C_6$ alkyl;

$R^{23}$ is hydrogen or ($C_1$–$C_3$)alkyl;

Z is —$(CH_2)_n$— or ($C_3$–$C_5$)cycloalkyl;

n is 0, 1, or 2; and

Z' is an aromatic or substituted aromatic group; or a pharmaceutically acceptable salt thereof.

* * * * *